US011130959B2

(12) United States Patent
Bernacchi et al.

(10) Patent No.: US 11,130,959 B2
(45) Date of Patent: Sep. 28, 2021

(54) METHODS AND COMPOSITIONS FOR COMBINATIONS OF MUTATIONS ASSOCIATED WITH HERBICIDE RESISTANCE/TOLERANCE IN RICE

(71) Applicant: RICETEC, INC., Alvin, TX (US)

(72) Inventors: Dario Bernacchi, Friendswood, TX (US); Caleb Knepper, League City, TX (US); Russell D. Rasmussen, League City, TX (US); Federico Cuevas, League City, TX (US); Venu Reddyvari Channarayappa, Friendswood, TX (US); Melissa Hinga, League City, TX (US); Melissa Shannon Moon, Pearland, TX (US)

(73) Assignee: RICETEC, INC., Alvin, TX (US)

( * ) Notice: Subject to any disclaimer, the term of this patent is extended or adjusted under 35 U.S.C. 154(b) by 182 days.

(21) Appl. No.: 15/669,086

(22) Filed: Aug. 4, 2017

(65) Prior Publication Data

US 2018/0066276 A1     Mar. 8, 2018

Related U.S. Application Data

(60) Provisional application No. 62/371,582, filed on Aug. 5, 2016.

(51) Int. Cl.
*C12N 15/82* (2006.01)
*A01G 22/22* (2018.01)

(52) U.S. Cl.
CPC .. *C12N 15/8274* (2013.01); *C12Y 604/01002* (2013.01); *A01G 22/22* (2018.02)

(58) Field of Classification Search
None
See application file for complete search history.

(56) References Cited

U.S. PATENT DOCUMENTS

| | | |
|---|---|---|
| 4,443,971 A | 4/1984 | Chaleff |
| 5,290,696 A | 3/1994 | Somers et al. |
| 5,428,001 A | 6/1995 | Somers et al. |
| 5,539,092 A | 7/1996 | Haselkorn et al. |
| 5,736,629 A | 4/1998 | Croughan |
| 5,756,290 A | 5/1998 | Haselkorn et al. |
| 5,767,373 A | 6/1998 | Ward et al. |
| 5,792,627 A | 8/1998 | Haselkorn et al. |
| 5,801,233 A | 9/1998 | Haselkorn et al. |
| 5,910,626 A | 6/1999 | Haselkorn et al. |
| 5,939,602 A | 8/1999 | Volrath et al. |
| 5,972,644 A | 10/1999 | Haselkorn et al. |
| 6,066,779 A | 5/2000 | Yan |
| 6,069,298 A | 5/2000 | Gengenbach et al. |
| 6,084,155 A | 7/2000 | Volrath et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,281,168 B1 | 8/2001 | Shaner et al. |
| 6,282,837 B1 | 9/2001 | Ward et al. |
| 6,288,306 B1 | 9/2001 | Ward et al. |
| 6,308,458 B1 | 10/2001 | Volrath et al. |
| 6,399,342 B1 | 6/2002 | Haselkorn et al. |
| 6,448,476 B1 | 9/2002 | Barry |
| 6,455,688 B1 | 9/2002 | Slabas et al. |
| 6,727,414 B2 | 4/2004 | Moldenhauer et al. |
| 6,808,904 B2 | 10/2004 | Ward et al. |
| 6,870,075 B1 | 3/2005 | Beetham et al. |
| 6,911,589 B2 | 6/2005 | Johnson |
| 6,943,280 B2 | 9/2005 | Croughan |
| 6,953,881 B2 | 10/2005 | Tillman |
| 6,956,154 B2 | 10/2005 | Xie |
| 7,005,567 B2 | 2/2006 | Tillman |
| 7,094,606 B2 | 8/2006 | Arntzen et al. |
| 7,141,726 B2 | 11/2006 | Moldenhauer et al. |
| 7,253,347 B2 | 8/2007 | Linscombe |
| 7,301,083 B2 | 11/2007 | Sarreal et al. |
| 7,304,223 B2 | 12/2007 | Sarreal et al. |
| 7,345,221 B2 | 3/2008 | Croughan |
| 7,351,891 B2 | 4/2008 | Sarreal et al. |
| 7,351,892 B2 | 4/2008 | Sarreal et al. |
| 7,351,893 B2 | 4/2008 | Sarreal et al. |
| 7,399,905 B2 | 7/2008 | Croughan |
| 7,429,697 B2 | 9/2008 | Moldenhauer et al. |
| 7,485,784 B2 | 2/2009 | Sarreal et al. |
| 7,579,531 B2 | 8/2009 | Jodari |
| 7,612,269 B2 | 11/2009 | Jodari |
| 7,622,661 B2 | 11/2009 | Johnson |
| 7,642,434 B2 | 1/2010 | Moldenhauer |
| 7,642,435 B2 | 1/2010 | Sarreal et al. |
| 7,671,254 B2 | 3/2010 | Tranel et al. |
| 7,687,690 B2 | 3/2010 | Johnson et al. |
| 7,754,947 B2 | 7/2010 | Croughan |
| 7,786,360 B2 | 8/2010 | Linscombe |
| 7,803,991 B2 | 9/2010 | Daniell |
| 7,820,883 B2 | 10/2010 | Walsh et al. |
| 7,838,733 B2 | 11/2010 | Wright et al. |
| 7,842,856 B2 | 11/2010 | Tranel et al. |
| H2258 H | 6/2011 | Arnevik et al. |
| 7,973,083 B2 | 7/2011 | Clemens et al. |
| 8,071,847 B2 | 12/2011 | Walsh et al. |

(Continued)

FOREIGN PATENT DOCUMENTS

| | | |
|---|---|---|
| CA | 2823290 | 7/2012 |
| CN | 101595886 | 12/2009 |

(Continued)

OTHER PUBLICATIONS

Kukorelli et al. (2013) Int J Pest Manag 59(3):165-73.*

(Continued)

*Primary Examiner* — Russell T Boggs
(74) *Attorney, Agent, or Firm* — Barnes & Thornburg LLP; Alice O. Martin

(57) ABSTRACT

Rice is described that is tolerant/resistant to herbicides, for example, ACCase inhibitors, and HPPD inhibitors, or both. For ACCase inhibitors, 2 different chromosome regions act synergistically in providing resistance/tolerance to the same herbicide class. Use of the herbicide resistant/tolerant rice for weed control and methods of producing tolerant/resistant rice are also disclosed.

13 Claims, 34 Drawing Sheets

Specification includes a Sequence Listing.

(56) References Cited

U.S. PATENT DOCUMENTS

| | | | |
|---|---|---|---|
| 8,088,979 | B2 | 1/2012 | Walsh et al. |
| 8,097,774 | B2 | 1/2012 | Hawkes et al. |
| 8,106,276 | B2 | 1/2012 | Luo |
| 8,134,058 | B2 | 3/2012 | Moldenhauer |
| 8,153,870 | B2 | 4/2012 | Re et al. |
| 8,268,622 | B2 | 9/2012 | Gocal et al. |
| 8,283,536 | B1 | 10/2012 | Re et al. |
| 8,283,537 | B1 | 10/2012 | Re et al. |
| 8,288,635 | B2 | 10/2012 | Moldenhauer |
| 8,449,917 | B2 | 5/2013 | Hiteshkumar et al. |
| 8,598,080 | B2 | 12/2013 | Linscombe |
| 8,796,177 | B2 | 8/2014 | Mann et al. |
| 8,847,017 | B2 | 9/2014 | Poree et al. |
| 8,853,495 | B2 | 10/2014 | Poree et al. |
| 8,853,496 | B2 | 10/2014 | Poree et al. |
| 8,859,856 | B2 | 10/2014 | Poree et al. |
| 9,303,270 | B2 | 4/2016 | Hinga et al. |
| 9,370,149 | B2 | 6/2016 | Hinga et al. |
| 2001/0031704 | A1 | 10/2001 | Hacker |
| 2004/0107465 | A1 | 6/2004 | Tillman et al. |
| 2004/0123343 | A1 | 6/2004 | La Rosa et al. |
| 2004/0242422 | A1 | 12/2004 | Hofer et al. |
| 2007/0074303 | A1 | 3/2007 | McCutchen et al. |
| 2008/0256668 | A1 | 10/2008 | Beetham et al. |
| 2008/0300139 | A1 | 12/2008 | Zawierucha et al. |
| 2009/0093366 | A1 | 4/2009 | Wright et al. |
| 2009/0165166 | A1 | 6/2009 | Feng et al. |
| 2009/0235395 | A1 | 9/2009 | Arntzen et al. |
| 2009/0240073 | A1 | 9/2009 | Barry et al. |
| 2010/0029485 | A1 | 2/2010 | Livore |
| 2010/0048405 | A1 | 2/2010 | Raymer et al. |
| 2010/0197503 | A1 | 8/2010 | Hawkes |
| 2010/0293628 | A1 | 11/2010 | Tuinstra et al. |
| 2011/0028324 | A1 | 2/2011 | Cordingley et al. |
| 2011/0124503 | A1 | 5/2011 | Wright et al. |
| 2011/0214196 | A1 | 9/2011 | Raymer et al. |
| 2012/0284812 | A1* | 11/2012 | Mankin ............. A01H 5/10 800/260 |
| 2012/0284853 | A1 | 11/2012 | Mankin et al. |
| 2013/0019349 | A1 | 1/2013 | Gocal et al. |
| 2013/0023416 | A1* | 1/2013 | Hinga ............... A01H 5/10 504/235 |
| 2013/0111618 | A1 | 5/2013 | Mankin et al. |
| 2013/0333062 | A1* | 12/2013 | Rehman etal. ...... A01H 5/10 800/260 |
| 2014/0024530 | A1 | 1/2014 | Poree et al. |
| 2014/0045686 | A1 | 2/2014 | Mankin et al. |
| 2014/0250543 | A1 | 9/2014 | Ostlie et al. |
| 2014/0274710 | A1 | 9/2014 | Mann et al. |
| 2015/0038331 | A1* | 2/2015 | Hinga ............. C12Y 113/11027 504/136 |

FOREIGN PATENT DOCUMENTS

| | | |
|---|---|---|
| EP | 2453012 | 5/2012 |
| WO | WO 95/29246 | 11/1995 |
| WO | WO 98/54330 | 12/1998 |
| WO | WP 2009/034188 | 3/2009 |
| WO | WO 2010/040485 | 4/2010 |
| WO | WO 2010/046437 | 4/2010 |
| WO | WO 2011/028832 | 3/2011 |
| WO | WO 2011/028833 | 3/2011 |
| WO | WO 2011/028836 | 3/2011 |
| WO | WO 2013/016210 | 1/2013 |
| WO | WO 2015/025031 | 2/2015 |

OTHER PUBLICATIONS

Kaundun et al. (2013) PLOS ONE 8(2):e58012.*
Délye (2013) Pest Manag Sci 69:176-87.*
Goldsbrough et al. (1990) Plant Sci 72:53-62.*
Sasaki et al. (2002) Nature 420:312-16.*
Examination Report issued in App. No. PH 1-2014-500183 (dated Jan. 8, 2018).
Abe et al., "Genome sequencing reveals agronomically important loci in rice using MutMap," Nat. Biotech., 30, 174-178 (2012).
Chen et al, "Genome-wide association analyses provide genetic and biochemical insights into natural variation in rice metabolism," Nature Genetics, 46: 714-721 (2014).
Collavo, "Resistance to graminicides in monocotyledons weeds, Case studies of Lolium spp. and Phalaris paradoxa in Italy," Ph.D. Dissertation, University of Padova (2008).
Cruz-Hipolito et al., "Resistance mechanism to acetyl coenzyme A carboxylase inhibiting herbicides in Phalaris paradoxa collected in Mexican wheat fields," Plant Soil, 355:121-130 (2012).
Délye et al, "'Universal' primers for PCR-sequencing of grass chloroplastic acetyl-CoA carboxylase domains involved in resistance to herbicides," Weed Research, 45:323-330 (2005).
Delye et al., "Cross-resistance patterns to ACCase-inhibiting herbicides conferred by mutant ACCase isoforms in Alopecurus myosuroides Huds. (black-grass), re-examined at the recommend herbicide field rate," Pest Management Science, 64(11): 1179-86 (2008).
Delye et al., "Deciphering the evolution of herbicide resistance in weeds," Trends in Genetics, 29(11): 649-658 (2013).
Délye et al., "An Isoleucine Residue within the Carboxyl-Transferase Domain of Multidomain Acetyl-Coenzyme A Carboxylase Is a Major Determinant of Sensitivity to Aryloxyphenoxypropionate But Not to Cyclohexanedione Inhibitors," Plant Physiology, 132: 1716-1723 (2003).
Délye et al., "Molecular Bases for Sensitivity to Acetyl-Coenzyme A Carboxylase Inhibitors in Black-Grass," Plant Physiology, 137: 794-806 (2005).
Guo et al., Proc. Natl. Acad. Sci. USA 101: 9205-9210 (2004).
Jain, "Tissue culture-derived variation in crop improvement," Euphytica, 118:153-166 (2001).
Liu et al., "Single-Site Mutations in the Carboxyltransferase Domain of Plastid Acetyl-CoA Carboxylase Confer Resistance to Grass-Specific Herbicides," PNAS, 104(9): 3627-3632 (2007).
Matringe et al., "p-Hydroxyphenylpyruvate dioxygenase inhibitor-resistant plants," Pest. Manage. Sci., 61:269-276 (2005).
Okuzaki et al., "Chimeric RNA/DNA oligonucleotide-directed gene targeting in rice," Plant Cell Rep., 22:509-512 (2004).
Oryza sativa acetyl-coenzyme A carboxylase mutant G2107S, Database Geneseq [Online], accession No. AZG28702, Apr. 28, 2001.
Oryza sativa Japonica Group acetyl-coenzyme A carboxylase, Database Enbl accession No. AZG73608, May 12, 2011.
Ostlie et al., "Development and characterization of mutant winter wheat (Triticum aestivum L.) accessions resistant to the herbicide quizalofop," Theor. Appl. Genet., 128:343-351 (2015).
Ouyang et al., Nucleic Acid Research, 35 Database Issue: D846-851 (Jan. 1, 2007).
Rogue, A Novel Herbicide for US Rice Production, Louisiana Agricultural Technology and Management Conference, Feb. 18, 2016.
Ruiz-Santaella et al., Detection of a new mutation of glycine to serine in the ACCase of a resistant biotype of Phalaris paradoxa. In: Annual Meeting of the Weed Science Society of America, Abstracts, New York: WSSA, 46:93 (2006).
Rutger et al., "Registration of nine indica germplasms of rice," Crop Sci., 45:1170-1171 (2005).
Sandoski et al., Rogue™—A Novel Herbicide for US Rice Production, Louisiana Agrictultural Technology and Management Conference, Feb. 18, 2016.
Scarabel et al., "Allelic variation of the ACCase gene and response to ACCase-inhibiting herbicides in pinoxaden-resistant Lolium spp.," Pest Management Science, 67(8): 932-941 (2011).
Sekino et al., "Herbicidal activity of a new paddy bleaching herbicide, benzobicyclon," J. Pest. Sci., 33(4): 364-370 (2008).
Suzuki et al., "MNU-induced mutant pools and high performance Tilling enable finding of any gene mutation in rice," Mol. Genet. Genomics, 279:213-223 (2008).
UniProt Accession No. A2Y2U1.

(56) References Cited

OTHER PUBLICATIONS

Yu et al., "Diversity of Acetyl-Coenzyme A Carboxylase Mutations in Resistant *Lolium* Populations: Evaluation Using Clethodim$^1$[$^{OA}$]," *Plant Physiology*, 145: 547-558 (2007).

Zhu et al., "Computational Simulations of the Interactions between Acetyl-Coenzyme-A Carboxylase and Clodinafop: Resistance Mechanism Due to Active and Nonactive Site Mutations," J. Chem. Inf. Model, 49(8): 1936-1943 (2009).

Zhu et al., The resistance mechanism research of ACCase inhibitor, *Journal of Huazhong Normal University Natural Sciences*, 43(1): 76-82 (2009).

Anyszka et al., "The Response of Snap Bean and Barnyardgrass (*Echinochloa crus-galli*) on quizalofop-P-Tefuryl," Vegetable Crops Research Bulletin, 51:95-102 (1999) (Abstract).

Maneechote et al., "Controlling invasive wild rice with ACCase-inhibiting herbicides," Proceedings of the 4th Int'l Crop Science Congress, Brisbane, Australia (2004).

Maneechote et al., "Resistance to ACCase-inhibiting herbicides in sprangletop (*Leptochloa chinensis*)," Weed Science, 53:290-295 (2005).

Kawahara et al., "Improvement of the *Oryza sativa* Nipponbare reference genome using next generation sequence and optical map data," Rice 6(4): 1-10 (2013).

Int'l Rice Genome Sequencing Project, "The Map-based sequence of the rice genome," Nature, 436: 793-800 (2005).

Tong, "Acetyl-coenzyme A carboxylase: crucial metabolic enzyme and attractive target for drug discovery," CMLS Cellular and Molecular Life Sciences (2005), 62(16): 1784-1803.

Zhao et al, "Target site mutations and cytochrome P450s confer resistance to fenoxaprop-P-ethyl and mesosulfuron-methyl in *Alopecurus aequalis*," Pest Manag Sci, (2019) 75: 204-214.

Zhao et al., "Trp-1999-Ser mutation of acetyl-CoA carboxylase and cytochrome P450s-involved metabolism confer resistance to fenoxaprop-P-ethyl in *Polypogon fugax*," Pest Manag Sci, (2019) 75: 3175-3183.

\* cited by examiner

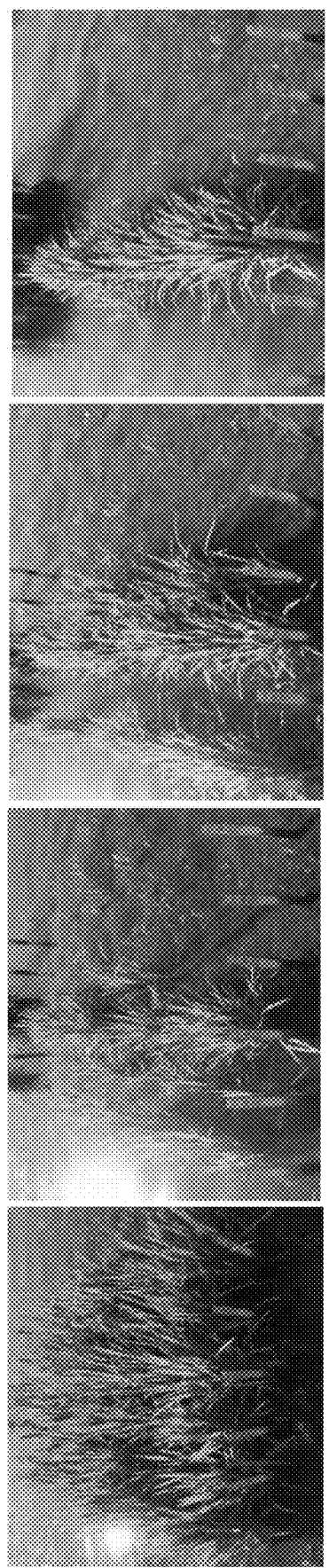

METHODS AND COMPOSITIONS FOR COMBINATIONS OF MUTATIONS ASSOCIATED WITH HERBICIDE RESISTANCE/TOLERANCE IN RICE

CROSS REFERENCE TO RELATED APPLICATIONS

This application claims the benefit of priority under 35 U.S.C. § 119(e) to U.S. Provisional Patent Application No. 62/371,582, filed Aug. 5, 2016. The disclosure set forth in the reference application is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 4, 2017, is named 50970-267333_SEQ.txt and is 58,089 bytes in size.

BACKGROUND

Mutant rice is disclosed that is (1) resistant/tolerant to ACCase inhibitors at a relatively high concentration of inhibitors due to synergistic action of genes in 2 regions of 2 different chromosomes; (2) resistant/tolerant to both HPPD and ACCase inhibiting herbicides; and (3) resistant/tolerant only to 4-hydroxyphenylpyruvate dioxygenase (HPPD) inhibiting herbicides. Methods of weed control are disclosed using rice with these herbicide resistant/tolerant crops in fields that may be sprayed or otherwise treated with the herbicide. Methods to produce the herbicide resistant/tolerant rice are also disclosed.

Value of Rice Crops

Rice is an ancient agricultural crop and today is one of the principal food crops of the world. There are two cultivated species of rice: *Oryza sativa* L., the Asian rice, and *Oryza glaberrima* Steud., the African rice. The Asian species constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valley of California. Other countries, in particular in South America and the East, are major rice producers.

Rice is one of the few crops that can be grown in a shallow flood as it has a unique structure allowing gas exchange through the stems between the roots and the atmosphere. Growth in a shallow flood results in the best yields and is the reason that rice is usually grown in heavy clay soils, or soils with an impermeable hard pan layer just below the soil surface. These soil types are usually either not suitable for other crops or at best, the crops yield poorly.

The constant improvement of rice is imperative to provide necessary nutrition for a growing world population. A large portion of the world population consumes rice as their primary source of nutrition, and crops must thrive in various environmental conditions including competing with weeds and attacks by unfavorable agents. Rice improvement is carried out through conventional breeding practices and also by recombinant genetic techniques. Though appearing straightforward to those outside this discipline, crop improvement requires keen scientific and artistic skill and results are generally unpredictable.

Although specific breeding objectives vary somewhat in the different rice producing regions of the world, increasing yield is a primary objective in all programs.

Plant breeding begins with the analysis and definition of strengths and weaknesses of cultivars in existence, followed by the establishment of program goals, to improve areas of weakness to produce new cultivars. Specific breeding objectives include combining in a single cultivar an improved combination of desirable traits from the parental sources. Desirable traits may be introduced due to spontaneous or induced mutations. Desirable traits include higher yield, resistance to environmental stress, diseases and insects, better stems and roots, tolerance to low temperatures, better agronomic characteristics, nutritional value and grain quality.

For example, the breeder initially selects and crosses two or more parental lines, followed by selection for desired traits among the many new genetic combinations. The breeder can theoretically generate billions of new and different genetic combinations via crossing. Breeding by using crossing and selfing, does not imply direct control at the cellular level. However, that type of control may be achieved in part using recombinant genetic techniques.

Pedigree breeding is used commonly for the improvement of self-pollinating crops such as rice. For example, two parents which possess favorable, complementary traits are crossed to produce an $F_1$ generation. One or both parents may themselves represent an $F_1$ from a previous cross. Subsequently a segregating population is produced, by growing the seeds resulting from selfing one or several $F_1$s if the two parents are pure lines, or by directly growing the seed resulting from the initial cross if at least one of the parents is an $F_1$. Selection of the best individual genomes may begin in the first segregating population or $F_2$; then, beginning in the $F_3$, the best individuals in the best families are selected. "Best" is defined according to the goals of a particular breeding program e.g., to increase yield, resist diseases. Overall a multifactorial approach is used to define "best" because of genetic interactions. A desirable gene in one genetic background may differ in a different background. In addition, introduction of the gene may disrupt other favorable genetic characteristics. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new parental lines.

Backcross breeding has been used to transfer genes for a highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The process is used to recover all of the beneficial characteristics of the recurrent parent with the addition of the new trait provided by the donor parent.

Promising advanced breeding lines are thoroughly tested and compared to appropriate standards in environments representative of the commercial target area(s) for at least three or more years. The best lines are candidates for new commercial varieties or parents of hybrids; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is not only a time-consuming process, but requires precise forward planning, efficient use of resources, and a minimum of changes in direction. The results include novel genetic combinations not found in nature.

Some improvement of rice through breeding may be restricted to the natural genetic variation in rice and hybridizing species, such as wild rice. The introduction of new variation in a breeding program is usually through the crossing program as described, such as pedigree or backcross breeding. However, occasionally natural mutations are found that result in the introduction of new traits such as disease resistance or height changes. Breeders have also developed new traits by inducing mutations (small changes in the DNA sequence) into a rice genome. Some of these mutations or combination of genes are not found in nature. Commonly, EMS or sodium azide plus MNU are used as mutagenic agents. These chemicals randomly induce single base changes in DNA, usually of G and C changed to A and T. Overall effects are unpredictable. Most of these changes have no effect on the crop because they fall either outside the gene coding regions or don't change the amino acid sequence of the gene product. However, some produce new traits or incorporate new DNA changes into previous lines.

Until recently, a breeder had no direct control of mutation sites in the DNA sequence. The identification of useful changes is due to the random possibility that an effective mutation will be induced and that the breeder will recognize the phenotypic effects of the change and will be able to select and expand crops of rice having that mutation.

Seeds are treated with the mutagenic chemical or other agent and immediately planted to grow and produce M2 seed. The M2 seed will carry numerous new variations; therefore, no two experiments will produce the same combinations. Among these variations new traits previously not existing in rice and unavailable for selection by a plant breeder may be found and used for rice improvement.

To find new traits the breeder must use efficient and strategic selection strategies because the mutagenic process has an extremely low frequency of useful new combinations. Among thousands of induced new genetic variants there may be only one with a desirable new trait. An optimal selection system will screen through thousands of new variants and allow detection of a few or even a single plant that might carry a new trait. After identifying or finding a possible new trait the breeder must develop a new cultivar by pedigree or backcross breeding, followed by extensive testing to verify the new trait and cultivar exhibits stable and heritable value to rice producers.

Using recombinant genetic techniques, nucleic acid molecules with mutations that encode improved characteristics in rice, may be introduced into rice that have commercially suitable genomes. New methods of gene manipulation such as CRISPR, and modern sequencing techniques allow breeders to direct complex crop improvements, and accelerate the progress to commercialization. After a mutation is identified by whatever method, it may be transferred into rice by recombinant techniques, and tested to be sure fitness is not deleteriously affected.

Herbicide Resistance in Rice

Weeds and other competitors for resources in crop fields compete for resources and greatly reduce the yield and quality of the crop. Weeds have been controlled in crops through the application of selective herbicides that kill the weeds, but do not harm the crop. Usually selectivity of the herbicides is based on biochemical variations or differences between the crop and the weeds. Some herbicides are non-selective, meaning they kill all or almost all plants. Non-selective or broad spectrum herbicides can be used in crops if new genes are inserted that express specific proteins that convey tolerance or resistance to the herbicide. Resistance to herbicides has also been achieved in crops through genetic mutations that alter proteins and biochemical processes. These mutations may arise in nature, but mostly they have been induced in crops either in vitro in tissue cultures or by inducing mutations in vivo. Unfortunately in some instances, especially with repeated use of a particular herbicide, weeds have developed resistance through the unintended selection of natural mutations that provide resistance. When weeds become resistant to a particular herbicide, that herbicide is no longer useful for weed control. The development of resistance in weeds is best delayed through alternating the use of different modes of action to control weeds, interrupting development of resistant weeds.

Rice production is plagued by broad leaf plants and a particularly hard to control weed called red rice. One difficulty arises because red rice is so genetically similar to cultivated rice (they occasionally cross pollinate) that there are no selective herbicides available that target red rice, yet do not harm the cultivated rice. Control is currently provided in commercial rice production through the development of mutations found in rice that render rice resistant to broad spectrum herbicides e.g. imidazolinone and sulfonylurea herbicides. Rice resistant to herbicides that inhibit other deleterious plants, such as broad leaf plants, are needed.

To date, most herbicide tolerant rice is associated with a single genetic change, notably a change in a target enzyme altering its response to inhibitors. More complex causes of increased resistance/tolerance would be desirable to introduce into plants, because they move further from natural causations, and provide more obstacles to weeds developing resistance.

Finding new mutations in rice that makes it resistant to a variety of herbicides, to combinations of herbicides with alternative modes of action, particularly enhanced resistance, would greatly benefit rice production. Obtaining and incorporating genes for herbicide resistance into rice genomes with additional favorable characteristics, and alternative resistances is challenging, unpredictable, time consuming and expensive, but necessary to meet the world's increasing food needs.

SUMMARY

Described and disclosed herein are novel and distinctive rice lines with unique, in some combinations synergistic, resistances to herbicides—in particular to ACCase and HPPD inhibiting herbicides, and combinations thereof. ACCase inhibiting herbicides include quizalofop, propaquizafop and fluazifop. HPPD inhibiting herbicides include mesotrione, benzobicyclon, and combinations thereof.

Genetic Regions Associated with Resistance/Tolerance to FOP Family Herbicides

Mutagenized population development and screening performed for FOP herbicide resistance, allowed the identification of two mutated genetic regions associated with resistance to Quizalofop. One of these resistance causing regions, designated RTA1, was determined to be located in the known target locus of the ACCase gene located in Chromosome 5. It therefore constitutes a typical example of target specific herbicide resistance (TSR). Another agent, designated RTA2, was determined to be located in Chromosome 1, in a region formerly unreported as involved in FOP herbicide tolerance, and unrelated to the ACCase amino acid sequence. This second region appears to be a case of a non-target specific resistance (NTSR) agent.

The genetic backgrounds are not the same in the two lines RTA1 and RTA2. One is mutagenized, the other is converted back to the conventional line.

The RTA1 and RTA2 lines are homozygous for the ACCase inhibitor resistance/tolerant traits and are inbred.

The herbicide tolerance inducing genetic regions of RTA1 and RTA2 have essentially recessive effects that require homozygosity to have the full effect of the tolerance. The lines are designated "RTA1 and RTA2" but these terms also refer to the specific mutated regions within the lines. The regions are associated with herbicide tolerance.

RTA1 Confers Resistance by a TSR Mechanism

The mutated resistance gene RTA1, was determined to be a single point mutation in the DNA of the ACCase gene, wherein a guanine (G) nucleotide in the wild type, unmutated rice is replaced by adenine in the mutant DNA, which results in a change in the amino acid sequence of glycine to serine (G to S) in the expressed protein target site affecting a known active site in the protein (G2096S). This results in change of herbicide action at a critical binding site in the ACCase enzyme (found in chloroplasts), that affects the binding of the herbicide to the ACCase protein, and blocks the expression of phytotoxicity. Thus plants carrying the mutation do not die by contact with the herbicide. The mutation was identified by sequence analysis of the ACCase gene and exactly matches identical FOP-resistance mutations identified in homologous positions in other crops, and in plant species.

RTA2 Confers Resistance by a NTSR Mechanism

In the case of RTA2, the mutation associated with resistance/tolerance was mapped to Chr.1 (unlike RTA1 which is located on Chr.5), as evidenced both by linkage mapping analysis and later by MutMap (mutation mapping by whole genome sequencing strategy). In this region of Chromosome 1 there is no report of duplicated or orthologous ACCase or ACCase-like genes, the target gene of the FOP herbicides. Therefore, the mechanism of tolerance to Quizalofop caused by this mutation RTA2, cannot be characterized as "target site". Instead, RTA2 is considered a "non-target site" resistance genetic region or site, also referred to in the literature as "non-target site or metabolism based" herbicide tolerance (NTSR).

Weed Control

These new lines present improved opportunities for weed control.

A method to control weeds in a rice field uses the rice in the field resistant to a plurality of herbicides.

The rice field is contacted with at least one herbicide, or a plurality of herbicides, for example, any that may belong to the family of herbicides known as ACCase-inhibitors, or any that may belong to the class of herbicides known as HPPD-inhibiting herbicides.

Producing Herbicide Resistant Rice Plants

A method for growing herbicide resistant/tolerant rice plants includes (a) planting resistant rice seeds; (b) allowing the rice seeds to sprout; (c) applying one or more herbicides to the rice sprouts at levels of herbicide that would normally inhibit the growth of a rice plant, and selecting surviving plants for crop expansion.

Methods of producing herbicide-tolerant rice plants may also use a transgene or plurality of transgenes, or new methods of genetic manipulation such as CRISPR. One embodiment of such a method is transforming a cell of a rice plant with transgenes, wherein the transgenes encode 2 different genetic regions that when combined lead to synergistic resistance to ACCase inhibitors, or an HPPD and an ACCase enzyme that confers tolerance in resulting rice plants to one or more herbicides. Any suitable cell may be used in the practice of these methods, for example, the cell may be in the form of a callus.

A monocot plant tolerant/resistant to ACCase inhibitors, at levels higher than those tolerated by plants without genetic regions from the genomes of rice lines RTA2 and RTA1 or the equivalents, is suitable for weed control and new line development. Equivalents would be genetic regions with the same coding result that is on chromosome 5, and the same vector of mutations as in chromosome 1, with synergistic effects when combined.

The region in the genome of rice line RTA2 is a mutation encoding a substitution of glycine to serine at position 2096.

The region of rice chromosome number 1 in rice line RTA2 is between position C1-32083963 and C1-36386713 with mutant nucleotide sequences as shown in Table 1A and 1B. This region is a tightly linked region with mutations shown at the individual positions in Tables 1A and 1B. When the vector of mutations is in a rice plant the RTA2 effect is present.

Seeds of the rice plants disclosed herein are deposited as ATCC accession numbers PTA-122646 and 124233.

A method of producing rice resistant to ACCase herbicide inhibitors, at levels significantly higher than those tolerated by plants without genetic regions conferring resistance includes:

a. obtaining genetic regions that are substantially the same as the regions in genomes of rice designated RTA1 and RTA2 that confer resistance/tolerance to ACCase inhibitors; and
b. introducing the genetic regions into rice lines to replace wild type regions not conferring herbicide resistance at levels useful for commercial crops.

Cells derived from herbicide resistant seeds, plants grown from such seeds and cells derived from such plants, progeny of plants grown from such seed and cells derived from such progeny are within the scope of this disclosure. The growth of plants produced from deposited seeds, and progeny of such plants will typically be resistant/tolerant to herbicides, e.g. ACCase inhibiting, HPPD inhibiting or both, at levels of herbicides that would normally inhibit the growth of a corresponding wild-type plant. There are some natural (non-induced) levels of tolerance to some herbicides, but those regions cannot protect plants at levels that would be commercially useful.

BRIEF DESCRIPTION OF DRAWINGS

FIG. 1 is a graphical representation of a trait tolerance trial; the trial was planted, mesotrione was applied at the indicated rates about 1 month later (3-4 leaf stage), and a second application was applied on the two indicated treatments about 1 week later; the rice was evaluated for the percent of injury or damage as compared to unsprayed rice twenty-one days after the first herbicide application; line ML0831266-03093 is the HPPD resistant line and R0146 and P1003 are control lines with no induced mutation; the line PL1214418M2-73009 was selected out of a cross between the HPPD tolerant line ML0831266-03093 (parent is P1003) and the ACCase resistant line ML0831265-01493 (parent is R0146). The newly developed line PL1214418M2-73009 shows equivalent tolerance as the original HPPD tolerant line ML0831266-03093 to HPPD inhibitors.

FIG. 2 is a graphical representation of a trait tolerance trial; the trial rice were planted, quizalofop was applied at the indicated rates about 5 weeks later (initiating tillering); the rice was evaluated for the percent of injury or damage as compared to unsprayed rice four weeks after herbicide application; line ML0831265-01493 is the ACCase resistant line and R0146 and P1003 are control lines; the line PL1214418M2-73009 was selected out of a cross between the HPPD tolerant line ML0831266-03093 (parent is P1003) and the ACCase tolerant line ML0831265-01493 (parent is R0146). The newly developed line PL1214418M2-73009 which has combined resistance shows equivalent or better as the original ACCase resistant line ML0831265-01493.

FIGS. 3A-3D are photographs of (FIG. 3A) Plot 70025, ML0831266-03093F2-2(2)A-1(1)A-P-USP-USA (HPPDi+ HPPDni), Callisto, 2 applications, Preemergence/Preflood 210/210 grai/ha; (FIG. 3B) 15SAT1, Plot 03, 1×1×, RTA1, 2 applications, 2-leaf and preflood, 77+77 grai/ha (FIG. 3C); 15SAT1, Plot 12, 1×1×RTA2, 2 applications, 2 leaf and preflood, 77+77 grai/ha; and (FIG. 3D) 15SAT1, Plot 12, 1×1×RTA1-RTA2, 2 applications, 2-leaf and preflood, 77+77 grai/ha.

FIG. 4 is a graphical representation of results of a trait tolerance trial wherein mesotrione was applied at the indicated rates about 34 days after planting. (initiating tillering) the rice was evaluated for the percent of injury or damage as compared to unsprayed rice four weeks after herbicide application; the HPPD tolerant line ML0831266-03093 and the line with combined HPPD and ACCase tolerance PL1214418M2-73009 show a similar response indicating the full HPPD tolerance was recovered in the new line; the line PL1214418M2-73001 was selected to only carry the HPPD tolerant mutation from the HPPD line ML0831266-03093 and the line PL1214418M2-73013 was selected to only carry the HPPD non-induced tolerance from the HPPD line ML0831266-03093; P1003 is the non-mutant parent line for the HPPD tolerant line ML0831266-03093; note that over 420 gmai/ha, even the lines with genetic resistance may be injured.

FIGS. 5A and 5B are photographs of results of trait tolerance trials; weed control by mesotrione herbicide applied pre-planting was evaluated; the plots were planted with a hybrid of the HPPD tolerant line ML0831266-03093; just before planting, the plot on the right FIG. 5B received an application of mesotrione at 210 gmai/ha; the plot on the left FIG. 5A had no herbicide applied either pre-plant or post-emergence; pictures were taken four weeks after planting showing differences in weed appearance.

FIG. 6 is a graphical representation of results of a trait tolerance trial quizalofop was applied at the indicated rates about 30 days after planting (3-4 leaf stage), and a second application was applied on the two indicated treatments. The rice was evaluated for the percent of injury or damage as compared to unsprayed rice twenty-one days after the first herbicide application; line ML0831265-01493 is the ACCase tolerant line with the RTA1 mutation; line ML0831265-02283 is also tolerant to ACCase herbicides however the tolerance is not from a mutation in the ACCase coding gene, R0146 is the parent line for both of the ACCase tolerant lines; P1003 is a control line.

FIG. 7 shows results of a trait mapping experiment for RTA2; an F2 population was derived from a cross between a cytoplasmic male sterile line A0109 and the ACCase tolerant line ML0831265-02283; the F2 individuals in the population were genotyped, sprayed with quizalofop (116 gmai/ha) twenty-six days after planting, and evaluated for tolerance to quizalofop nineteen days after herbicide application; using QTL mapping software, a major QTL for tolerance was identified on chromosome one (indicated by the arrow).

FIG. 8 is a scattergram showing results of a mutation mapping experiment for RTA2; an F2 population was derived from a cross between the ACCase tolerant line ML0831265-02283 and the parent line R0146; the F2 population was genotyped, sprayed with quizalofop (116 gmai/ha), and evaluated for resistance to quizalofop; only mutations including ACCase resistant mutations will be segregating in the population; the SNP index is a measure of the proportion of sequencing reads that carry a variation from the non-mutant line R0146; a score of one indicates that all sequencing reads had the variation; 19 variations (mutations) had an index of one and grouped together on chromosome one (circled) indicating the probable location of the tolerance causing mutations (SEQ ID NOS: 9-27).

FIG. 9 graphically represents results of trait mapping experiments; an F2 population was derived from a cross between the HPPD tolerant line ML0831266-03093 (HPPDi induced) and the ACCase tolerant line ML0831265-01493; the population was genotyped, sprayed with mesotrione at 105 gmai/ha, evaluated for tolerance to mesotrione, and sprayed again with mesotrione at 630 gmai/ha, and evaluated for tolerance to mesotrione; only plants inheriting the mutation for tolerance from parent line ML0831266-03093 were expected to live; using QTL mapping software a major QTL for tolerance was identified on chromosome one (indicated by the arrow) (X axis—chromosome number in the genome; Y-axis=score, correlation with phenotype) (mutation mapping, chromosome 1).

FIG. 10 shows results of mutation mapping experiments; an F2 population was derived from a cross between the HPPD tolerant line ML0831266-03093 and the parent line P1003; the population was genotyped, sprayed with mesotrione at 840 gmai/ha and evaluated for tolerance to mesotrione; only mutations including the HPPD tolerant mutation segregate in the population; the SNP index is a measure of the proportion of sequencing reads that carry a variation from the line P1003; a score of one indicates that all sequencing reads had the variation; ten variations (mutations) had an index of one and grouped together on chromosome one (circled) indicating the probable location of the tolerance causing mutation (SEQ ID NOS: 28-37).

FIG. 11 is a tabular representation of segregants identified in a F4 population; the F4 population was derived from F2 selections carrying both HPPD and ACCase tolerance from a cross between the HPPD tolerant line ML0831266-03093 and the ACCase tolerant line ML0831265-01493; each row represents a different line and each column is a molecular marker within the QTL for the HPPD tolerant mutation on chromosome 1; observing the tolerance level of these lines to the HPPD herbicide mesotrione allows the tolerance mutation to be mapped to a specific gene.

FIG. 12A and FIG. 12B illustrates rate response of the mutant line ML0831266-03093, the unmutated original (parental) line P1003, and a different type of rice R0146; mesotrione was applied across all plots immediately following planting at a rate of 210 gai/ha; the response rates were applied at the 2-3 leaf stage; response was recorded twenty-one days following the foliar application. FIG. 12A=initial results and FIG. 12B=subsequent results.

FIG. 13 shows a DNA sequence for the carboxyl transferase coding region in the ACCase coding gene; a single nucleotide change (box) that encodes a mutation from RTA1 is identified in the mutant line ML0831265-01493 which is designated as 09PM72399 (SEQ ID NO: 3). NIPPONBARE is a control (SEQ ID NO: 1); R0146 (SEQ ID NO: 2) is the original line treated with a mitogen to produce a mutation population.

FIG. 14 shows comparison of protein sequences for the carboxyl transferase region of the ACCase gene; the line with code 09PM72399 (SEQ ID NO: 5) is the line ML0831265-01493; this line shows a change of a single amino acid (box) at position 2096, relative to Black-Grass; R0146 (SEQ ID NO: 5) is the original line treated with a mutagen to produce a mutation population. [NIPPONBARE is SEQ ID NO: 4]

FIG. 15 shows a rate response of the mutant line ML0831266-03093, the unmutated original line P1003, and a different type of rice R0146. Mesotrione was applied across all plots immediately following planting at a rate of 210 gai/ha. The response rates were applied at the 2-3 leaf stage. Response was recorded twenty-one days following the foliar application.

FIG. 17C 2 leaf only-Quizalofop 0.5×.

Figure 19:
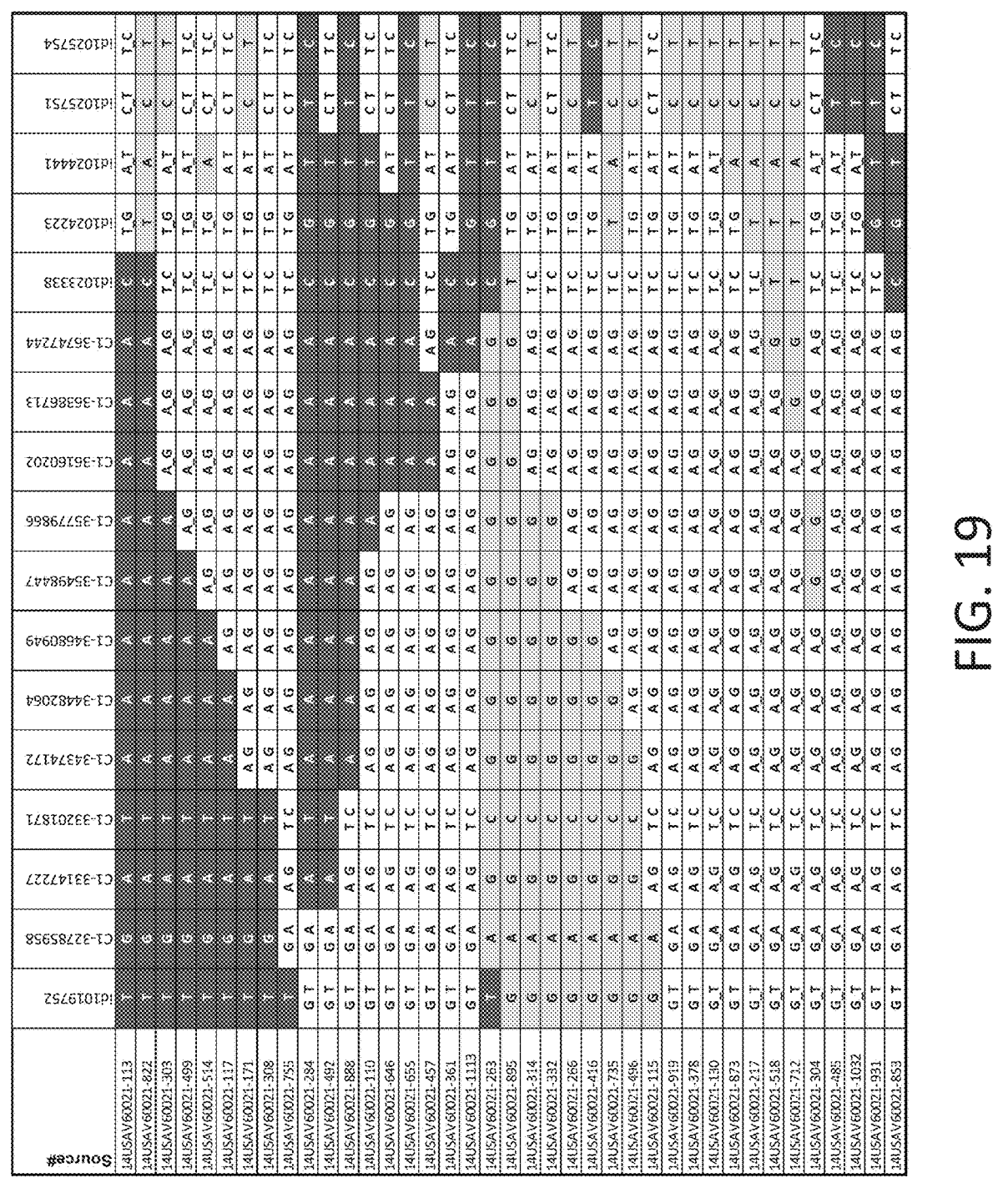

FIG. 19 shows advanced sub-recombinant F4 lines that were identified within a large F3 population to enable fine mapping of the mapped mutations and to identify the causal one that is associated with RTA2 herbicide resistance. Challenging these F3 plants with 1× Quizalofop dose to which heterozygous plants showed increased injury relative to homozygous mutant plants, allowed an initial fine-mapping narrowing the likely position of the causal mutation. Subsequently, F4-derived families were rescreened with the same herbicide/dose to identify a causal mutation determined to be Chr1QMM36160202_G-A.

Figure 20C:
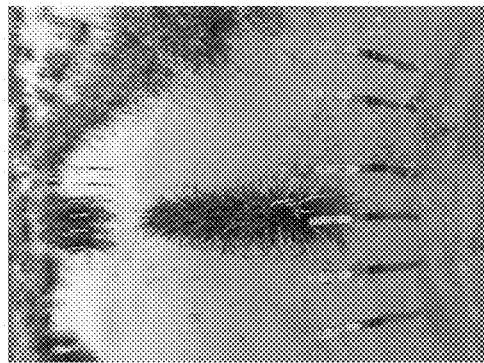
Figure 20B:
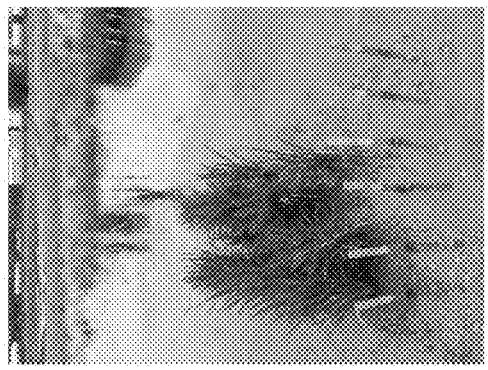
Figure 20A:
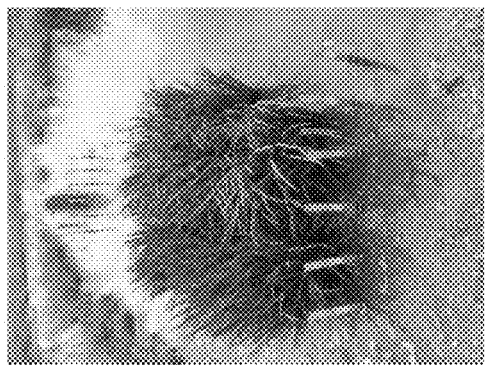
Figure 20D:
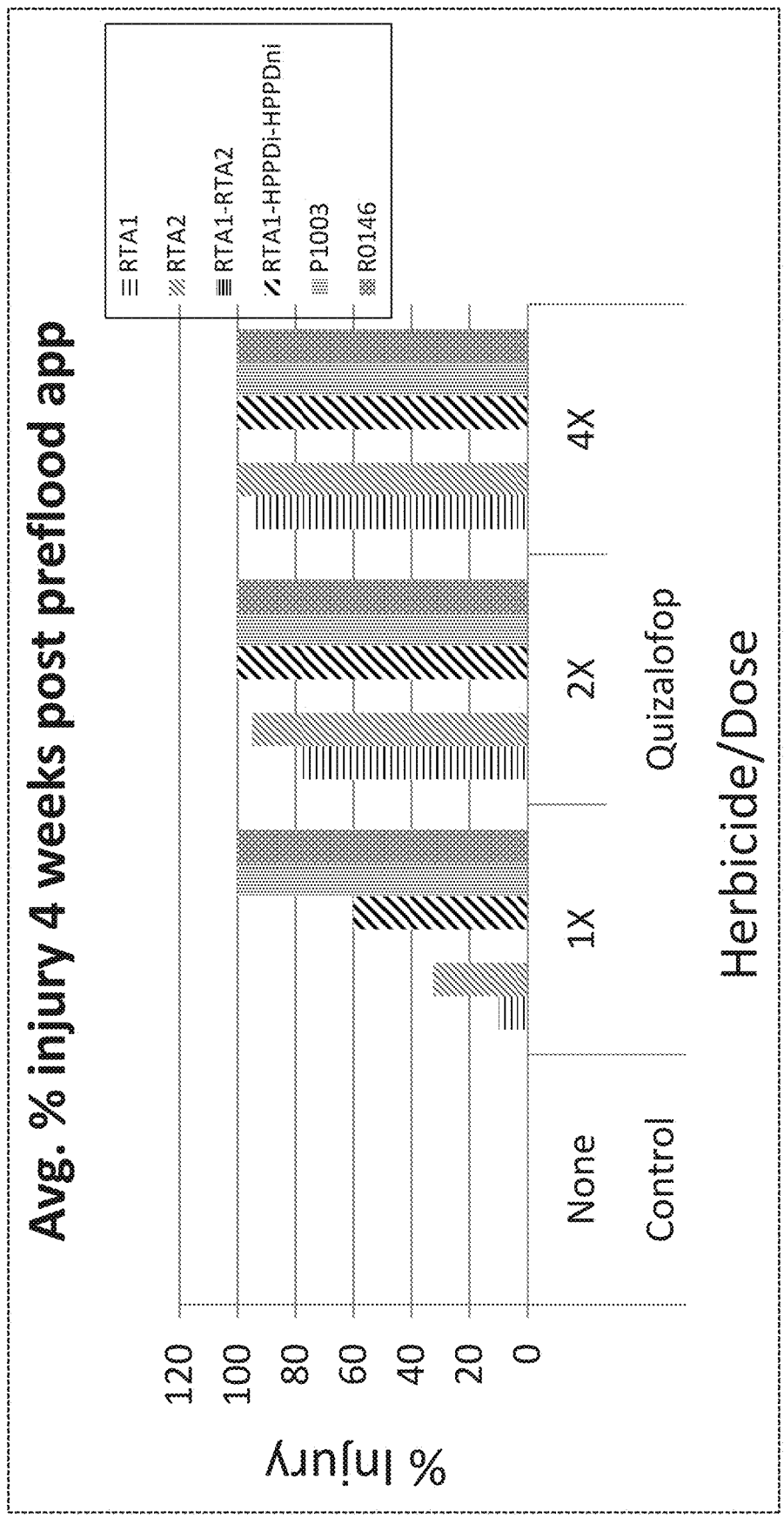

FIG. 20A-FIG. 20D showing % Injury response data and plot pictures. Material tested included ACCase-inhibitor resistant combined ACCase lines (RTA1+RTA2), the RTA1 and the RTA2 singles and the stack RTA1+HPPDi+HPPDni. Two applications (at the 2 leaf and pre-flood stage) used the same rate for both applications. The ACCase stack shows no injury 4 weeks post preflood application even at 4× label rate of Quizalofop. This combination of traits is significantly more tolerant of Quizalofop application than either single ACCase tolerance mutant alone. FIG. 20A control plot, FIG. 20B 1× Quizalofop, FIG. 20C 4× Quizalofop plot with only ACCase combined line surviving. (all images taken 4 weeks post preflood app), FIG. 20D Plat order (left to right) RTA1, RTA2, RTA1+RTA2, RTA1+HPPD i+HPPDni, P1003, R0146. Summary: ACCase combined line (G2096S+RTA2 1) shows no injury 4 weeks post preflood application even at 4× label rate of Quizalofop.

Figure 21E:
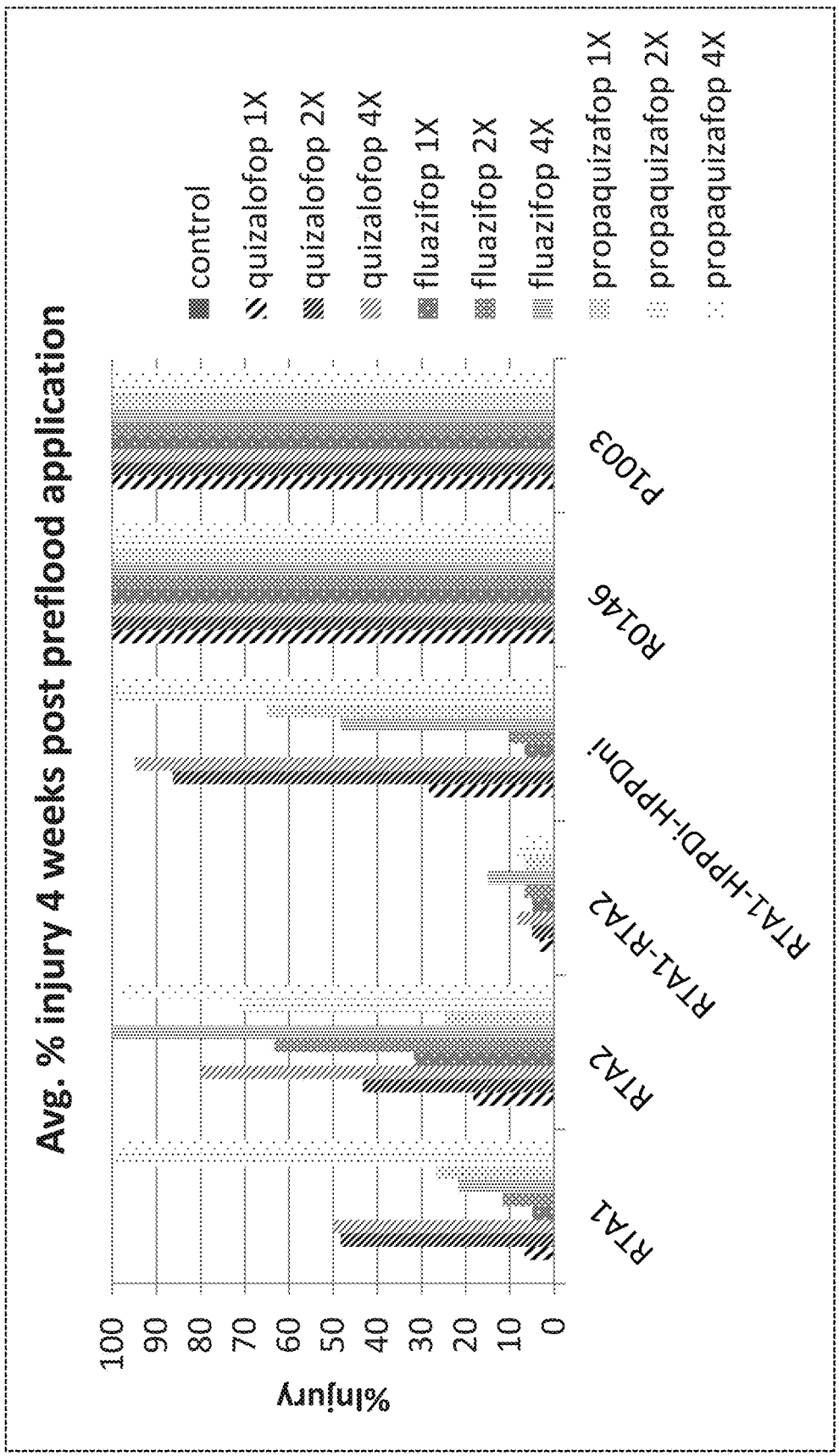

FIG. 21A-FIG. 21E, show plot pictures and % Injury response for ACCase lines RTA1, RTA2, and the stacks RTA1+RTA2 as well as the stack RTA2+HPPDi+HPPDni, when challenged by increasing doses of the main FOP herbicides. ACCase inhibitor resistant combined lines (RTA1+RTA2) shows significantly less injury than single mutant lines 4 weeks post preflood application at higher application rates of all FOP herbicides tested. While injury in the ACCase combined mutation line was slightly higher to Quizalofop in this trial than previous trials, the injury is minimal even at high application rates. Differences between levels of tolerance amongst the trait combinations tested become much more apparent when applying higher rates. Propaquizafop continues to cause the highest rates of injury across all trait combinations. Fluazifop at rates of 2× or less seems viable with any trait combination containing RTA1, but at 4× only the combined ACCase line shows minimal injury. FIG. 21A untreated control, FIG. 21B 4× Quizalofop, FIG. 21C 4× Fluazifop, FIG. 21D 4× Propaquizafop. 4 weeks post preflood application. Plot order (left to right) G2096S, RTA2, G2096S+RTA2, G2096S+HPPD, P1003, R0146. FIG. 21E graphical representation.

Figure 22D:
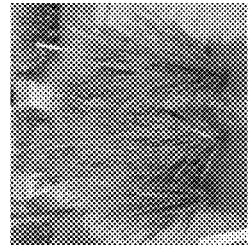
Figure 22H:
Figures 22A, 22E:
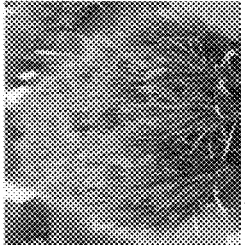
Figure 22C:
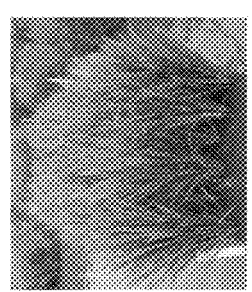
Figure 22G:
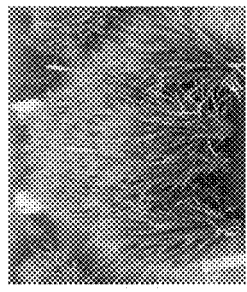
Figure 22B:
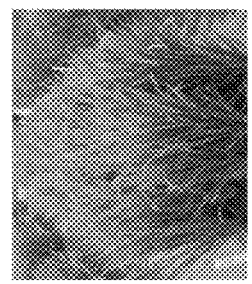
Figure 22F:
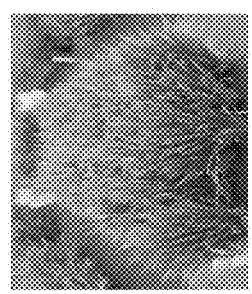

FIGS. 22A-22D shows L to R; RTA1; FIG. 22A Control, FIG. 22B Quizalofop 1×, FIG. 22C Quizalofop 2×, and FIG. 22D Quizalofop 4×; FIG. 22E-FIG. 22H shows RTA1-RTA2; FIG. 22E Control, FIG. 22F Quizalofop 1×, FIG. 22G Quizalofop 2×, and FIG. 22H Quizalofop 4×. Images 9 weeks post preflood application.

Figure 23:
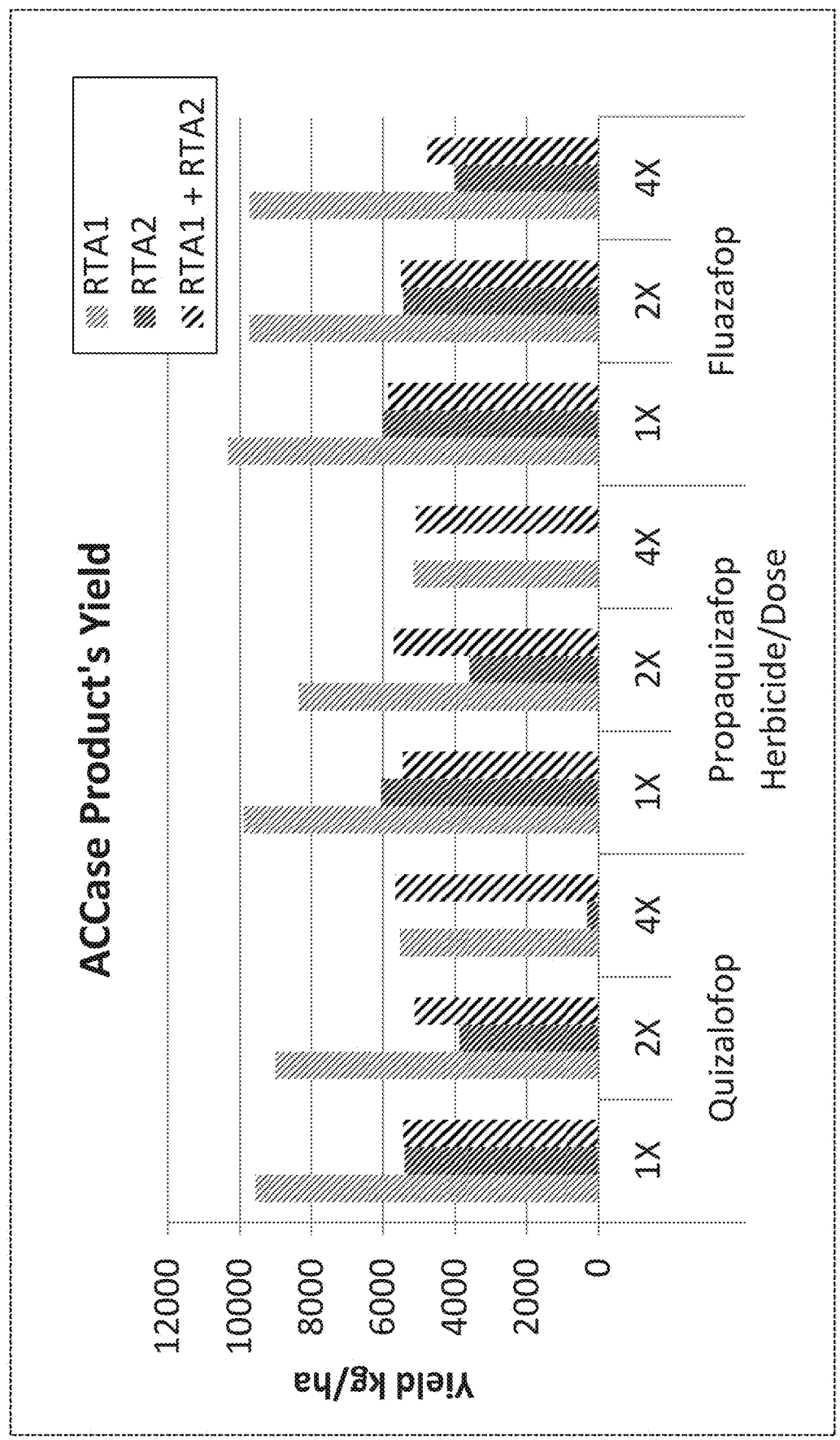

FIG. 23 shows the Yield response for the ACCase products RTA1, RTA2 and RTA1+RTA2 mutated lines, when challenged with different herbicides of the ACCase-Inhibitors FOP family Quizalofop, Fluazifop and Propaquizafop. Yield response after sequential 2-leaf and pre-flood quizalofop application.

Figure 24:
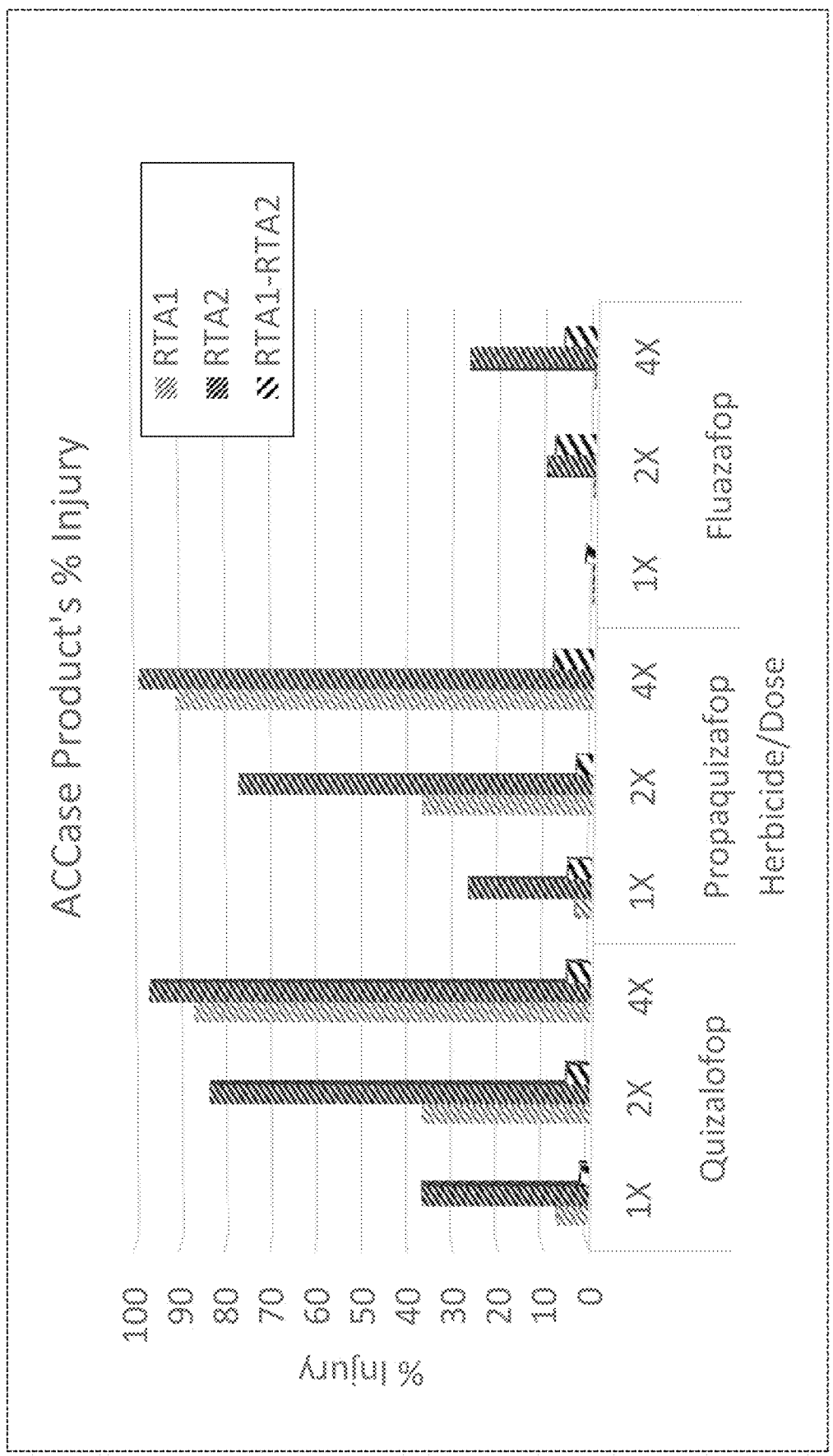

FIG. 24 shows the % Injury response and for the ACCase products RTA1, RTA2 and RTA1+RTA2 mutated lines, when challenged with different herbicides of the ACCase-Inhibitors FOP family quizalofop, fluazifop and propaquizafop after sequential and pre-flood.

Figure 25:
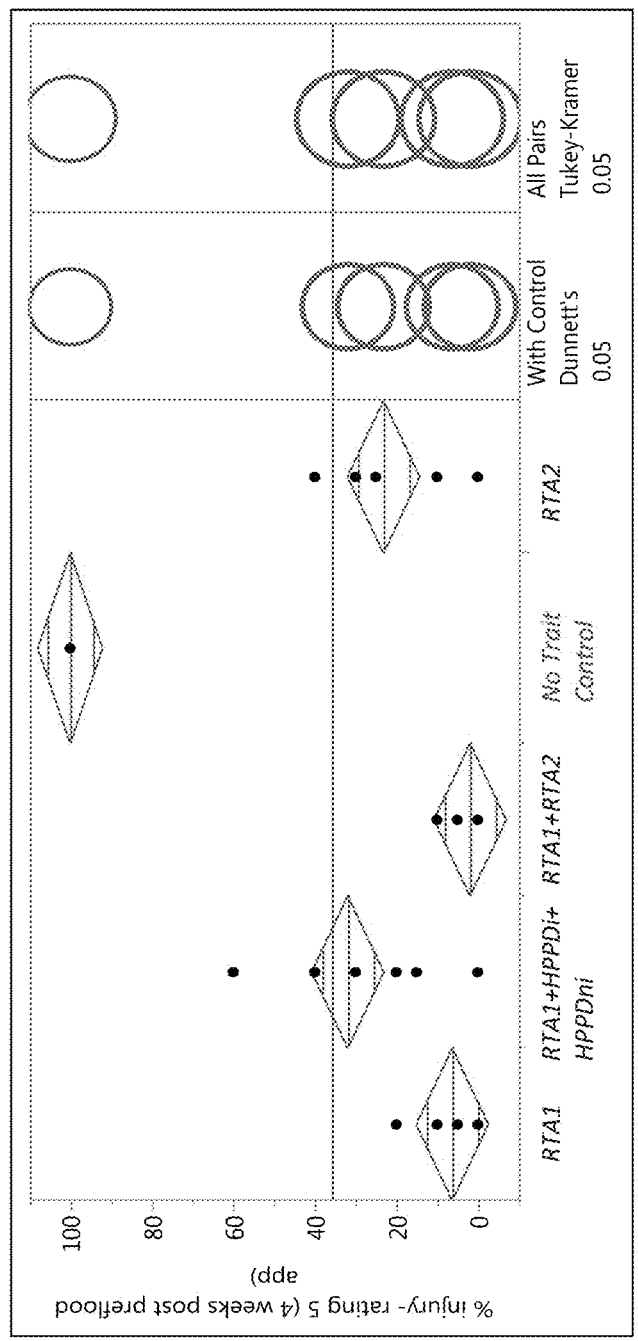

FIG. 25 presents summary statistics and mean comparisons for % injury, for 1× quizalofop application on ACCase products; Oneway analysis of % injury-rating 5 (4 weeks post preflood app) by trait, 2-leaf herbicide rate (multiple of label)=1×.

Figure 26:
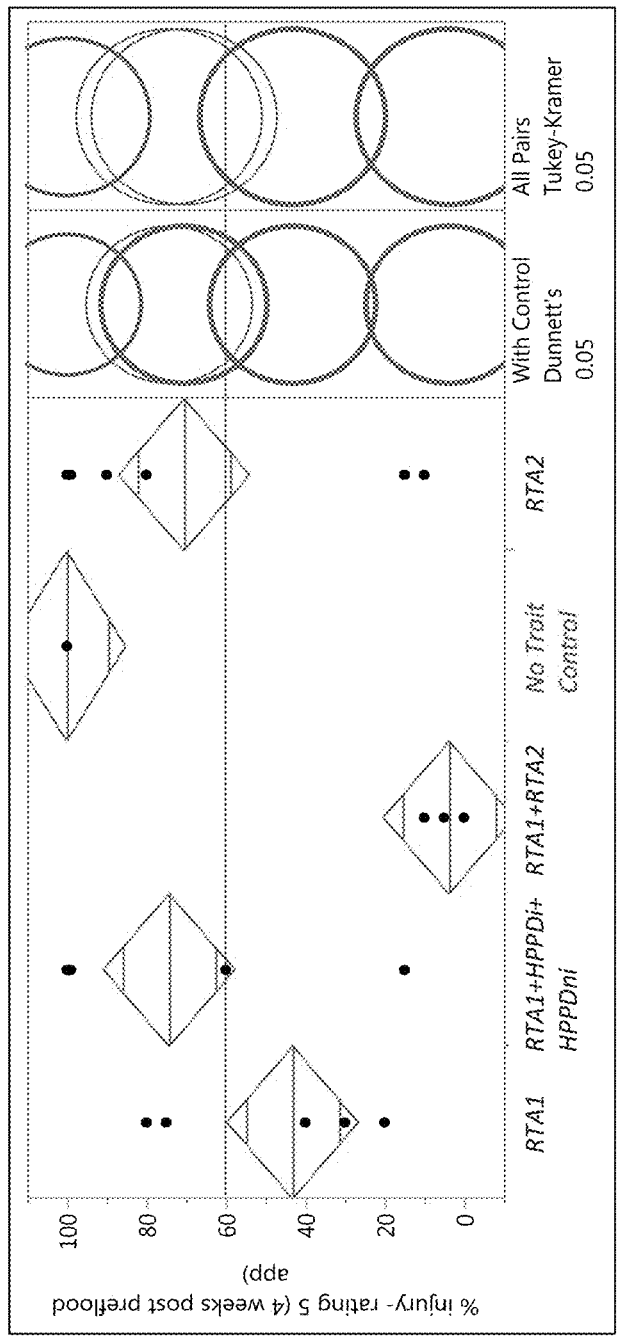

FIG. 26 presents summary statistics and mean comparisons for % injury, for 2× quizalofop application on ACCase products; Oneway analysis of % injury-rating 5 (4 weeks post preflood app) by trait, 2-leaf herbicide rate (multiple of label)=2×.

Figure 27:
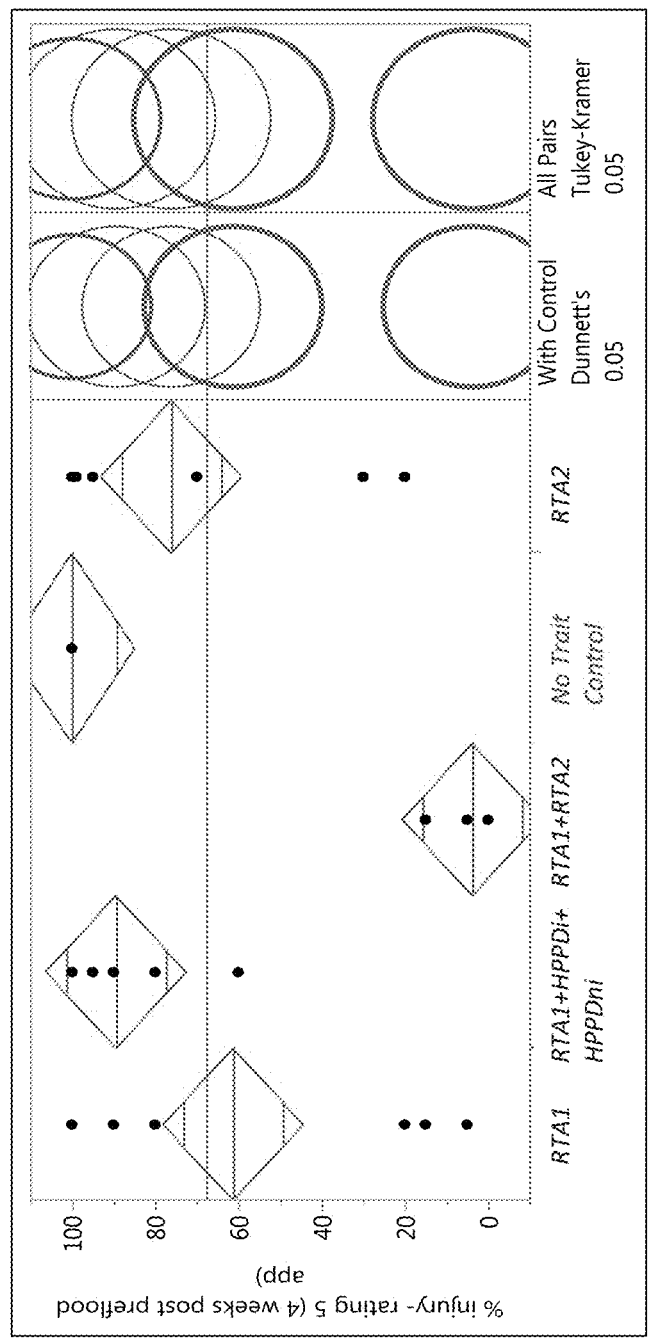

FIG. 27 presents summary statistics and mean comparisons for % injury, for 4× quizalofop application on ACCase products; Oneway analysis of % injury-rating 5 (4 weeks post preflood app) by trait, 2-leaf herbicide rate (multiple of label)=4×.

DETAILED DESCRIPTION

1. Synergistic ACCase Inhibitor Resistance/Tolerance

Internal-mutagenized population screening at RiceTec, for FOP herbicides, allowed the identification of two mutagenized chromosomal regions, RTA1 and RTA2, that independently conferred tolerance to these herbicides. Each of these independently derived mutant tolerant lines were advanced and evaluated after the initial screening, to further characterize these new variants, assess their tolerance effect, determine the causal mutation or mutations responsible for the new phenotypes and to assess their commercial potential. Completion of these studies required several generations of population advancement and experimentation. These studies included, as main objectives, DNA Marker linkage/QTL mapping of the phenotype to pinpoint chromosomal position; gene action studies; dose, timing of application and herbicides studies to assess product specification and value and also whole genome sequencing/mutation mapping analysis to characterize the mutations associated to these phenotypes. Further studies involving stacking of these two mutation in single genetic backgrounds were also conducted to assess the interaction between these independently developed mutants and their potential antagonistic or synergistic effect in FOP herbicide tolerance.

The mutated tolerance gene RTA1, was found to map exactly to the location of the known target gene for this family of herbicides the interfere with lipid biosynthesis, the Acetyl CoA enzyme locus, in what clearly represents a target site resistance (TSR) occurrence. In TSR typically, the mutated allele has a modification that conditions an amino acid change in the expressed protein that interferes, or blocks, the normal interaction with the herbicide thereby preventing, or limiting, the expression of phytotoxicity. RTA1 was later determined, though mutation mapping analysis, to be a single point mutation in the DNA of the ACCase gene whereby a Guanine nucleotide in the wild type is replaced by an Adenine in the mutant, resulting in change in amino acid (G to S) in the expressed protein at one of the critical binding sites where Acetyl-coA and FOP herbicides interact to onset phytotoxicity. This change at a critical binding site in the ACCase enzyme (found in chloroplasts), reduced affinity to the herbicide, preventing blockage of ACCase activity and phytotoxicity. Thus plants carrying the mutation do not die by the herbicide. The mutation was identified by sequence and exactly matches identical FOP-tolerance mutations identified in homologous positions in other crops, for the same ACCase gene.

In the case of RTA2, the mutation or mutations associated with tolerance are located on Chromosome 1, as shown by linkage/QTL analysis and by sequencing-mutation mapping. Because in this region of rice (Chromosome 1) there are no reports of duplicated or orthologous ACCase or ACCase-like genes, target gene of the FOP herbicides, it is assumed that RTA2 represents a case of non-target site resistance (NTSR).

Embodiments of mutant rice lines designated ML0831265-01493 (ATCC deposit PTA-12933, mutation G2096S, henceforth referred to as "RTA1") and ML0831265-02283 (ATCC deposit PTA-13619 ("RTA2")) are resistant/tolerant to ACCase inhibitors singly or in combination. (U.S. Pat. No. 9,370,149 B2).

Table 1A and 1B present the sequence and genetic information for the region in RTA2 associated with herbicide resistance. This region in combination with RTA1 (G2096S) confers synergistic almost independent resistance to FOP herbicide. The overlapping of results obtained from herbicide tolerance effect mapping and F3-4 recombinant fine mapping, with the mutation mapping, identified the above listed 26 mutations, contrasting with both O. sativa (ssp indica), and O. sativa (ssp japonica) sequence references, as the putative causal factors in RTA2 non-target site herbicide tolerance.

A vector of closely linked mutations in chromosome 1 is associated with synergistic action effecting herbicide tolerance when combined with RTA1. The RTA2 mutation initially mapped to a mutation causing a change of G to A in the nucleic acid coding sequence of the gene ZOS1-16 encoding a C2H2 zinc finger protein from Oryza sativa at rice base pair position 3660202 in chromosome 1 region. This region, which is correlated with a synergistic response to ACCase inhibitors, has not been reported before in herbicide tolerant rice. No report was found of another rice region on chromosome 1 conferring resistance to quizalofop. When RTA2 is by itself in rice, there is increased resistance/tolerance to ACCase inhibitors, but the mutation operates to cause resistance/tolerance to ACCase inhibitors best when combined with rice that also expresses the RTA1 mutation.

Because the specific levels of herbicide tolerance of RTA1 and RTA2 plants separately were moderate or low, as previously stated, crosses were made between RTA1 and RTA2 mutant lines to produce a stacked combination of both mechanisms and possible interactions between the novel genetic combination were sought. The end stacked product was rapidly obtained by simple Marker Assisted Selection (MAS) for the chromosome 1 resistant haplotype using markers C1-3208396 and C1-36386713, and using markers for the ACCAse locus in chromosome 5. Experiments of herbicide dose, timing of application and active ingredient, conducted on the RTA1-RTA2 double homozygous line revealed that there exists a very strong synergistic effect between the two independent tolerance variants, whereby the double homozygous mutant tolerates, at the critical early window of desirable application (2-leaf stage), a maximum dose of 80 oz/acre, of Quizalofop with no phytotoxicity, effectively providing near dose-independent tolerance, whereby most reported induced or spontaneous ACCase mutants only tolerate field dose applications.

Stacking of both genetic mutations is exemplified by seeds deposited in the ATCC PTA-122646 (RL-122546-8). Synergistic resistance to ACCase inhibitor was observed in rice with the stacked mutation.

The difference between a "stacked mutant donor" and a "conversion" (Table 9) is that RTA1 and RTA2 are identified independently from the same R0146 mutagenized population. With the intent of evaluating potential synergistic effects between the two independent loci, homozygous RTA1 and RTA2 lines were intercrossed at the F5 level, and F2 progeny carrying both homozygous herbicide tolerant mutations were selected to create the double RTA1-RTA2 stacked donor RL1225468 (PTA-122646).

Stacked donor RL1225468, being an intercross of F5 lines derived from the original mutant populations, carries random mutations across the entire genome. In order to develop a "clean" donor carrying only wild type R0146 alleles throughout the genome, except at the Chr5 ACCase RTA1 locus and the Chr1 RTA2 locus, a backrcross program was conducted to transfer the mutated alleles into a conventional R0146 line. Line 16USGE40004-34, is a BC3F3 selection from the original cross RL1225468/R0146, backcrossed to R0146 three times, and filed with ATCC under PTA-124233. The synergism was present in use of both genetic backgrounds.

It is a surprising and unexpected result to find herbicide resistance/tolerance effected by a combination of a mutation in a target enzyme, disclosed herein RTA1, with RTA2 mutations in a NTSR. Based on sequence analysis, ACCase gene is located on Chromosome 5 in rice. Part of the gene is duplicated on Chromosome 10, but no part of the ACCase gene is reported on Chromosome 1.

Compared with TSR, in which the herbicide resistance mechanism is directly associated with variation in the known target protein/gene, whereby the metabolism of resistance is clearly inferred, as with RTA1, NTSR mechanisms are much more difficult to characterize, and require extensive gene, gene action, and gene interaction studies.

It is postulated that NTSR for FOP herbicides, could arise from onset of mechanisms triggering metabolic resistance such as compartmentalization, blockage of movement, detoxification, blockage of activation or other forms of preventing phytotoxicity. Also, recent studies showed that microRNAs (miRNAs) can be involved in the 'gene regulation' mechanisms leading to NTSR. In general, NTSR mechanisms and the molecular interaction involving the herbicide are more complex mechanisms than found in TSR.

Possible mechanisms explaining the synergistic effects of plants carrying the RTA1 mutation and RTA2 region include breaking down the herbicide by biochemical processes (detoxifying the herbicide), or by limiting the translocation of the herbicide to chloroplast, (compartmentalization) or other metabolic functions preventing herbicides affected the ACCase enzyme. Detoxifying the herbicide or indirectly acting as a 'regulator' in activating genes involved in cell protection like Cytochrome P450 mono-oxygenase, glutathione transferases, aryl acylamidiases or others, are NTSR mechanisms.

There were significant benefits in stacking the RTA1 and the previously "ACCase Unknown" mutation (now called RTA2), because of synergism in resistance/tolerance of the rice with both mutations in their genome.

The benefits of the double mutations are illustrated in FIGS. 20, 21, 22, 23, and 24.

Table 7 lists criteria for categorizing % injury in the plant sprayed (contacted) with a herbicide.

2. Identification of the Causal Mutation for Tolerance to ACCase Herbicides in Line ML0831265-02283 (RTA2)

Often tolerance to ACCase herbicides is derived from a mutation in the carboxyl transferase region of the ACCase gene, as is the case in tolerant line ML0831265-01493 (mutation G2096S or RTA1). However after sequencing the carboxyl transferase region of the ACCase gene in line ML0831265-02283 no mutation was found. This result indicates that the tolerance in line ML0831265-02283 is derived from a non-target site process.

Finding the causal mutation for tolerance in line ML0831265-02283 involved linkage mapping and mutation mapping as ("mut mapping") described for finding the causal mutation and native tolerance for HPPD tolerance in line ML0831266-03093.

Figure 9:
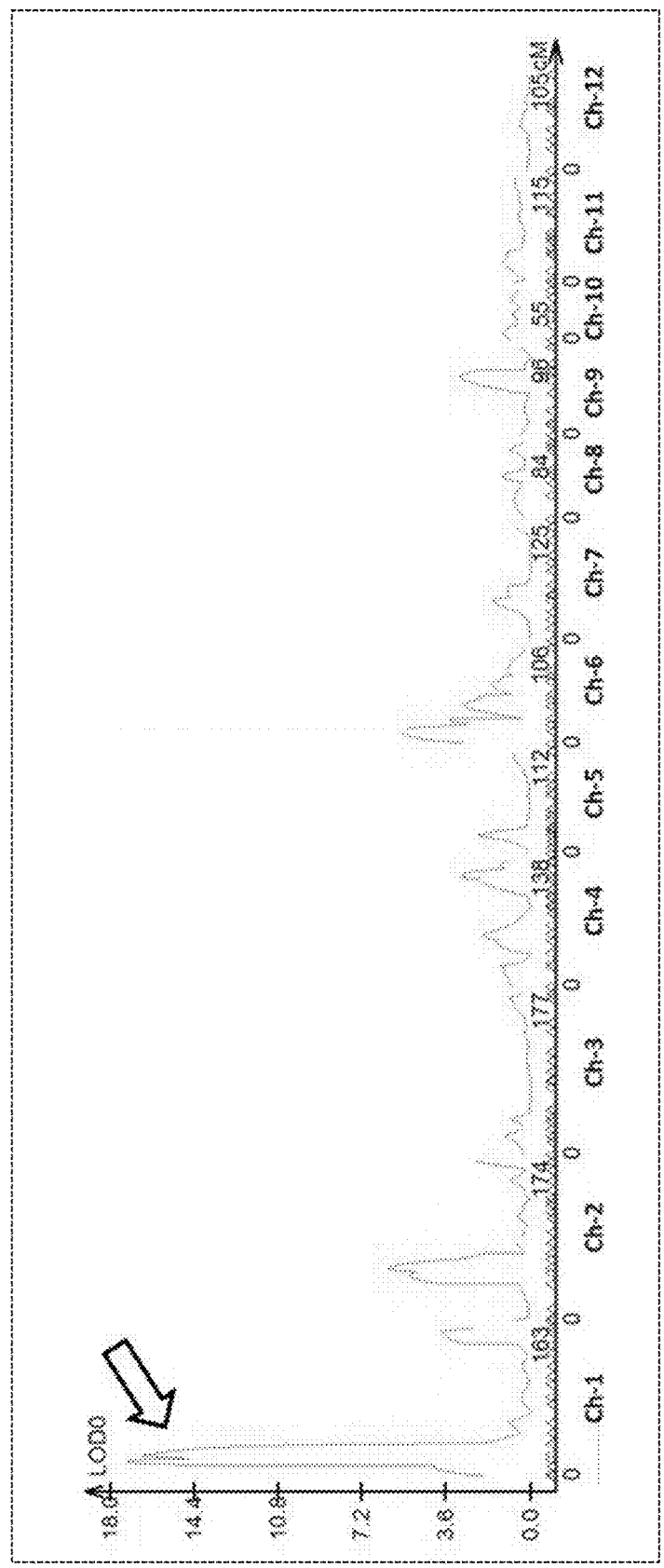

Linkage mapping to find the chromosomal region or QTL causing the tolerance in line ML0831265-02283 requires a population segregating for the trait. This population was made by crossing the tolerant line with the male sterile cytoplasm line A0109. The F1 collected from this cross was grown and allowed to self-pollinate to make a F2 population. The F2 population segregated for ACCase tolerance. Eight hundred F2 seeds were planted and leaf tissue was collected from the seedlings to allow genotyping of each plant. When the seedlings where three weeks old the whole F2 population was sprayed with quizalfop (116 gmai/ha). The seedlings were evaluated for tolerance nineteen days after the herbicide application. Standard QTL mapping software was used to analyze the genotypes of each F2 individual and the associated tolerance response to identify molecular markers linked to the herbicide tolerance. After this analysis a genomic region (QTL) was identified for the tolerance on chromosome one (FIG. 9). Linked markers flanking the QTL and markers inside the QTL flanking the peak of the QTL were identified as being suitable to select the herbicide tolerance derived from line ML0831265-02283. Approximately 250 genes are between the flanking markers.

The mutation mapping strategy to find the causal mutation was employed in the same manner as used to find the QTL for HPPD mutation tolerance. A mutation mapping population was created to find the causal tolerance mutation through genomic sequencing by next-generation sequencing. The mutant line ML0831265-02283 was crossed back to the original non-mutant parent R0146. The F1 progeny of the cross were selfed to produce a F2 population that is segregating for the tolerance causing mutation. Only mutations are segregating in this population because the mutations are the only genomic difference between ML0831265-02283 and R0146.

The F2 population was planted as individuals, and leaf tissue was collected and DNA extracted from each individual to use for genotyping after the population was phenotyped. The ACCase herbicide quizalofop was applied to the F2 population at the 3-4 leaf stage and a concentration of 116 gmai/ha. Individuals that survived the herbicide application were scored as tolerant and those that died were scored as susceptible.

The DNA derived from a set of twenty surviving F2 individuals and twenty that were killed was each respectively bulked together and sequenced along with both the mutant line ML0831265-02283 and the non-mutant parent line R0146. Mapping the causal mutation was based on an index accessing the frequency of all mutations in the bulk representing the surviving individuals. The index was derived from the proportion of sequencing reads that carried a variation different from the non-mutant parent line R0146. The more sequencing reads with the variation the closer the index was to one and if all sequencing reads had the variation the index equaled one.

Figure 10:
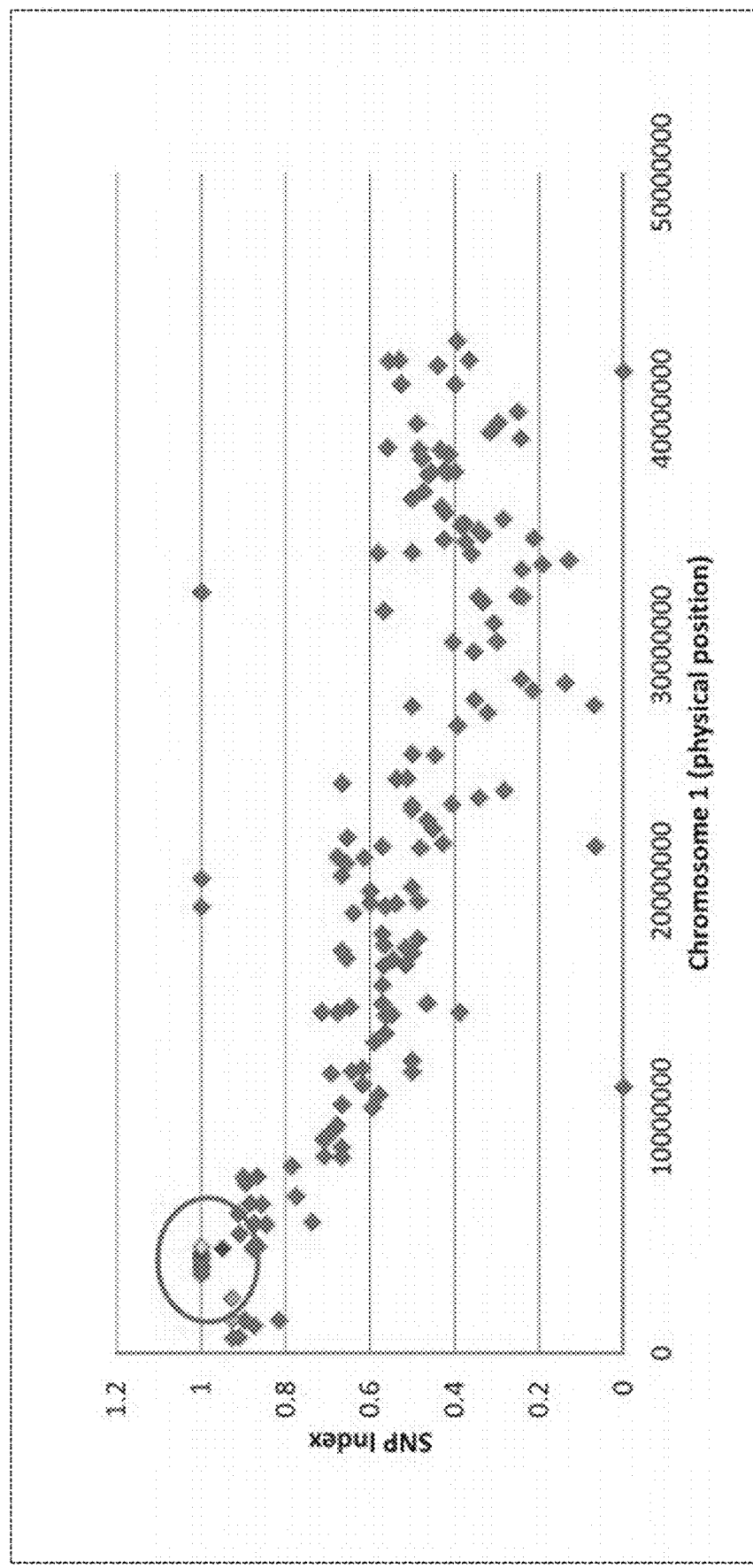

The analysis of these results showed two groups including 19 mutations of eleven mutations on chromosome one with an index score of one (FIG. 10). This result confirms the QTL linkage mapping results as the mutations identified here all are located within the QTL region identified on chromosome one by linkage mapping. Molecular markers (SNP) were made for each of the mutations (Table 4). These markers were used in fine mapping to find the causal mutation and for breeding the ACCase tolerance derived from line ML0831265-02283 into commercial rice lines.

As in previous trials, injury observed in RTA1+RTA2 is very low across all rates regardless of herbicide chemistry. FIG. 24 RTA1 showed injury consistent with previous studies with injury rates below 10% with both 1× Quizalofop and Propaquizafop, and injury rates of near 40% at 2× application rates which is slightly lower than a 2015 field average. Also as previously observed rates of injury to Fluazifop was much lower than either of the other FOP herbicides. Yield data shows good yield retention in RTA1 with both 1× and 2× application rates of Quizalofop. The higher rates of injury recorded for RTA1 at 2× Quizalofop appear to have had no negative effect on yield. RTA1+RTA2 showed a yield reduction in treated versus the untreated control plots, but the herbicide chemistry or application rate had only minimal effect on yield between treatments.

3. Mutation Mapping to Find the HPPD Tolerance Causative Mutation

Mutation Mapping analysis, using both *japonica* (Nipponbare cultivar) and indica (93-11 cultivar) reference genome sequence identified the same Chromosome 1 as associated with the novel FOP tolerance phenotype.

A mutation mapping population was created to find the tolerance causal mutation through genomic sequencing by next-generation sequencing. The mutant line ML0831266-03093 was crossed back to the original non-mutant parent P1003. The F1 progeny of the cross was selfed to produce a F2 population that will be segregating for the tolerance causing mutation. Only mutations will be segregating in this population because the mutations are the only genomic difference between ML0831266-03093 and P1003.

The F2 population was planted as individuals and leaf tissue collected and DNA extracted from each individual to use for genotyping after the population was phenotyped. In this method all of the population will carry the native tolerance gene rendering the population tolerant to a certain level to mesotrione herbicide. To differentiate the native tolerance from the tolerance causal mutation mesotrione was applied to the population with a high rate (840 gmai/ha) so that all individuals without the tolerance causal mutation died.

The DNA derived from a set of twenty surviving F2 individuals and twenty that were killed was each respectively bulked together and sequenced along with both the mutant line ML0831266-03093 and the non-mutant parent line P1003. Mapping the causal mutation was based on an index accessing the frequency of all mutations in the bulk representing the surviving individuals. The index was derived from the proportion of sequencing reads that carried a variation different from the non-mutant parent line P1003. The more sequencing reads with the variation the closer the index was to one and if all sequencing reads had the variation the index equaled one.

A single mutation causing the high tolerance to mesotrione was predicted. Instead the data showed a peak of mutations carrying a score of 1 introducing another level of difficulty in finding the causal mutation. The result did confirm that the QTL on chromosome 1 found through linkage mapping is the genomic location of the tolerance casual mutation (FIG. 10). Within the peak of mutations seven mutations with an index of one, none of which are an obvious cause for tolerance to mesotrione herbicide. Markers were developed for the mutations to facilitate finding the casual resistance mutation(s).

Figure 11:
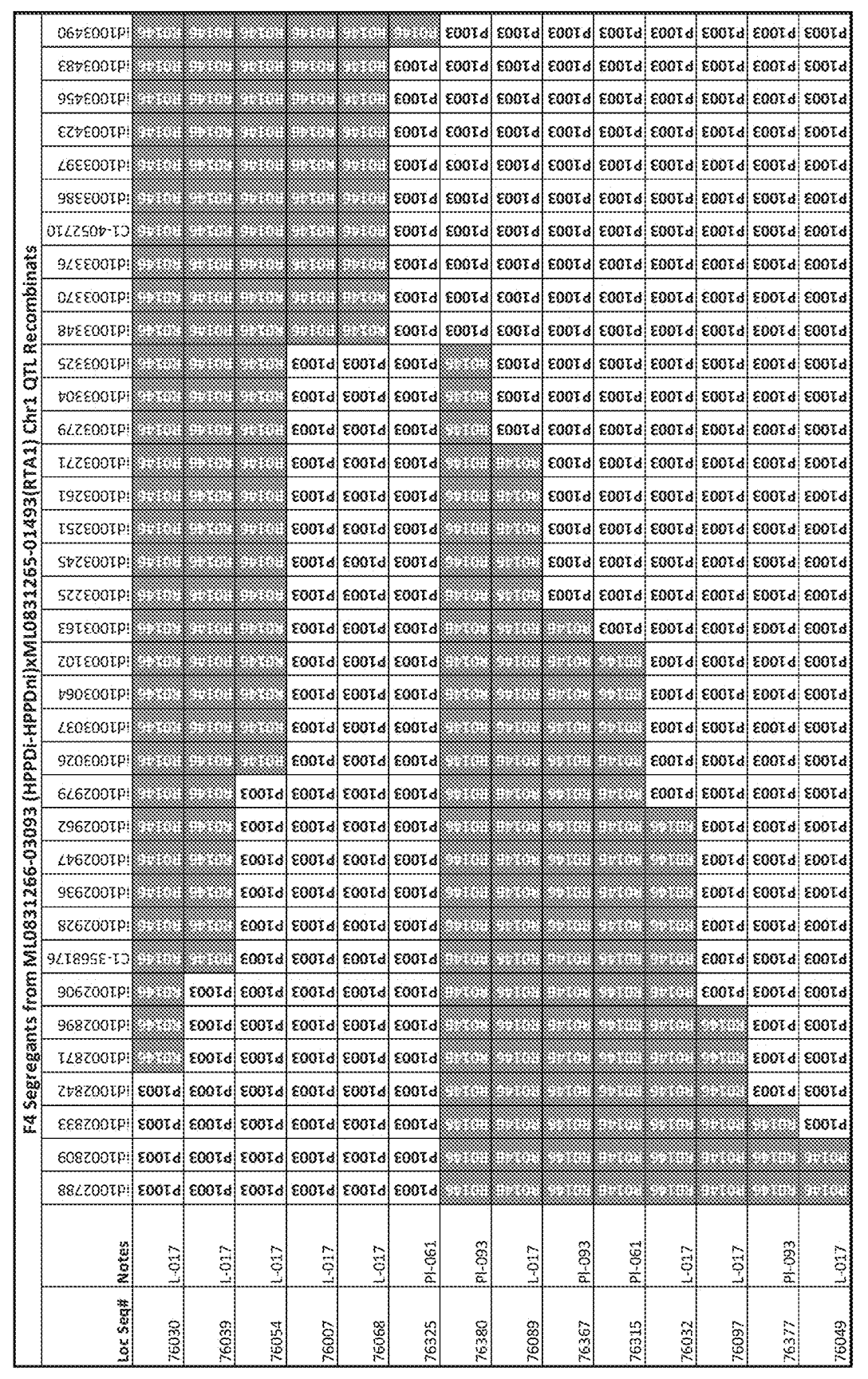

A set of lines was identified with recombination points evenly distributed within the identified QTLs and mutations (FIG. 11). These lines were recovered in a homozygous condition for each recombination allowing phenotyping for herbicide tolerance on multiple individuals (full plots). Analysis of these lines allowed the tolerance mutation and native gene to be narrowed to a small region of the chromosome.

Through the described strategy the specific genomic regions containing the tolerance causal mutation and the native tolerance gene are now known and useful for developing commercial products. The commercial products are useful in rice production as they survive application of mesotrione herbicide at rates that will control prevalent weeds including red rice without harming the rice crop. The specific genomic location allows the use of molecular markers on the flanking regions of each QTL to select for the HPPD tolerant trait in the development of commercial products.

Genetic mapping of the three groups of F2 individuals including the set of individuals sprayed with mesotrione at only 105 gm ai/ha, the set followed by a sequential application of 630 gm ai/ha, and the final group sprayed with 420 gm ai/ha shows two genes controlling resistance to mesotrione. In the population sprayed with 105 gm ai/ha a single QTL found on chromosome 2 with strong linkage to SNP marker BG-id2004662 acted in a mostly dominate manner. This marker and QTL identifies the inherent tolerance in line P1003. The marker is useful for breeding and selection of new mesotrione tolerant lines. The discovery of this QTL facilitates commercial development of new rice varieties with a new method for controlling weeds through the use of mesotrione herbicide. The finding of the linked marker BG-id2004662 is a novel finding and selection strategy for breeding and selecting the tolerance to mesotrione and other herbicides derived from line P1003.

Figure 16:
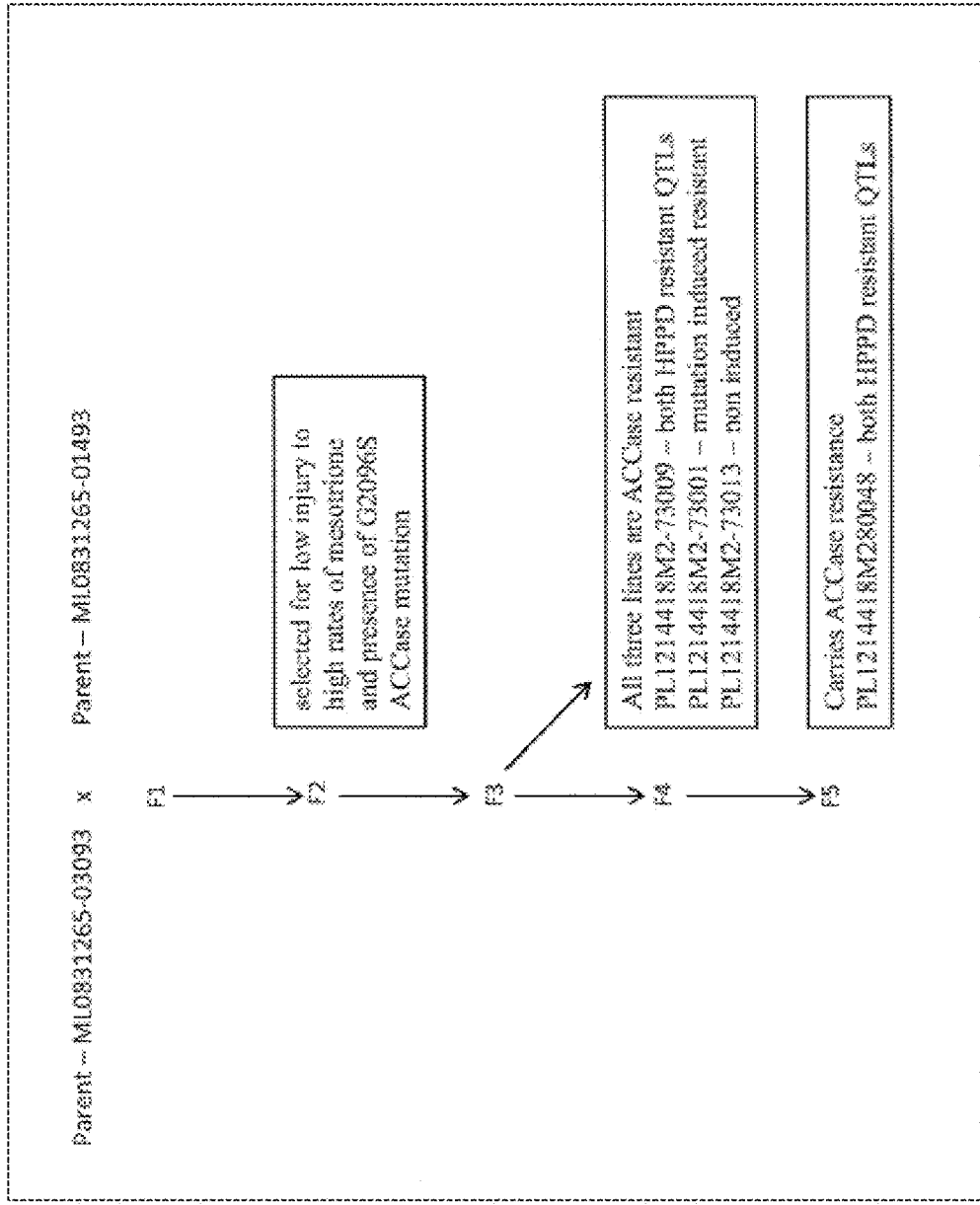
FIG. 16 is a flow chart of a type of cross used to produce herbicide resistant in some rice embodiments disclosed herein.
Figures 17A, 17B, 17C:
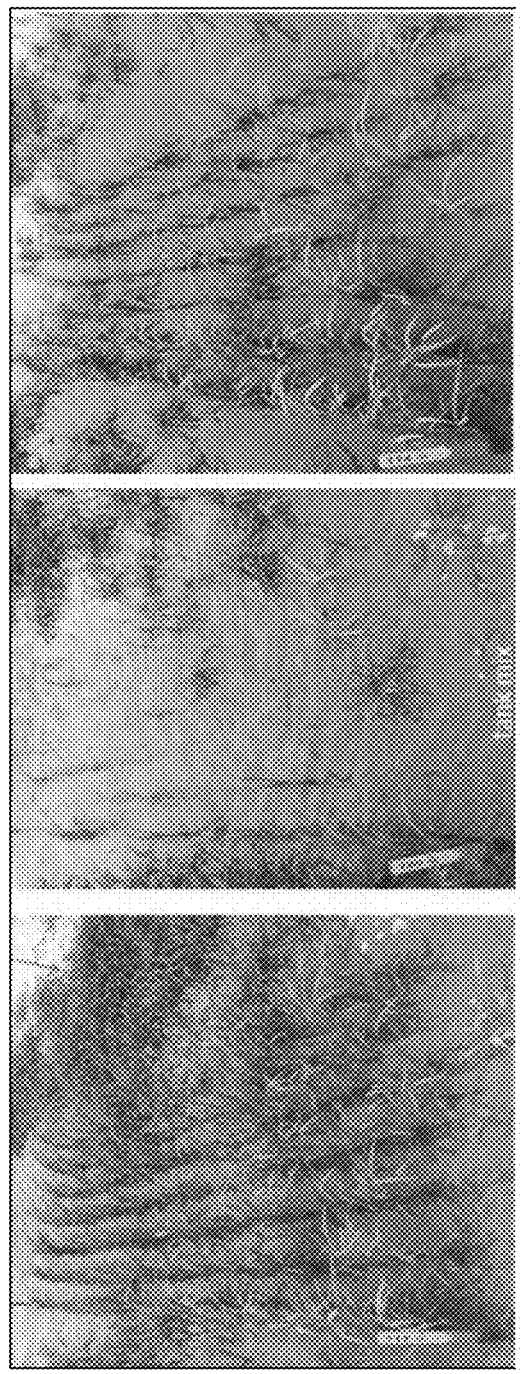
FIGS. 17A-17C are showing FIG. 17A, 2 leaf only-mesotrione 0.5×, FIG. 17B, 2 leaf only-mesotrione 0.5×/Quizalofop 0.5×.
Figure 17D:
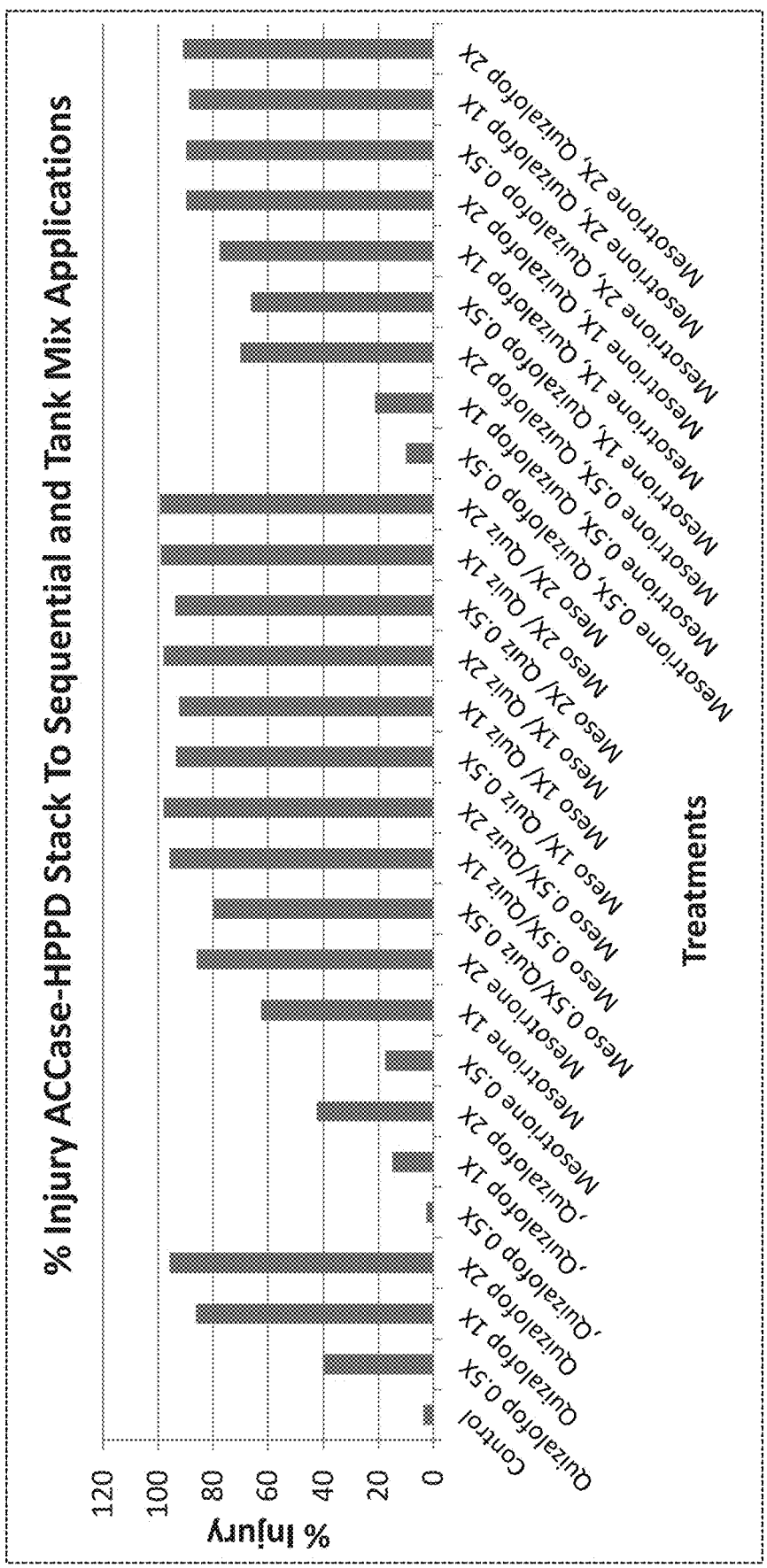
FIG. 17D are graphs representing the % injury for the response to Tank Mix versus Sequential Applications for the Stacked Line ACCase RTA1+HPPDi+HPPDni stack.

In the two groups of F2 individuals sprayed with the higher rates of mesotrione (420 and 630 gm ai/ha) a second QTL was found with strong linkage to SNP marker WG-id1002788. This QTL is the demonstrated genetic position of the causal mutation for high tolerance to mesotrione. The combined tolerance of the QTL developed through mutation breeding on chromosome 1 and the QTL discovered in line P1003 provides a novel tolerance to mesotrione and combined with the linked molecular markers facilitates quick and efficient breeding of new rice varieties (FIG. 16).

4. Rice Resistant to Both ACCase and HPPD Inhibitors

Embodiments of rice resistant to both ACCase and HPPD inhibitors, include rice designated PL121448M2-80048 (ATCC deposit PTA-121362) and PL 1214418M2-73009 (ATCC deposit PTA-121398). (U.S. Pat. No. 9,303,270 B2).

5. Weed Control

Rice lines having different herbicide resistance genes, either pyramided or stacked in the same genetic background or, as single products that are used alternatively in the rotation used by the farmer, represent a critical tool or strategy in extending the useful life of herbicides because these practices slow the development of herbicide resistant variants among the targeted weeds. Several methods are possible to deploy these resistances into hybrids or varieties for weed control, as well as options for hybrid seed production. The rice lines described herein represent new methods for weed control in rice and can be deployed in any of many possible strategies to control weeds and provide for long-term use of these and other weed control methods. In particular, mutant rice tolerant to ACCase or HPPD inhibiting herbicides, and to both ACCase and HPPD inhibitors, are disclosed.

Through developing sources of resistance to multiple herbicides including different mutations producing tolerance through different mechanics to the same class of herbicide, more options are available for weed control in rice. The rice lines claimed provide the ability to use herbicides with a new mode of action for weed control. For example, the ability to use an ACCase inhibiting herbicide in combination with an HPPD inhibitor, represents a mode of action not previously reported in rice. The use of these rice lines including combining lines with resistance to the same herbicide, but with other modes of causative action, provides new options for weed control in grower's fields thus slowing the development of weed resistance. Several methods are possible to deploy this resistance in hybrids for weed control as well as options for hybrid seed production, with different mutations.

A method for controlling growth of weeds in the vicinity of herbicide resistant/tolerant rice plants is also within the scope of the disclosure. One example of such methods is applying one or more herbicides to the fields of rice plants at levels of herbicide that would normally inhibit the growth of a rice plant. For example, at least one herbicide inhibits HPPD activity.

In order to maximize weed control in a rice field, different herbicides may be required to cover the spectrum of weeds present and, in turn, several applications along the crop cycle may be required for any one particular herbicide depending on the overlap between the window of effective control provided by a single application and the window of time during which its target weed may germinate, which often is longer than the protection afforded by a single herbicide application. Temperature, and soil moisture conditions are key factors that affect both window of herbicide efficacy, window of moment of weed germination and growth. Based on these factors, herbicide control models often include sequential repeated application during the crop cycle.

In a standard herbicide tolerance system, for example, one currently used commercially in rice, for resistance to imidazolinone herbicides, the first application of the herbicide is applied at the 2 leaf stage, with the second application following a minimum of 10 days later just prior to the establishment of permanent flood when the plants are tillering. The purpose of the second application is to eliminate weeds that may have germinated after the first application before they can be effectively suppressed by flooding. In some traits, including ACCase inhibitor herbicides, the timing of herbicide applications can be critical not only for effective weed control, but also for the level of tolerance observed in the plants themselves. In one trait under development at RiceTec, plant injury observed in response to herbicide application, aligns closely with plant stage. In this line, very early post-emergence applications cause much higher injury at the 1 leaf stage, with observed injury declining at each growth stage of the plant through first tiller. Some herbicide tolerance traits even exhibit no tolerance to pre-emergent applications even though post-emergence tolerance is excellent. This variable herbicide response linked to plant growth stage requires careful testing to establish the boundaries of safe usage of a new herbicide tolerant product.

Rice production for good yields requires specific weed control practices. Some herbicides are applied as premergents, after planting but before crop emergence; other as postemergents. In the case of rice, postemergent application can be before the crops are flooded, of after. Preferred applications are normally times, according to the developmental stage of the crop, as defined by the number of open leaves in the growing plant. Timing of herbicide applications is an important factor, not only from the perspective of maximizing the efficiency of weed control, but also from the perspective of minimizing impact on the herbicide tolerant crop. This consideration stems from the fact that mutagenized, naturally occurring or transgenic herbicide resistances often are not completely independent of dose and application timing effects. Different genes of herbicide resistance have different dose responses, as well as timing of application responses whereby, typically, phytotoxity in the resistant crop increases as dose increases beyond a certain level, or phytotoxicity to the resistant crop varies with varying timings of application for a given herbicide dose.

Evaluation of the novel herbicide resistance genes, subject of this application, was conducted with a range of suitable herbicide doses that cover application rates typically used for rice farming operations while also taking into consideration possible deviations from the manufacturer-recommended doses. Considering 1×, the recommended manufacturers or best practice recommended dose, the most frequently evaluated additional doses are 2× and 4× with some experiments including other values. A reference to dose by products and active ingredient content is provided in Table 8.

In the case of rice production, weedy red-rice control, which is a target of ACCase-inhibiting herbicides, and broad-leaf weeds targeted with HPPD-inhibitor mesotrione herbicide, are best utilized during the early stages of vegetative grows, prior to flooding, because this technique itself, in the presence of standing water, provides effective weed suppression, all the way to preharvest. Also, considering that for these herbicides phytotoxicity to the resistant crop is higher for younger seedlings, coinciding with the optimal control window, evaluations of these novel herbicide resistance genes includes application primarily at the 2 leaf stage, and the 4 leaf stage, with flooding preferably occurring at the 5-6 leaf stage.

6. Combination of Herbicides

In considering combinations of different herbicide resistance genes, irrespective of whether the combination includes two or more different modes of action for the same herbicide, or two or more genes for herbicides of different families or functions, antagonistic or synergistic interactions may be observed resulting from gene to gene interactions, as some of the embodiments described herein have evidenced. The combination of the novel mutated genes resistant to ACCase-inhibiting herbicides RTA1 and RTA2, result in a herbicide tolerance that is far superior to the additive resistance of the two genes acting individually, demonstrating synergism. Herbicide tolerance results from two mechanisms of action conferring resistance to the same herbicide.

Also, in considering a combination of different herbicide resistance genes, each specific for a different herbicide family, with the expectation that this combination would enable sprayer tank admixtures of the herbicides which in turn reduces machine passes over the crop, synergistic or antagonistic interactions may occur between the herbicide products, as is also evidenced by some of the embodiments described herein. The resistance conferred to rice plants by the gene G2096S, when challenged by herbicides of the ACCase-inhibitor family, is significantly higher than that shown by a rice plant carrying both the RTA1 gene, and also the HPPD1i+HPPD2ni genes that confer resistance to the HPPD-inhibitor herbicide mesotrione. If the plant is challenged with a tank mix that contained the same dose of ACCase-inhibiting herbicide combined with an equivalent working dose of mesotrione. When the different herbicides are applied individually, in any order, and period is allowed between applications, response to the herbicides is similar to that observed in lines carrying the respective single genes. These effects demonstrate an antagonistic interaction between the formulations, when the two herbicides are combined in the tank for crop application. This observation was made when combining quizalofop with mesotrione.

MATERIALS AND METHODS

Mutation Population Establishment

A mutation breeding program was initiated to develop proprietary herbicide resistant/tolerant lines. A permanent mutant population was created by exposing approximately 10,000 seeds (estimated by the average weight of a kernel) of three rice lines including P1003, R0146, and P1062 to both mutagens sodium azide (AZ) and methyl-nitrosourea (MNU). The treated seeds were planted. Individual plants were harvested creating 8,281 potentially mutation lines. The lines have been maintained in confidence as a permanent mutant population for trait screening.

Indica-type restorer line R0146, showing adaptation to US growing conditions, was incorporated into the RiceTec Breeding Program and crossed with 4 other RiceTec restorer R lines to initiate populations required for evaluation. Of different origin when compared to active RiceTec R lines at the time, it was hoped that R0146 would provide novel restoration genes to the RiceTec genetic pool. Showing excellent adaptation, type, productivity and restoration capacity, the use of R0146 and its early selections increased steadily within the US RiceTec Breeding Program. As R0146 and its selections increased in importance in the US breeding pipeline, their utilization also extended to RiceTec South America breeding programs where they also showed outstanding performance. R0146 was the restorer line that stood out as having widest adaptability across testing locations, and highest combining aptitude with diverse female lines, and which consistently produced hybrid combination of high performance. The decision was made to use R0146 as the single restorer line to undergo mutagenesis for discovery of herbicide tolerance traits. No other line had at the time that level of penetration in the RiceTec breeding pipeline, positioning R0146 as the best candidate for rapid and wide utilization of the novel genes sought from the mutagenesis effort.

Enhanced Tolerance/Resistance to ACCase Inhibitors

Validation of the Mutant Line ML0831265-02283 for Tolerance to ACCase Herbicides.

Figure 6:
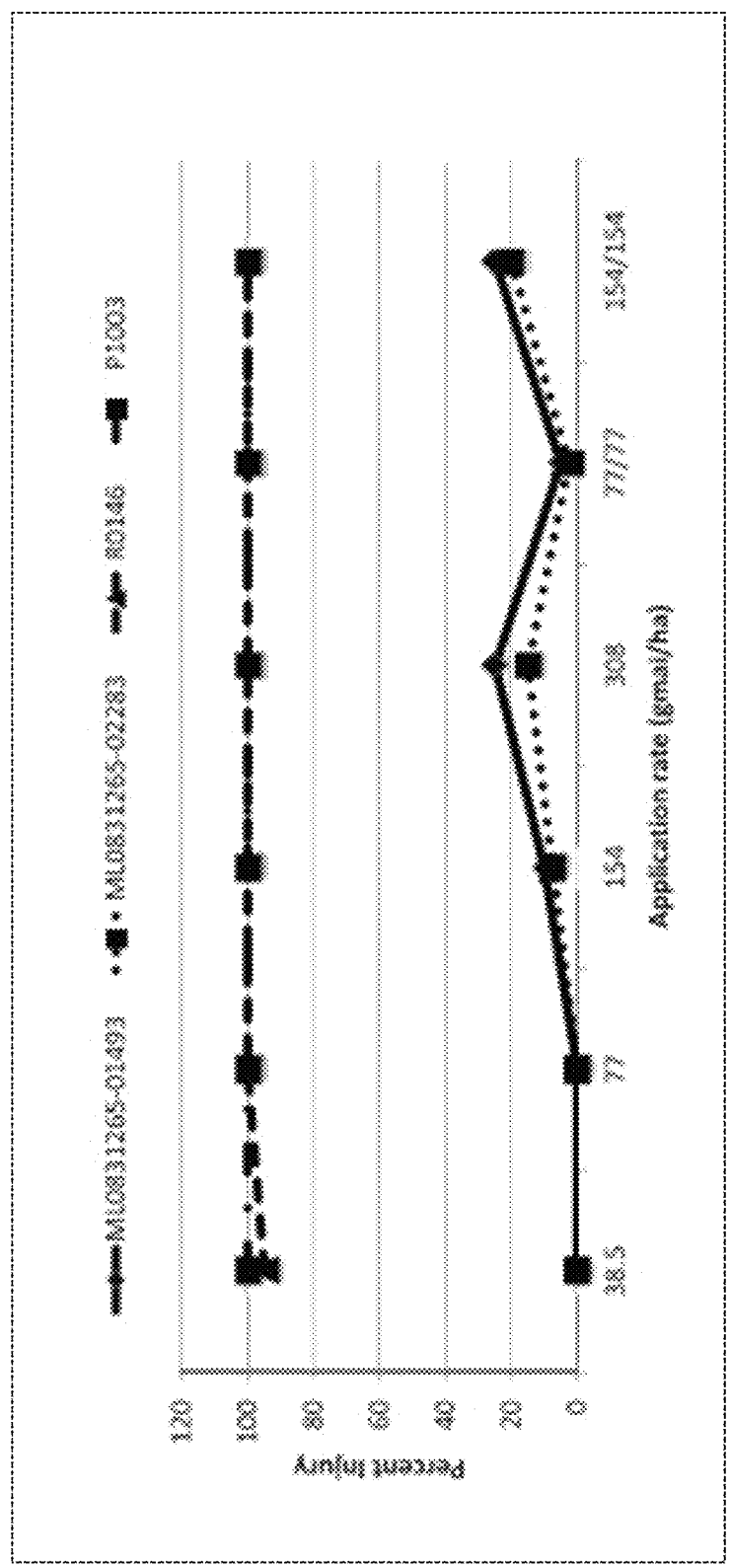
Figure 7:
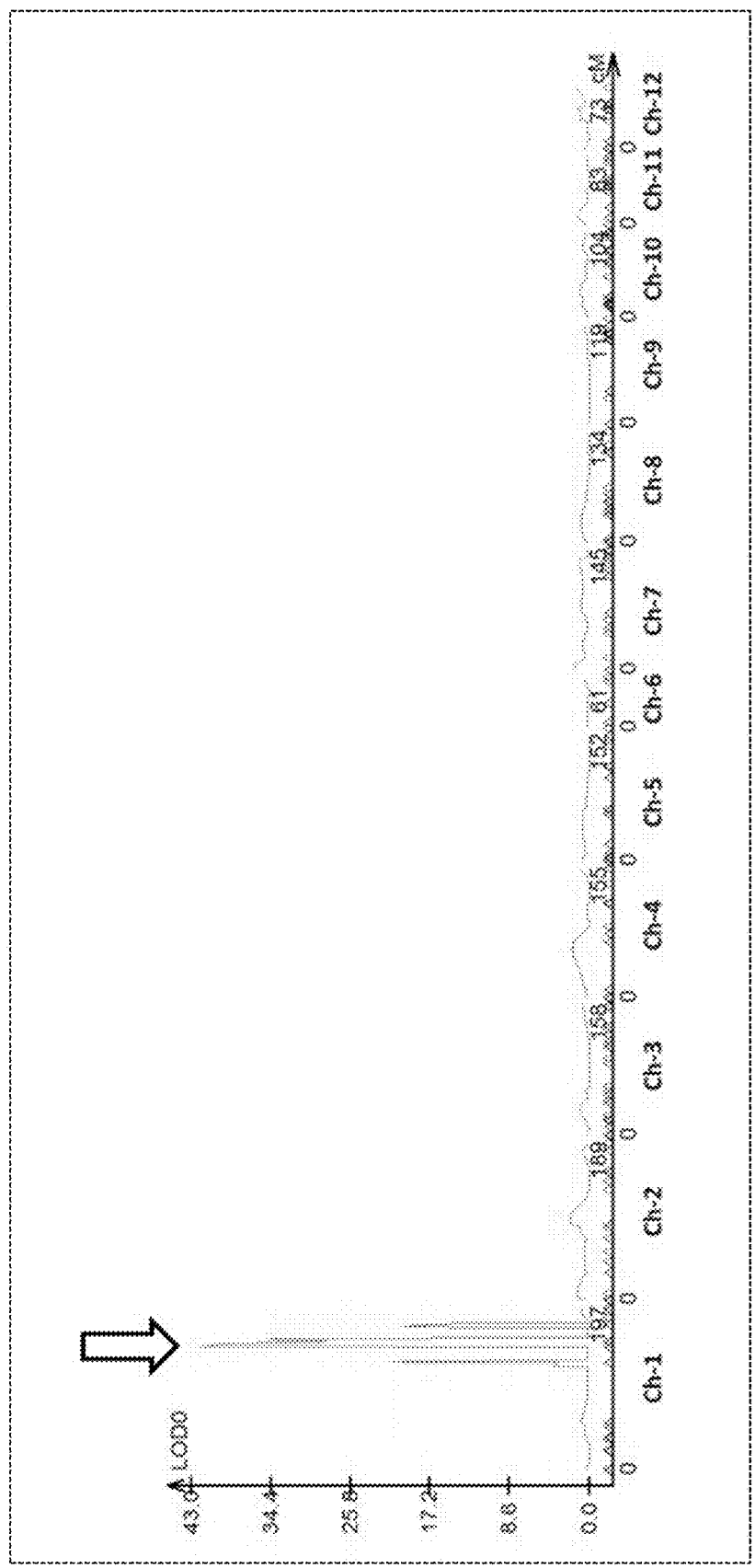
Figure 8:
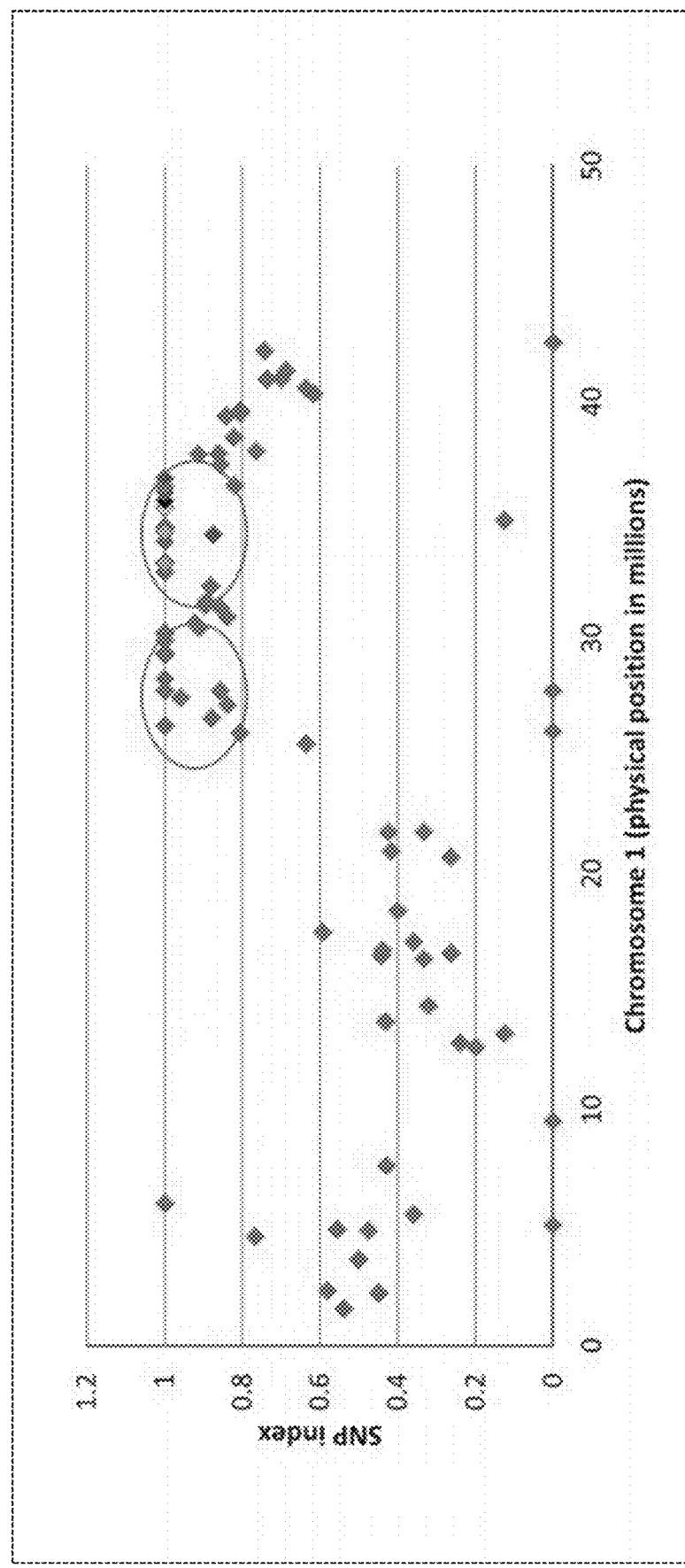

After screening a large mutant population, the line ML0831265-02283 also survived application of the ACCase herbicide quizalofop. The line was increased to obtain sufficient seed for larger trials to evaluate its tolerance to ACCase herbicides. The tolerance to ACCase herbicides in line ML0831265-02283 was validated by planting in the field plots (5 feet by 10 feet) of the line, the non-mutant parent line R0146, a second non-mutant line P1003, and the ACCase tolerant line ML0831265-01493. The ACCase herbicide quizalofop was applied at the four leaf stage at 0.5×, 1×, 2×, and 4× multiples of the labeled rate (77 gmai/ha). Twenty one days after the herbicide was applied the plots were evaluated for percent injury caused to the rice based on control plots that had no herbicide application (FIG. 6). The data confirms the tolerance of line ML0831265-02283 and it may even carry more tolerance than line ML0831265-01493 as shown by less injury at the 2× and 4× rates of quizalofop.

Development of Tolerance to HPPD and ACCase Inhibiting Herbicides by Combining the Tolerances in Lines ML0831266-03093 and ML0831265-01493

Herbicides that target the HPPD enzyme, primarily control broad leaf weeds. However trials in rice show prevalent control of grass weeds in rice, including red weedy rice especially with mesotrione herbicide.

On the other hand, the primary weed target of ACCase herbicides is monocot plants including rice, grass weeds, and red rice. However, some ACCase herbicides have lower activity on rice. This weakness is likely transferred to red rice as the plants are very closely related. Combining the HPPD tolerance and the ACCase tolerance into a single rice line allows a broad spectrum weed control strategy for rice. The HPPD herbicide controls broad leaf weeds and enhances the effect of ACCase herbicides for control of monocot weeds including red rice.

Combining the HPPD tolerance with the ACCase tolerance into a single rice line was initiated with the HPPD tolerance mapping project by crossing the HPPD tolerant line ML0831266-03093 to the ACCase tolerant line ML0831265-01493. In mapping the F2 population plants were selected for HPPD tolerance by applying mesotrione first at a low rate (105 gmai/ha) followed by a high rate (630 gmai/ha). In this process molecular markers were also developed allowing future selection of HPPD tolerance by either markers or herbicide tolerance screening or both.

Figure 13:
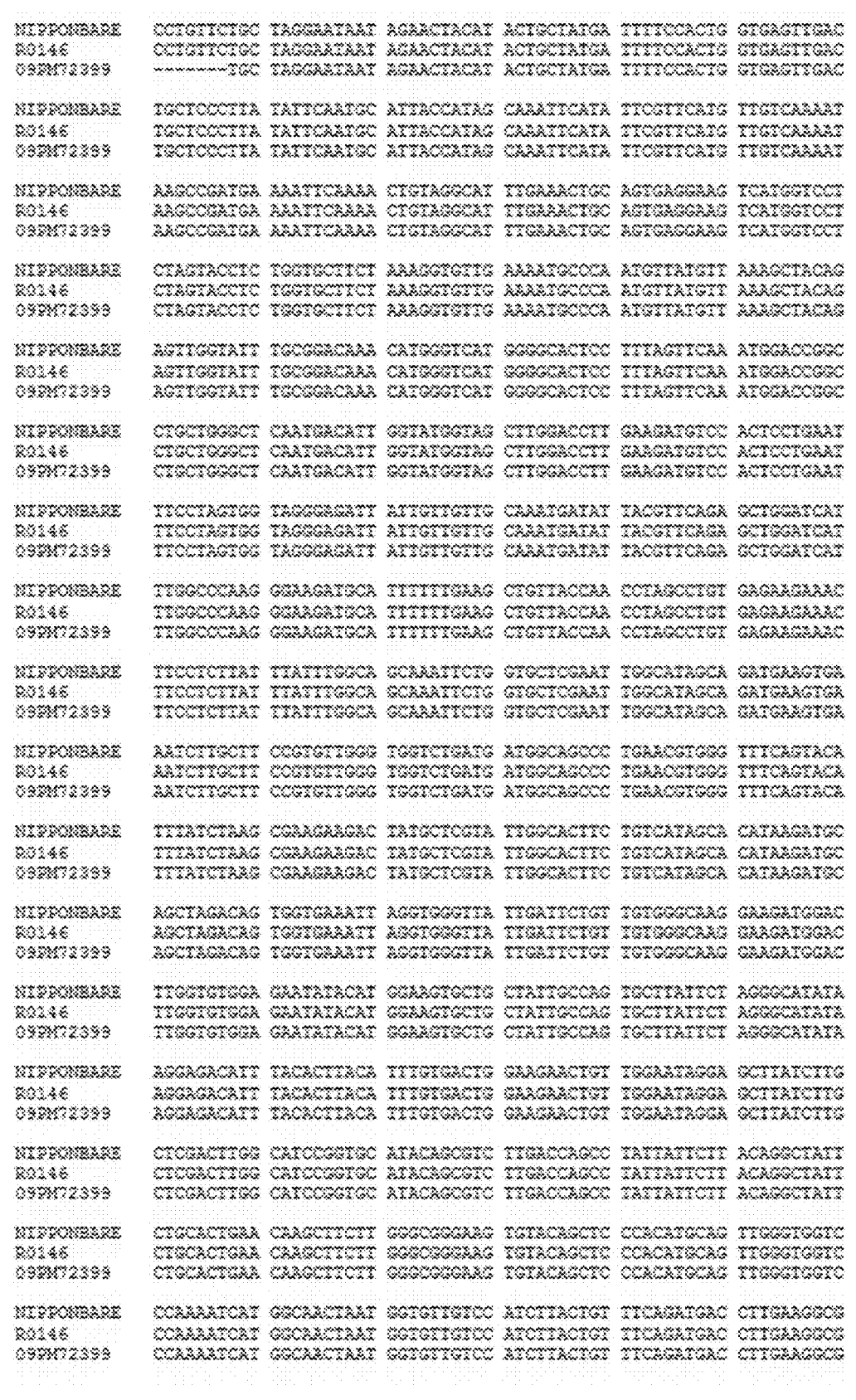
Figure 13:
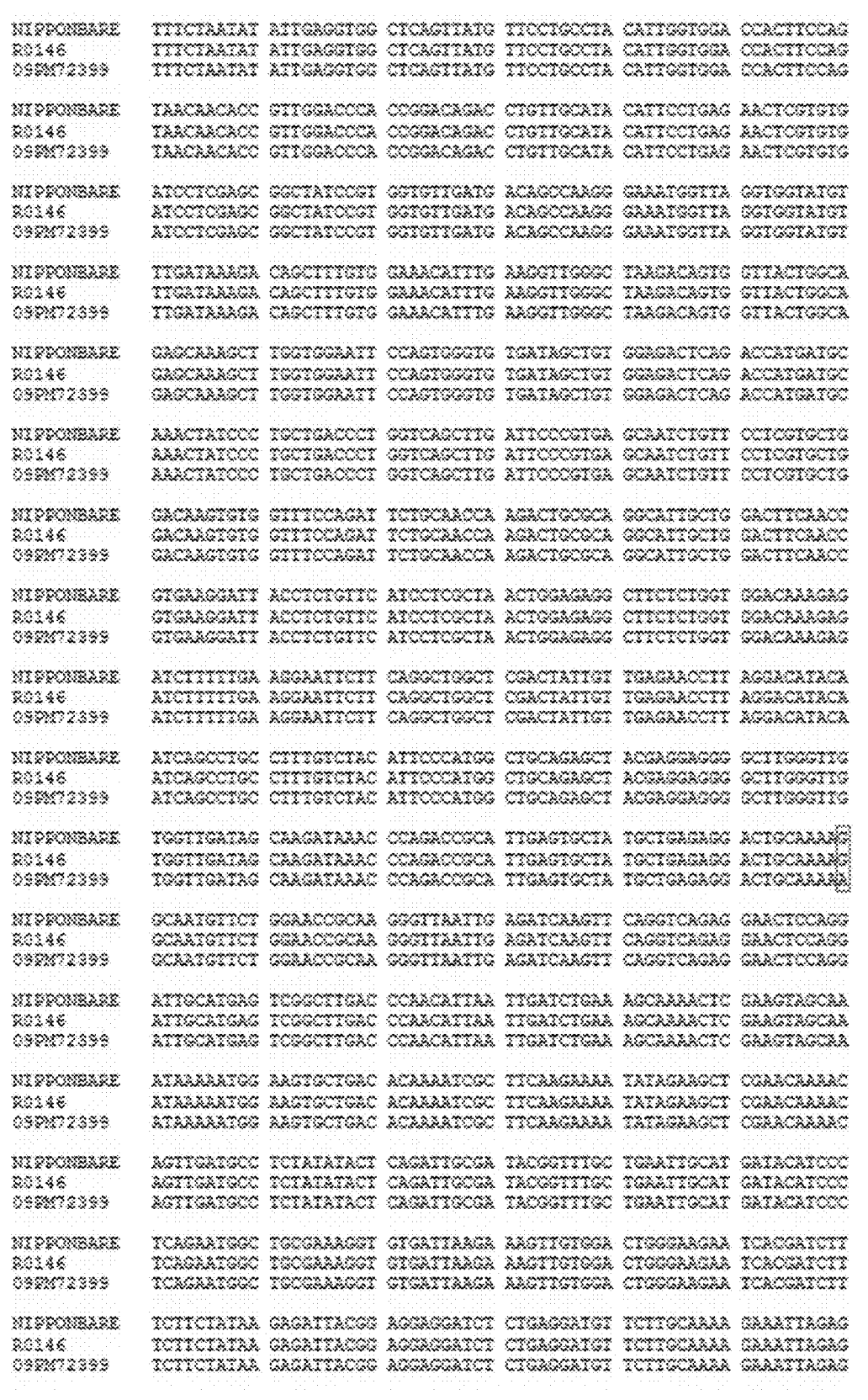
Figure 13:
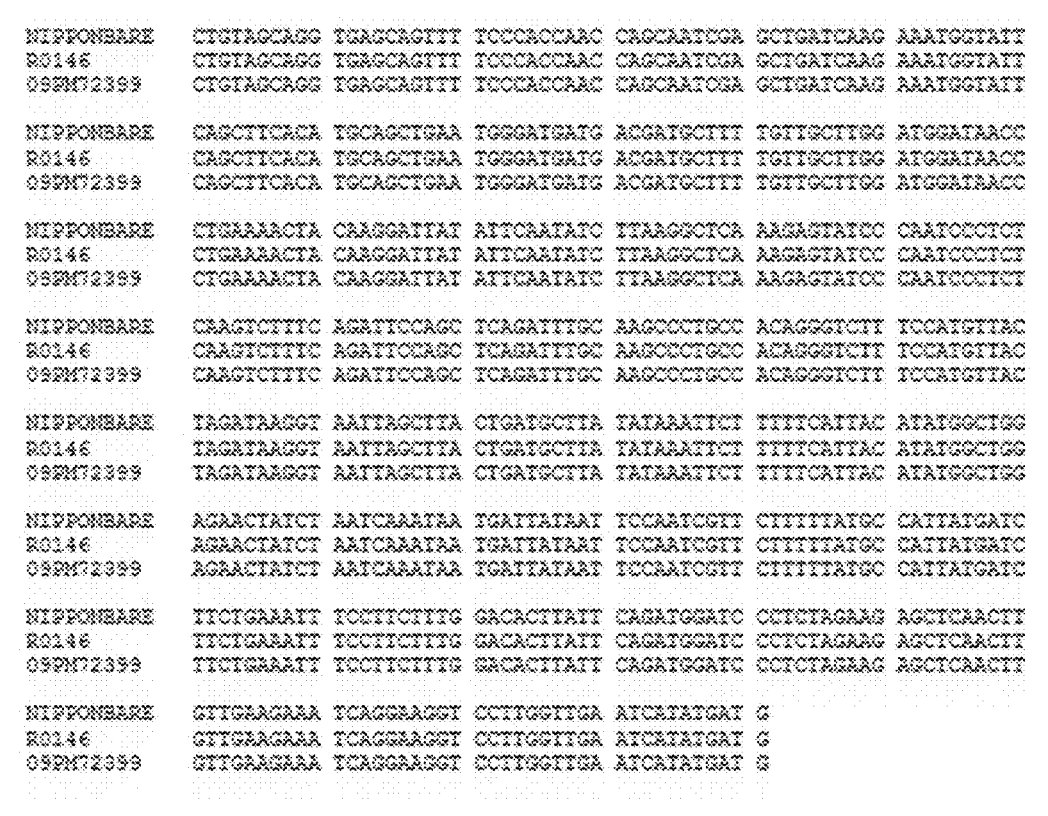
Figure 14:
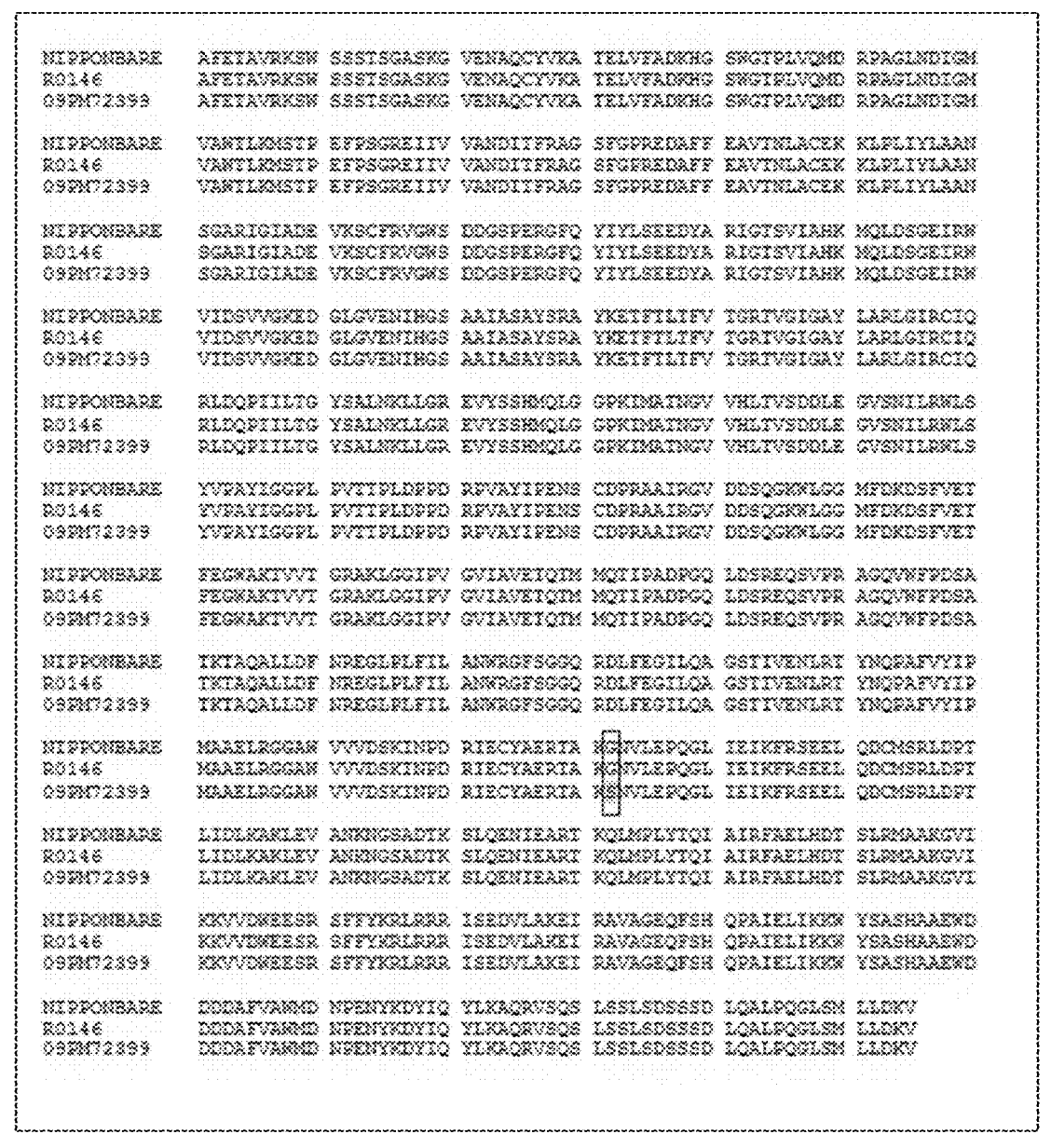

After identifying plants that were tolerant to the HPPD herbicide mesotrione, they were also tested with the ACCase tolerance functional marker for the RTA1 mutation in the ACCase donor parent line ML0831265-01493. Information to develop ACCase RTA1 markers are in FIGS. 13, 14.

After this process, a set of 25 F2 plants with the ACCase mutation to herbicide resistance, and the HPPD genetic herbicide resistance on chromosome 1 and chromosome 2, in at least the heterozygous condition, were identified. The plants were transplanted to another field for harvesting at maturity. Out of the 25 plants, eight were homozygous for the ACCase mutation and one plant was homozygous for the ACCase mutation, the HPPD tolerance mutation, and the non-induced tolerance gene. The 25 plants were bagged at flowering and the seed harvested at maturity from each plant individually.

An early maturing group of plants was harvested as early as possible and the seeds planted in the greenhouse to help quickly advance to the F4 generation. Selections on the F3 plants were made by molecular markers flanking the HPPD tolerance mutation and native tolerance the ACCase functional mutation. Homozygous plants for all the selected genomic regions were advanced to the F5 generation. The F5 seed was confirmed to carry tolerance to ACCase herbicides and the HPPD herbicide mesotrione. Among the F5 lines PL1214418M2-80048 was selected due to a high seed yield and being homozygous for the ACCase tolerance mutation at position RTA1, the HPPD tolerance mutation, and the HPPD tolerance native gene. Seed from the line PL1214418M2-80048 was deposited at the ATCC and given a deposit number PTA-121362 (see Table 9).

A second line was developed by planting F3 seed in rows. The plants were sprayed with the HPPD herbicide mesotrione and selected for little or no injury as compared to unsprayed controls. Leaf tissue was also collected and the plants were tested for inheritance of the ACCase tolerance mutation RTA1, the HPPD mutation tolerance, and the HPPD non-induced tolerance. Plants homozygous for all three tolerance genes or QTLs were identified and harvested. The F4 seed (PL1214418M2-73009) was bulked together from plants carrying all three tolerance genes or QTLs and used for testing or as a new donor line for tolerance to both ACCase and HPPD herbicides. Seed of the source PL1214418M2-73009 was deposited at the ATCC and given a deposit number PTA-121398 (see Table 5).

Figure 1:
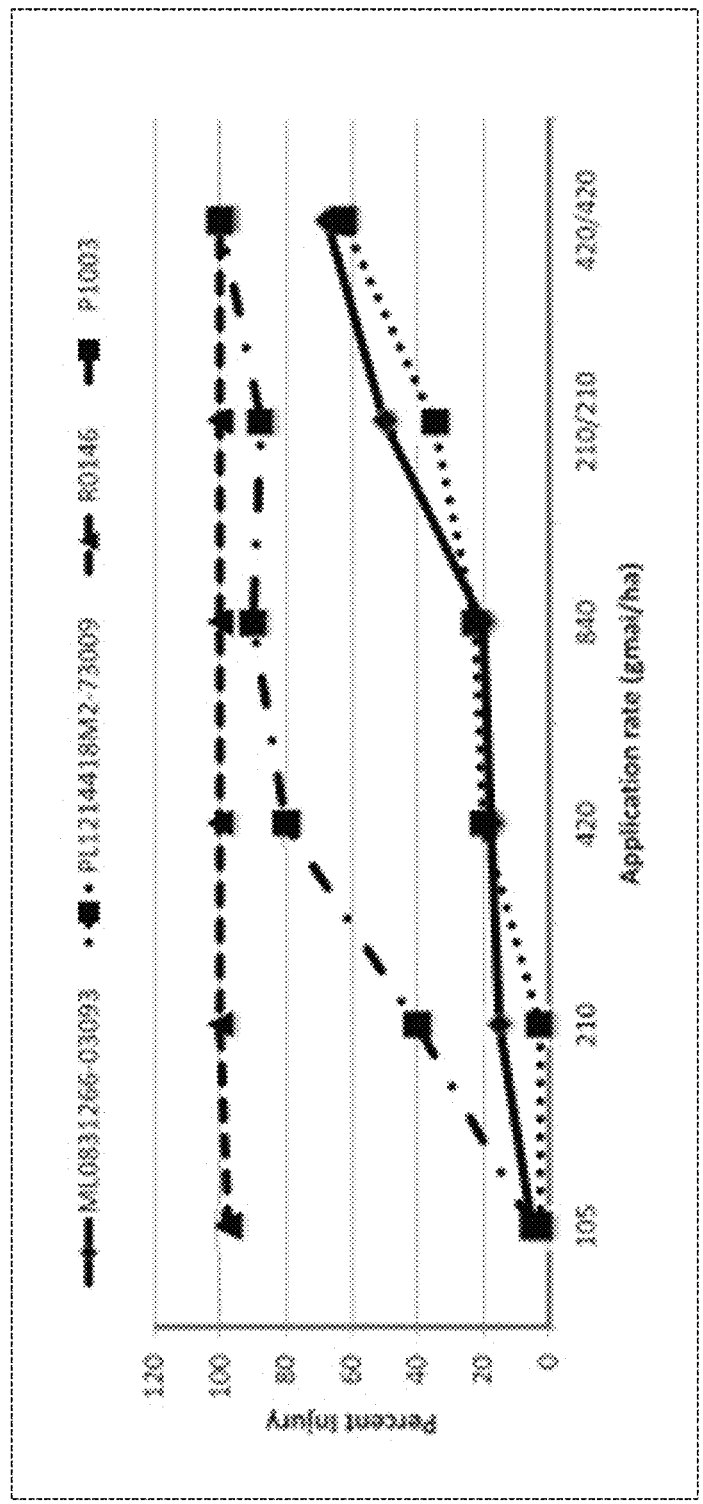

Tolerance of New Lines Combining HPPD and ACCase is Equivalent and Selectable in Breeding Populations The seed source PL1214418M2-73009 was developed from a cross between the HPPD resistant line ML0831266-03093 and the ACCase resistant line ML0831265-01493 and was sufficient to allow testing to verify equivalent tolerance to HPPD and ACCase inhibitors in new lines. Two trials were conducted to measure recovery of tolerance to both ACCase and HPPD herbicides in the new line PL1214418M2-73009. Recovery of tolerance in the line combining the two traits will illustrate that the traits are heritable and can be used to produce new varieties and hybrids carrying herbicide resistance. These trials are important as often times it is difficult to recover complex QTLs for quantitative traits or in some cases a traits response is dependent upon the genetic background. In the first trail the lines resistance to mesotrione (HPPD herbicide) was evaluated by planting line PL1214418M2-73009, the HPPD resistant line ML0831266-03093 and wild-type rice line P1003 and R0146 in plots (5 feet×10 feet). Mesotrione was applied at 0.5×, 1×, 2×, and 4× multiples of the labeled application rate (210 gmai/ha). Two additional treatments were included with a 1× and 2× rate followed by a second application 14 days afterward with the same rates. Full recovery of the HPPD resistance from line ML0831266-03093 was achieved in the line PL1214418M2-73009 as it and the original trait line had the same response to the herbicide applications (FIG. 1). These results show that the HPPD resistant trait can be bred and selected to develop commercial products.

Figure 2:
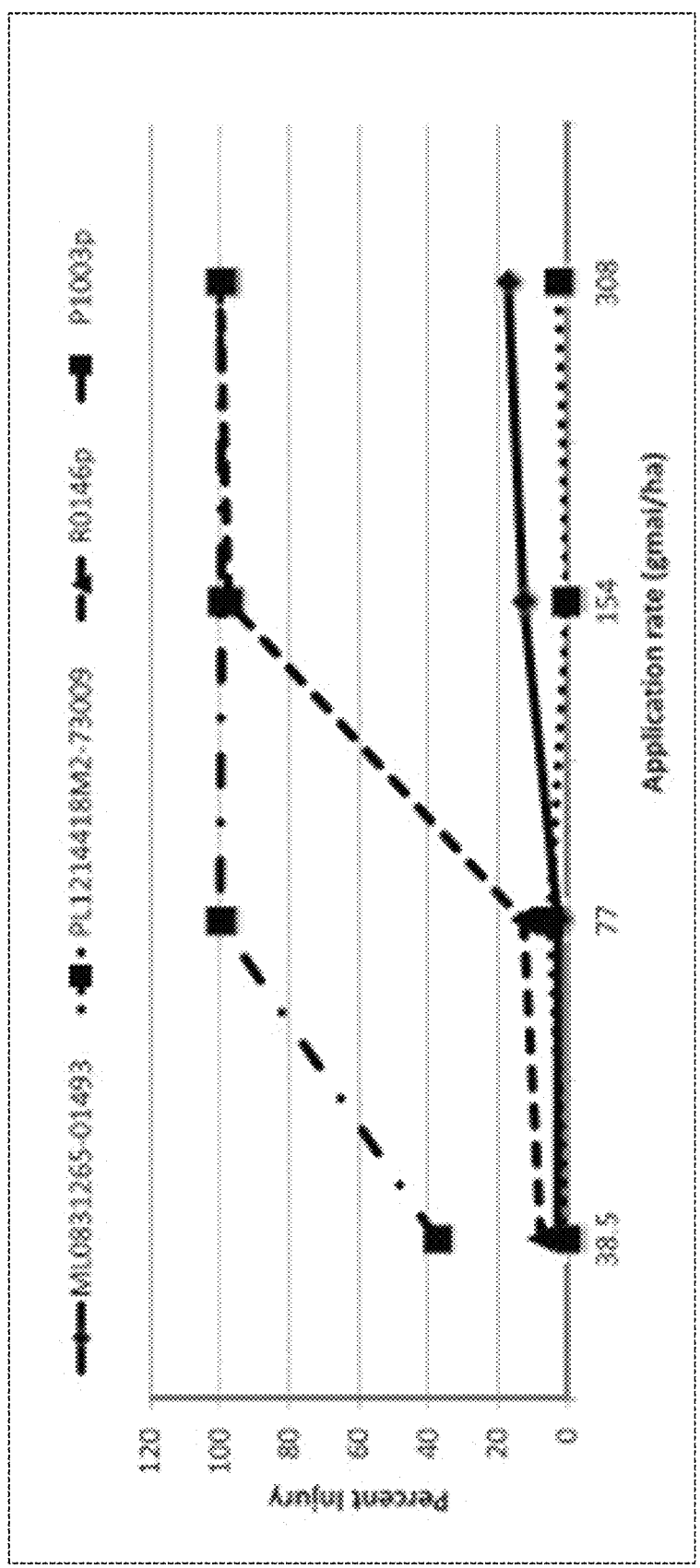
Figure 3B:
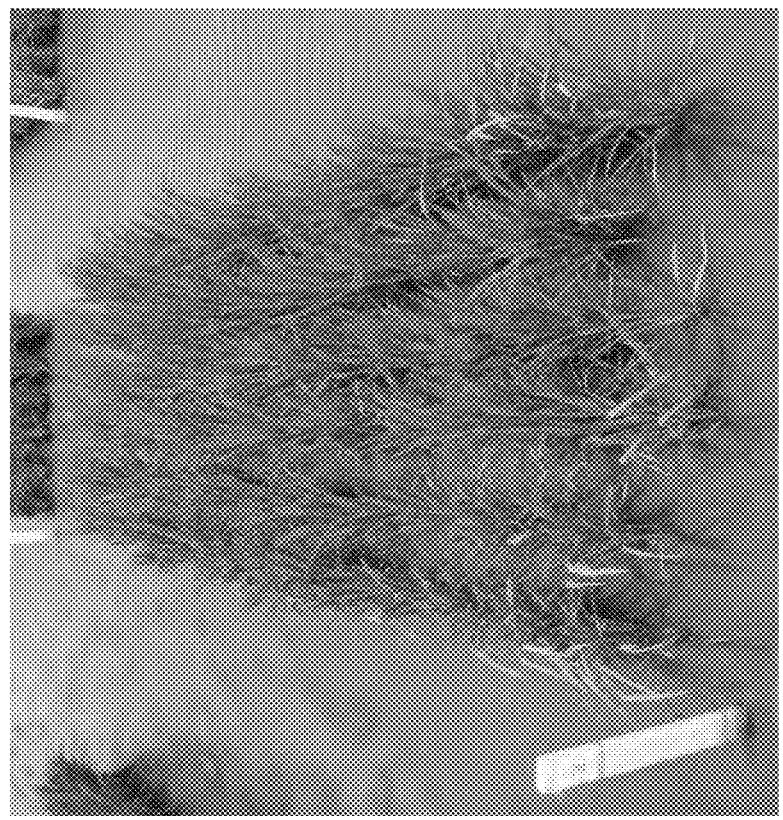
Figure 3A:
Figure 3D:
Figure 3C:

Another trial was conducted to confirm recovery of the ACCase inhibitor resistance from the RTA1 mutation as in the line ML0831265-01493. In this trial the new line PL1214418-73009 with combined HPPD and ACCase tolerance was planted in a row along with other various lines including the original donor line ML0831265-01493 (planted in a plot), ML0831266-03093, P1003, R0146 parent line for ACCase tolerance. The lines were all tested with the ACCase herbicides fluazifop at 0.5×, 1×, 2×, and 4× multiples of the label application rate (210 gmai/ha) and quizalofop at 0.5×, 1×, 2×, and 4× multiples of the label application rate (77 gmai/ha). In these trials the three new lines that inherited the ACCase tolerance all showed equivalent tolerance to the ACCase herbicides as did the donor line ML0831265-01493 (FIG. 2).

The tolerance to HPPD herbicides is more complex than the ACCase tolerance because it requires two genes that are different from the gene targeted by the herbicide. In spite of this greater complexity, the equivalent tolerance was recovered through selection of both the native tolerance gene and the mutation tolerance. The ACCase parent line ML0831265-01493 in this cross was highly sensitive to the HPPD herbicide mesotrione and thus was not expected to contribute any towards HPPD tolerance. Resistance/tolerance to HPPD herbicides is mostly likely caused by these two genes alone as they were the focus of the selection process, and the new line PL1214418M2-73009 shows equivalent resistance. These results show that the resistance for both ACCase and HPPD inhibitors is inherited and can be bred into any rice for commercial development of both HPPD and ACCase inhibitor resistance in rice.

Identification of the Tolerance Contribution from the HPPD Tolerance Mutation and the Non-Induced Tolerance Gene from P1003

During the breeding process to develop new lines (PL1214418M2-80048 and PL1214418M2-73009) with resistance/tolerance to HPPD and ACCase herbicides, two other lines were also investigated to determine the contribution of the HPPD tolerance mutation and the HPPD tolerance native gene. The line PL1214418M2-73001 carries ACCase tolerance and only the HPPD tolerance, whereas mutation PL1214418M2-73013 carries ACCase tolerance and only the HPPD native tolerance gene. These selections allow the estimation of the tolerance effect of each of the two genes required for tolerance to HPPD herbicides. The tolerance effect of each gene was measured by growing the lines in single rows including the newly developed line PL1214418M2-73009 that carries both the HPPD tolerance from the mutation and the non-induced tolerance, the HPPD tolerant line ML0831266-0309, and the non-induced parent line P1003. The field plots were sprayed at the 4 leaf stage with the HPPD herbicide mesotrione at 0.5×, 1×, 2×, and 4× multiples of the labeled application rate of 210 gmai/ha.

Figure 4:
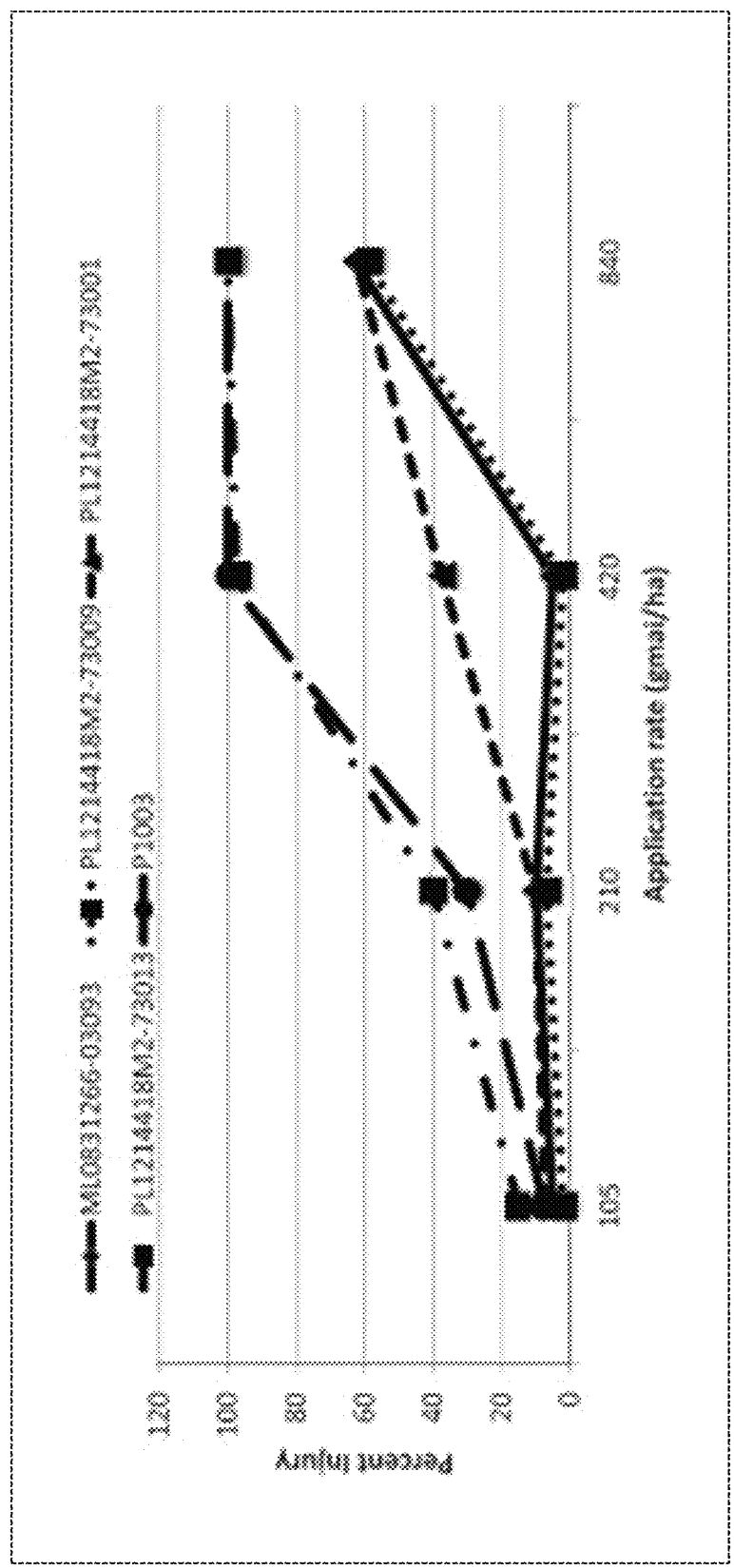

The plots were evaluated 4 weeks after the herbicide was applied. The results showed that the native tolerance gene alone (PL1214418M2-73013) gave tolerance levels similar to the parent line P1003 (FIG. 4). This result would be expected if the native tolerance gene located on chromosome 2 located within the QTL flanking markers is the only causative source of tolerance in the non-mutant line P1003. The line PL1214418M2-73001 that carries only the HPPD mutation located on chromosome 1 within the QTL flanking markers, shows intermediate tolerance between the non-mutant line P1003 and the HPPD mutant line ML0831266-0309. This result shows that the HPPD mutation provides not only enhanced tolerance but also a greater level of tolerance than the native tolerance gene. In addition it also suggests that the HPPD mutation functions independently of the HPPD native tolerance gene. The two genes also appear to function in an additive manner as only by combining the two in the new line PL1214418M2-73009 does the tolerance level become equivalent to the original mutant line ML0831266-0309.

Controlling Weeds and Red Rice in Rice Crops with ACCase Inhibitors and HPPD Inhibitors The herbicide activity or ability to control non-mutant rice, such as line R0146 and P1003, is a good predictor of how well the herbicides will control red rice or wild weedy rice in a rice crop. Red rice and wild weedy rice are very similar to rice, even with the ability to cross with rice. This similarity is the reason these weeds are so difficult to control in a rice crop. The mutant lines (ML0831265-01493, ML0831265-02283, ML0831266-03093, PL1214418M2-80048, and PL1214418M2-73009) disclosed offer a new weed control strategy for red rice, wild weedy rice, and other weeds common in rice crops. These lines give rice tolerance to herbicides that will normally kill or cause yield reducing injury to the rice crop.

While testing the tolerant lines, the parent lines were also tested to serve as controls and as an indication of commercial potential as a red rice/wild weedy rice control strategy. These trials showed that select treatments of the herbicides applied alone or in various combinations and application timings offer a new weed control strategy in rice crops.

Figure 5B:
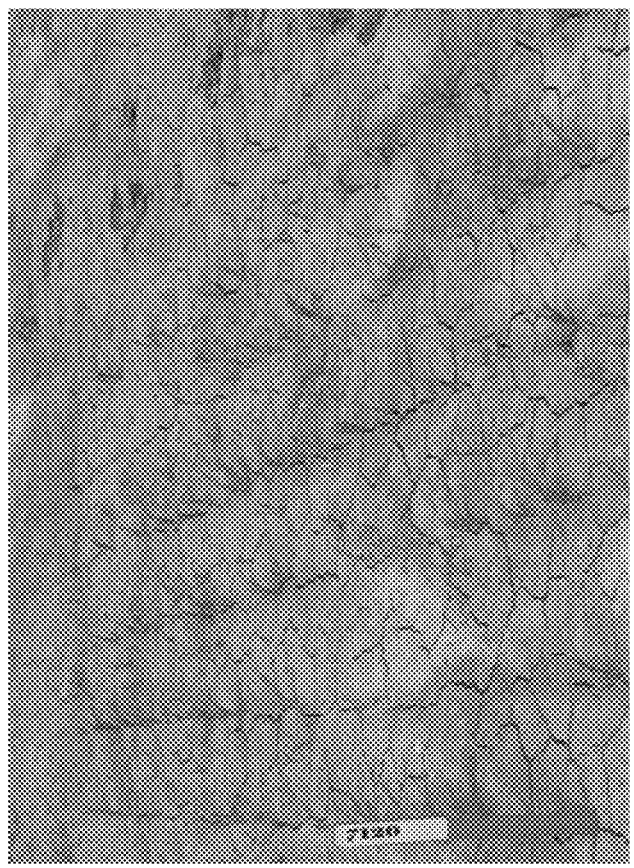
Figure 5A:
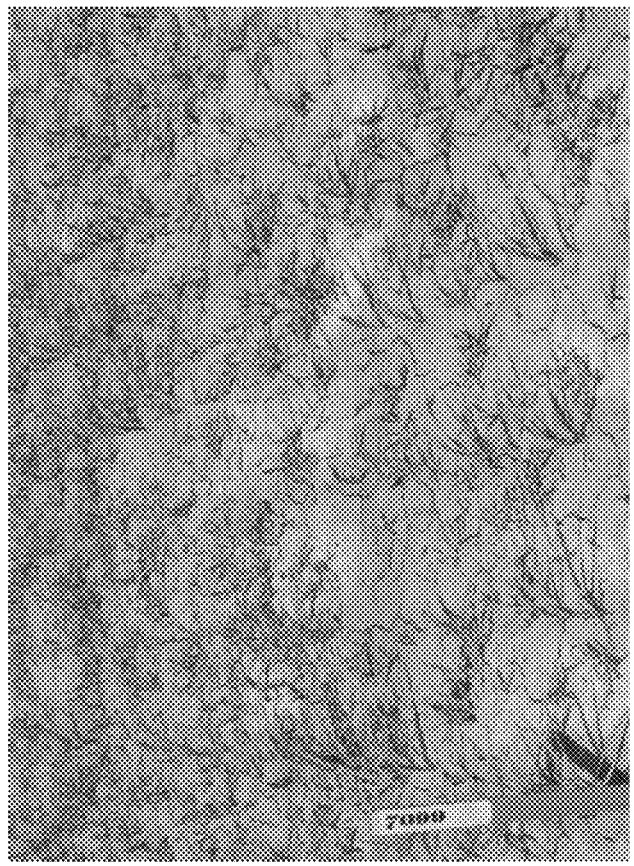

Rice is tolerant to certain ACCase inhibitor herbicides, for example cyhalofop is registered for use in rice. However other ACCase herbicides kill or severely injure rice to varying degrees. After testing, several of these other herbicides including fluazifop and quizalofop were found to offer good control of common grass weeds, such as barnyard grass, in rice. Control of common weeds in rice was also achieved with mesotrione alone, especially when applied pre-plant or at higher rates (2× the labeled rate of 210 gmai/ha) (FIG. 5A and FIG. 5B). The applied rates of both types of herbicides giving the weed control are well within the tolerance level of the respective ACCase and HPPD tolerant lines including the combined lines carrying tolerance to both HPPD and ACCase herbicides.

Development of the HPPD and ACCase tolerance into single lines (PL1214418M2-80048 and PL1214418M2-73009) gives the opportunity for an additional weed control strategy involving applications of ACCase and HPPD herbicides in a tank mix or individually at different times. The very effective pre-plant application of the HPPD herbicide mesotrione can now be followed with ACCase herbicides applied alone or in combination with HPPD herbicides. This strategy provides full spectrum weed control in a rice crop by broad leaf weed control provided by the HPPD herbicide, and grass weed control by the ACCase herbicide. In addition the control of grasses and red rice/weedy rice by ACCase herbicides is greatly enhanced by the activity provided by the HPPD inhibiting herbicide. This strategy is anticipated as being especially effective for control of red rice when an ACCase inhibiting herbicides are used that have lower activity on rice.

This particular weed control system is highly useful in rice crops due to some weeds, including red rice, developing tolerance to currently used herbicides. Use of this weed control strategy allows rotation of different modes of action herbicides in rice crops. By rotating different modes of herbicide action the development of resistant weeds is slowed or prevented allowing for longer term use of all available weed control methods.

Figure 12A:
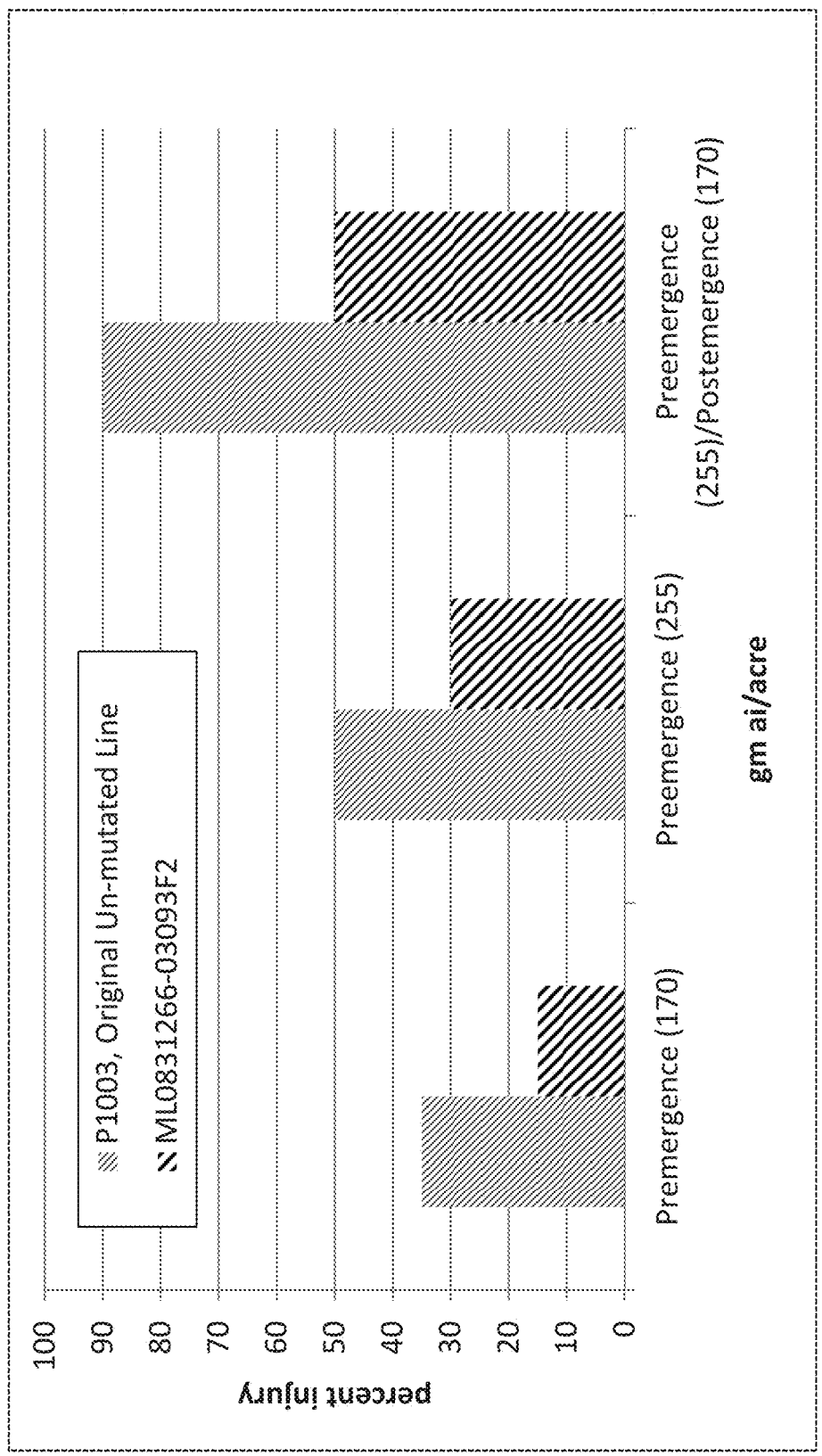
Figure 12B:
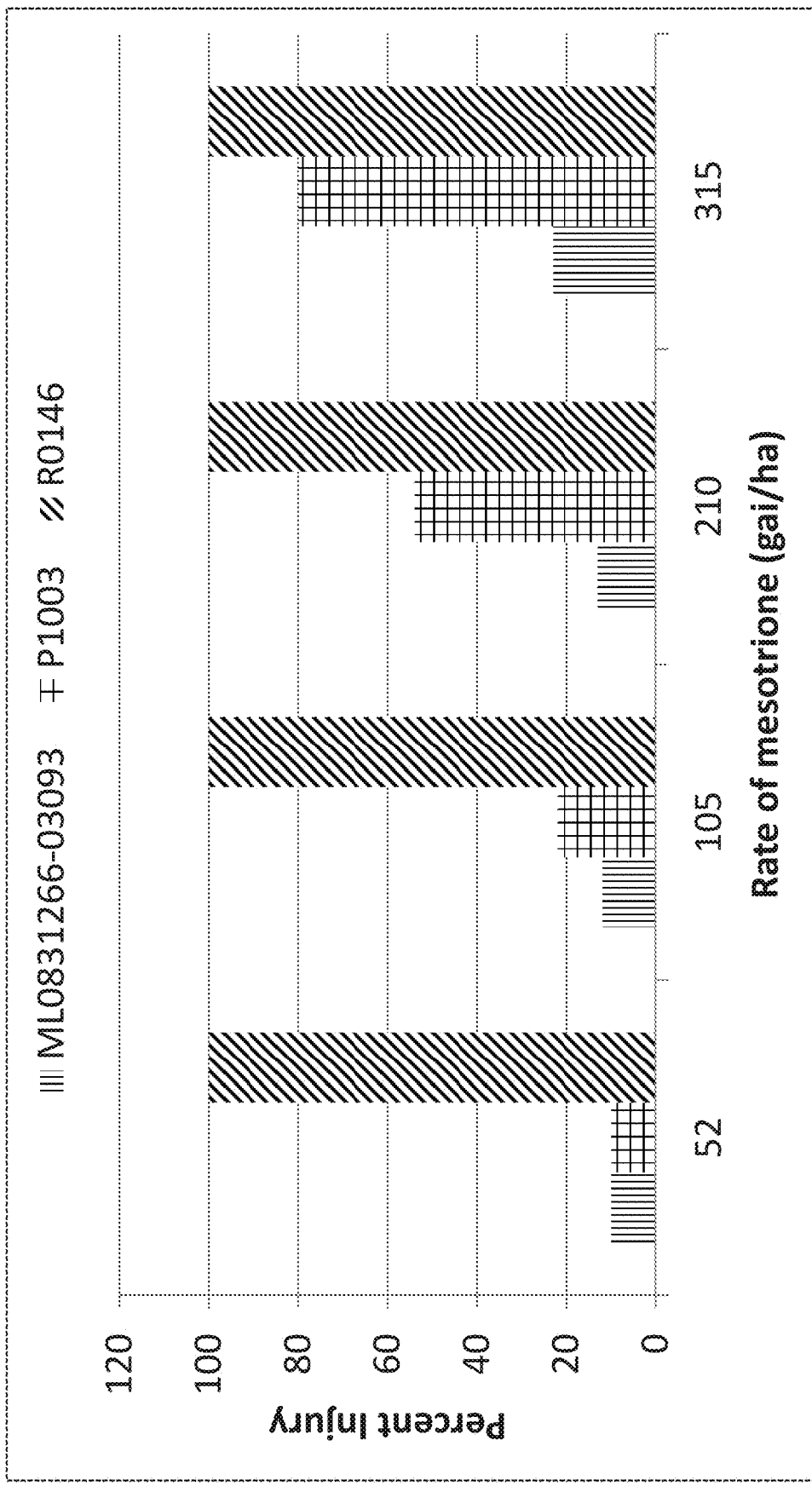
Figure 15:
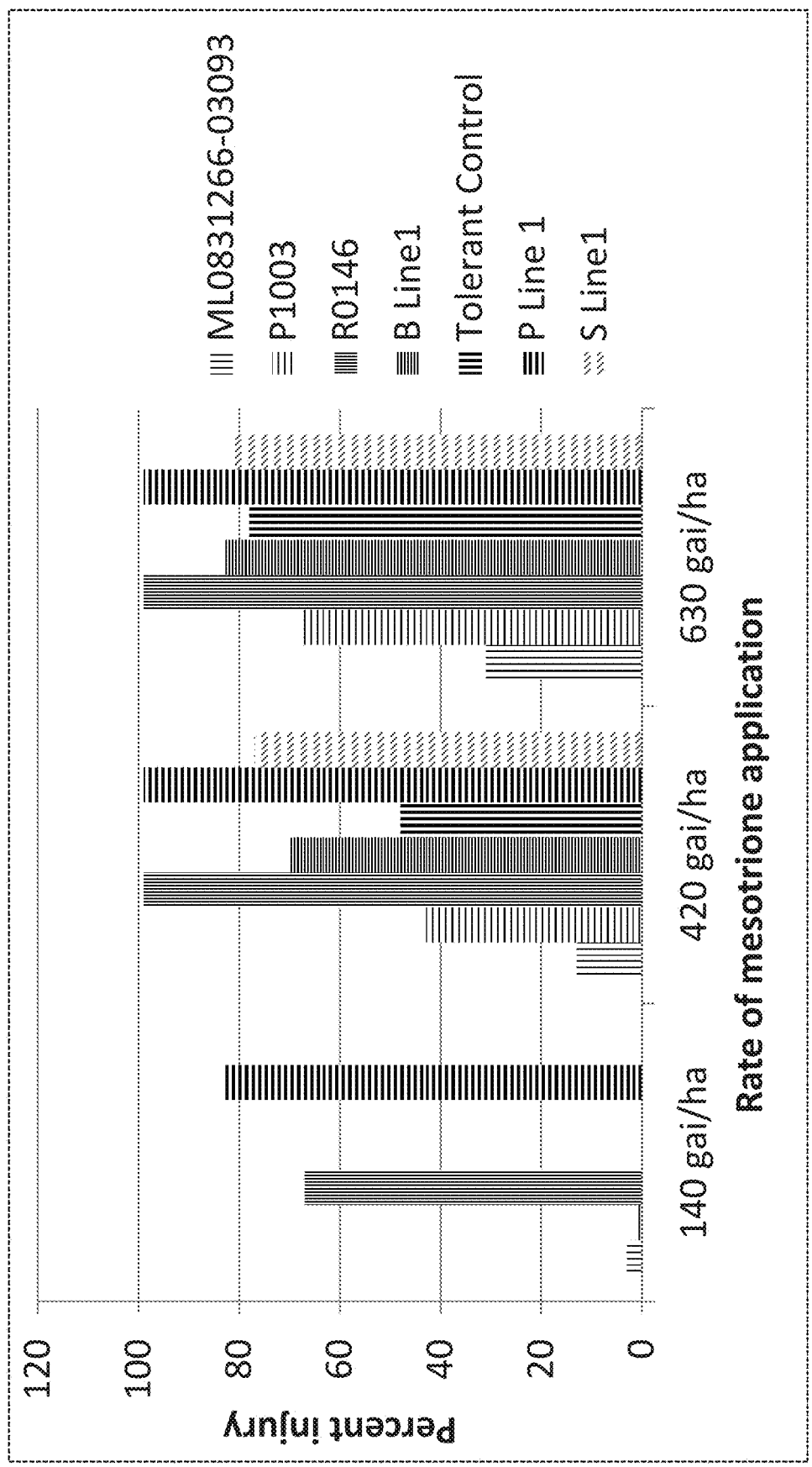

Validating the Mutant Line ML0831266-03093 for Tolerance to HPPD Inhibiting Herbicides After the initial screening of the "mutation population," the lines with no damage were selected and tested in additional experiments using different rates of the herbicide. In particular, a rate response experiment was conducted in which two different rates of mesotrione were applied pre-emergence, plus an additional foliar application was also applied. This experiment differentiated one mutant line as having superior resistance (less injury) to the mesotrione herbicide as compared to the control (FIG. 12A and FIG. 12B). Progeny of this designated ML0831266-03093 are maintained as a new line carrying resistance to mesotrione herbicide. The line (ML0831266-03093) is a source of resistance that is backcrossed into proprietary rice lines or used directly in breeding to develop new proprietary rice lines. The developed lines are a source of herbicide resistance for use in development of new hybrids that offer an alternative mode of action to control weeds in rice. Affording this opportunity to growers is of great value both in providing high yields and in extending the useful life of available weed control technologies.

The mutant line ML0831266-03093 was found to carry tolerance to mesotrione (a common HPPD inhibiting herbicide) through screening the line with different rates of the herbicide. The tolerance level of ML0831266-03093 was found to be much greater than the original non-mutant (native) line P1003.

The original line P1003, carries natural tolerance to mesotrione. This non-induced resistance of the original line sometimes masked the resistance of the mutant line making the enhanced resistance of the mutant line ML0831266-03093 not obvious.

Further validation of the trait involved testing the mutant line ML0831266-03093 in the presence of common rice weeds. The mutant line was completely tolerant to the applied rates of mesotrione whereas the prevalent weed population was well controlled by the herbicide (FIG. 6A and FIG. 6B). This level of grass weed control was completely unexpected as mesotrione is labeled for controlling broadleaf weeds in monocot crops. This result indicates that mesotrione and other HPPD inhibiting herbicides in combination with line ML0831266-03093 and derived lines, represent a new weed control system in rice. The high activity of the mesotrione on grass weeds and certain types of rice indicates that the system could be used to control red rice in a rice crop.

Mesotrione and other HPPD inhibiting herbicides target the HPPD gene. An increase in herbicide tolerance could be achieved through a mutation in the HPPD gene. A mutation within the gene sequence can alter the enzyme structure sufficiently to prevent it from being inhibited by the herbicide, but still allow it to carry-out its normal physiological function. Assuming this as a plausible tolerance mechanism, the HPPD gene was sequenced by Sanger sequencing in both the mutant line ML0831266-03093 and the original line P1003. Surprisingly, no mutation was found in the HPPD gene. The herbicide tolerance in line ML0831266-03093 appears to be derived from a non-target site process.

EXAMPLES

Example 1: Location of the Mutation Designated RTA2 Associated with Tolerance to ACCase Inhibitors A MutMap population was F2 plants from a cross between rice line R0146 X ML-083126502283F2. Pictures were taken 16 days post herbicide spray.

The herbicide Quizalofop was sprayed on the test fields. Thirty days after the herbicide spray, plants showed very clear 'black and white response' to the herbicide [showed either resistance to herbicide (scored 1 or 3) or susceptibility (scored 7 or 9) 16 days after herbicide spray. The plants were scored first at 16 days after the herbicide spray and then at 21 days after herbicide spray.

Mutant plants carrying the 'unknown mutation RTA2' were resistant. 3 week old plants were sprayed with Quizalofop and the herbicide response was scored 21 days after the spray. Susceptible symptoms were already observed 7 days after the Quizalofop spray, but scoring was done at 21 days. On the $21^{st}$ day, a majority of the plants showed very clear 'black and white' responses to the herbicide, that is, showed either resistance to herbicide (score 1) or were completely dead (score 9). Few plants scored 3 (little damage on leaves or new leaf growth observed, and most likely plants will survive) or score 5 (half of the canopy is damaged and hard to predict whether the plants will survive or not), or score 7 (more damage on leaves, plants will not survive).

After detection of ACCase resistant mutants in the R0146 rice population, the MutMap approach was used to characterize by linkage analysis the mutation(s) associated with the Quizalofop resistance phenotype.

The MutMap process: Mutagenesis is a rice cultivar with a reference genome sequence by ethyl methane sulfonate (EMS). The mutant generated, in this case a semi dwarf phenotype, was crossed to a wild-type plant of the same cultivar prior to mutagenesis. The resulting F1 was self-pollinated to obtain F2 progeny segregating for the mutant and wild-type phenotypes. Crossing of the mutant to the wild-type parental line ensured detection of phenotypic differences at the F2 generation between the mutant and wild type. DNA of the plants F2 displaying the mutant phenotype were bulked and subjected to whole genome sequencing, followed by alignment to the reference sequence. SNPs with sequence reads composed only of mutant sequences (SNP index of 1) are putatively closely linked to the causal SNP for the mutant phenotype.

The strongest indication of putative mutations associated with ACCase inhibitor resistance was observed by Chromosome 1, with a string of sequential mutations with the highest SNP Index.

Figure 18:
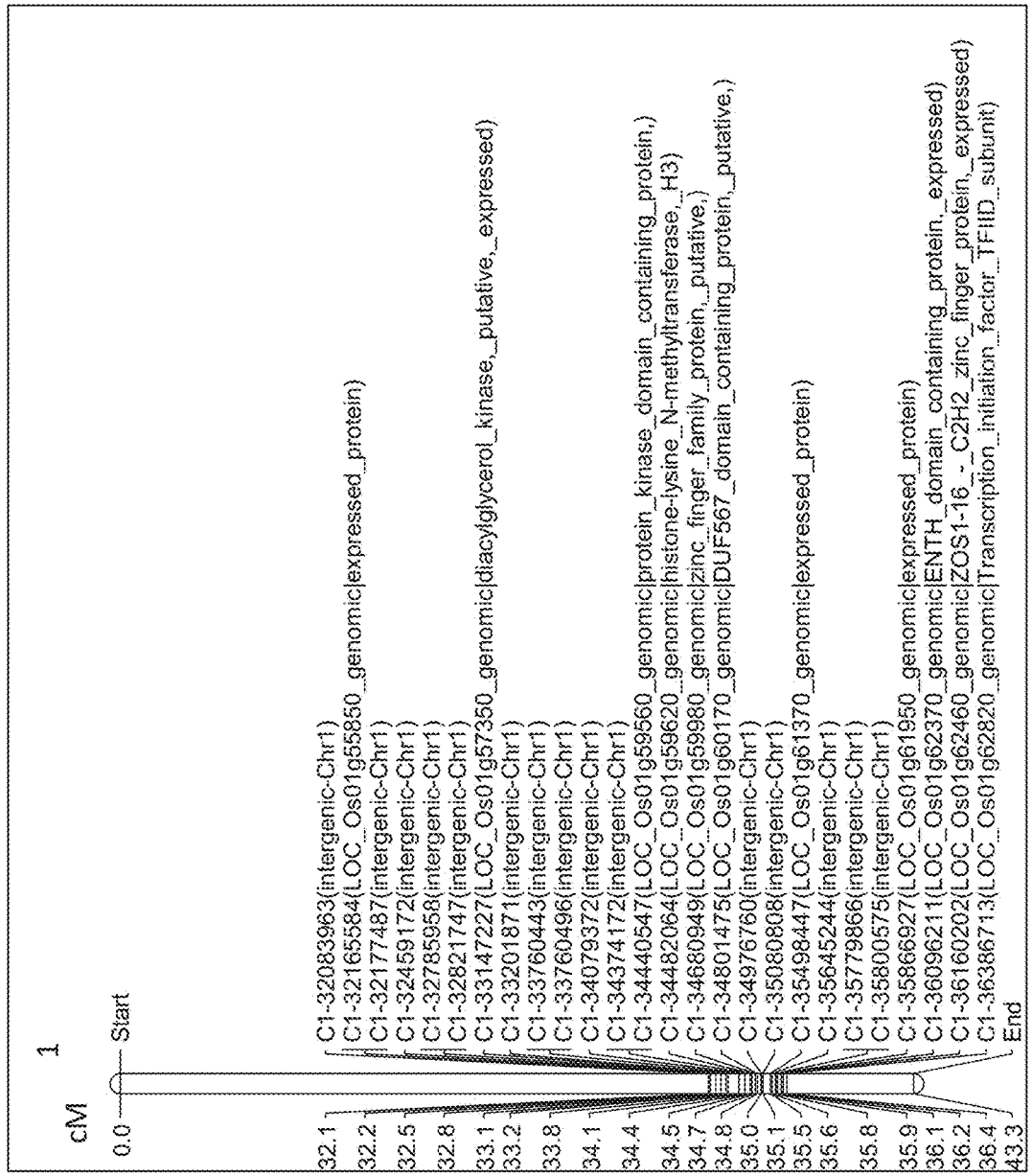
FIG. 18 shows location, in Chromosome 1, of the mutations identified by the MutMap procedure, as implemented for the QTL mapped to that region with the 44 k array markers, defined as the ACCase RTA2 locus.

The casual region was located to a region in chromosome 1 identified in FIG. 18 and Tables 1A, 1B and 2.

Example 2: Production of Hybrid Rice with Low Dose Resistance to One ACCase-Inhibiting Herbicide Family, FOPs, by \Addition of a Single Resistance Gene in Single Allelic Dose The ACCases inhibiting herbicide resistance provided by ML0831265-01493 is deployed individually into hybrids through either the male or female parent resulting in the hybrid seed being resistant to the herbicide. If the resistance is deployed in only the male parent, then in addition to its use for weed control, the herbicide when applied to hybrid seed kills contaminating female selfed seed. On the other hand if the resistance is deployed only through the female parent, growers may eliminate contaminating male selfed seed. Efficacy of this approach depends on the gene action of the herbicide resistant gene, whereby single allele presence must still confer viable herbicide tolerance to be viable.

Growers may alternate the type of resistance they purchase and apply in their fields to reduce the chance that weeds develop resistance to the herbicide. The ACCase inhibiting herbicide, though primarily for control of broad leaf weeds, also allows for some enhanced control of red rice. At higher rates it will kill certain types of rice. If resistance arose in red rice from cross pollination, it could still be controlled with a different herbicide class in the next season.

Example 3: Production of Hybrid Rice with Low Dose Resistance to One HPPD Inhibiting Herbicide by Addition of a Single Resistance Gene in Single Allelic Dose The HPPD inhibiting herbicide resistance provided by ML0831266-03093 is deployed individually into hybrids through either the male or female parent resulting in the hybrid seed being resistant to the herbicide. If the resistance is deployed in only the male parent, then in addition to its use for weed control, the herbicide when applied to hybrid seed kills contaminating female selfed seed. On the other hand if the resistance is deployed only through the female parent, growers may eliminate contaminating male selfed seed. Efficacy of this approach depends on the gene action of the herbicide resistant gene, whereby single allele presence must still confer viable herbicide tolerance to be viable.

Growers may alternate the type of resistance they purchase and apply in their fields to reduce the chance that weeds develop resistance to the herbicide. The HPPD inhibiting herbicide, though primarily for control of broad leaf weeds, also allows for some enhanced control of red rice. At higher rates it will kill certain types of rice. If resistance arose in red rice from cross pollination, it could still be controlled with a different herbicide class in the next season.

Example 4: Production of Hybrid Rice with Higher Level of Resistant to Either HPPD or ACCase Inhibiting Herbicides by Addition of a Single Resistance Gene in Double Allelic Dose The HPPD inhibiting herbicide resistance provided by ML0831266-03093 or the ACCases inhibiting herbicide resistance provided by ML0831265-01493 are deployed into both the male and female parents of a hybrid. The resulting hybrid seed may carry resistance to mesotrione and other HPPD inhibiting herbicides, or the ACCase-inhibiting herbicides. Resistance provided in this manner is stronger and offers better weed control through the possibility of being able to apply higher rates of herbicide.

Example 5: Production of Hybrid Rice Resistant to Multiple Independent Resistance Genes for a Unique Herbicide or Herbicide Family Two or more independently genes conferring resistance to a herbicide or a herbicide family or group, are deployed in a single hybrid by adding each one separately to either one or both of the parents of the Hybrid. Depending on the gene action of the genes to be stacked in the hybrid, they may be introgres sing in a single parent, resulting in a single alleleic dose in the commercial hybrid, or they may be added to both Female and Male parental lines, resulting in a homozygous, double allelic dose in the commercial hybrid for that locus. Deployment in this manner results in hybrid seed having higher Herbicide resistance that a hybrid carrying either single resistant gene under identical allelic dosage, due to the complementing effect provided by the different resistance genes. Stacking on the HPPDi mutated gene with the HPPDni alleles in line ML0831266-03093 represents such a case in which different independent resistance loci/alleles for HPPD-inhibiting herbicide tolerance combine to produce a product of greater resistance that that conferred by either of the single genes. Similarly, the ACCase stack of RTA1+ RTA2, in line RL1225468 represent a parallel example of added resistance when combining two independent genes for resistance to ACCase-inhibiting herbicides of the FOP family.

Example 6: Production of Hybrid Rice Resistant to Herbicides Belonging to Different Herbicide Classes, Such as HPPD-Inhibitors and ACCase-Inhibitors, by Adding 1 or More Herbicide Resistance Genes for Each of the Herbicide Classes, Such as Mesotrione and FOP Herbicides 1. Resistance to mesotrione and at least one other herbicide class, ACCase-inhibitors, is deployed in a single hybrid by using a male parent that carries resistance to the mesotrione (or the other herbicide class ACCase) and a female that carries the other resistance. The method allows the grower to make a single purchase but to be able to choose which herbicide to apply. A single class of herbicide may be used in any one season and rotated between seasons, or alternatively both herbicides could be applied within a single season. In addition, deployment by this method, elements contaminating selfed seed of both parents in the hybrid seed through application of both herbicides, or one type or the other, are eliminated through application of only one herbicide.

2. In another method of deployment the mesotrione resistance and the ACCAse-inhibitor resistance is deployed through making a hybrid with a male parent that carries both resistances. The grower then has the option to choose which herbicide class to apply or to apply both within a single season. In addition, through the application of either herbicide contaminating selfed female seed would be eliminated. Alternatively both herbicide class resistances are provided in the female parent, giving the grower the same options for weed control.

3. Another embodiment is to deploy the mesotrione resistance to both parents, and another herbicide resistance into only one parent, such as the male parent. The hybrid seed are then homozygous for the mesotrione resistance but not the other. A scheme like this is used to make an early application with the herbicide put into only the male parent, providing weed control and elimination of contaminating female selfs. Later in the season mesotrione may be applied or another HPPD inhibitor herbicide. The useful life of both herbicides is extended through limiting or eliminating the development of weed resistance. In another application this method allows the use of mesotrione or other HPPD inhibitor herbicide to control weeds in seed production fields, allowing for cleaner seed.

4. Alternatively a different herbicide could be deployed in both of the hybrid parents and the mesotrione/HPPD inhibitor is deployed in only the male parent.

5. Other embodiments for deploying herbicide resistant lines include other traits such as resistance to other classes of herbicides, or other traits of importance.

Example 7: Seed Production

The herbicide resistance is also used for seed production. As an example, if it is deployed into the female parent, making it resistant, the herbicide is applied to the seed production field to kill the male plants before setting seed so that a seed production field is harvested as a bulk. In addition the purity of the seed may also be verified through deploying two herbicide resistances with only one in each parent. Selfed seed is detected and eliminated by applying herbicide put into the other parent.

Example 8: Control of Broadleaf Weeds and Limited Control of Grasses

The resistance when deployed in a hybrid, by any combination, provides resistance to mesotrione or other HPPD inhibiting herbicides. This deployment results in a new mode of action in rice to control broadleaf weeds with some limited control of grasses such as red rice. Further options or broad spectrum control of weeds is provided by deployment in the same hybrid another resistance to herbicides providing grass weed control, such as ACCase inhibiting herbicides. Through deployment with other modes of action development of weed resistance is more likely to be prevented through the use of multiple modes of action.

Example 9: Selection of Herbicide Resistant Rice Using a Herbicide Bioassay

Selection of material inheriting mesotrione tolerance is accomplished by a simple herbicide bioassay. A high rate of mesotrione (at least 420 gm ai/ha) is applied allowing differentiation of heterozygous individuals from homozygous individuals and the tolerance level of the mutation line from the inherent tolerance level in the background of some types of rice. In one example a rate of 105 gm ai/ha is applied followed three weeks later by a second application of 630 gm ai/ha. In another example a rate of 420 gm ai/ha is applied in a single application. Yet another example entails applying the herbicide at a rate of 630 gm ai/ha. Herbicide applications are done at the three to four leaf stage of seedling growth. The ideal situation is to have also planted near or within the plants to be selected a set of plants from the original mutant mesotrione tolerant donor line ML0831266-03093, a row of plants of the wild-type of the mutation line, P1003, and a row of the line involved as the other parent in the cross. These control lines allow easy differentiation for inheritance of the tolerance provided by the ML0831266-03093 mutant line through comparison of the response in the plants to be selected with the control lines. Only plants that live and are relatively healthy will have inherited and be homozygous for the tolerance level provided by the ML0831266-03093 mutant line.

Example 10: Production of Rice Resistant to Both HPPD and ACCase Inhibiting Herbicides The mutant line ML0831266-03093 that is tolerant to mesotrione and likely other herbicides including HPPD inhibitors, was crossed with mutant line ML0831265-01493 having tolerance to ACCase herbicides and more specifically "fop" type of ACCase herbicides. In one example the ML0831266-03093 plants are the female parent and pollination is by a plant from line ML0831265-01493. In another embodiment the parents are reversed so that ML0831266-03093 serves as the pollinating parent. The resulting F1 seed are harvested having inherited both mesotrione and ACCase herbicide tolerance. The F1 individual carries tolerance to both herbicides at a partially dominant level so they show some tolerance but not to the same level as the tolerant parent lines.

The F1 seeds are planted and the resulting plants are allowed to self-pollinate to produce F2 seed making a population segregating for tolerance to both mesotrione and ACCase herbicides. This population is screened by an herbicide bioassay to identify individuals that have inherited tolerance from the original mutant line ML0831266-03093 and are homozygous for the resistance. A high rate of mesotrione is applied allowing differentiation of heterozygous individuals from homozygous individuals and the tolerance level of the mutation line from the tolerance level in the background of some types of rice including the original line used for mutation to create the ML0831266-03093 line, which was P1003.

In one example a rate of 105 gm ai/ha is applied followed three weeks later by a second application of 630 gm ai/ha. In another example a rate of 420 gm ai/ha is applied in a single application. Yet another example entails applying the herbicide at a rate of 630 gm ai/ha. Herbicide applications are done at the three to four leaf stage of seedling growth. The ideal situation is to have also planted near or within the F2 population a set of plants from the original mutant mesotrione donor line ML0831266-03093, a row of plants of the wild-type of the mutation line, P1003, and a row of the line involved as the other parent ML0831265-01493. These control lines will allow easy differentiation for inheritance of the tolerance provided by the ML0831266-03093 mutant line through comparison of the response in the F2 plants to these control lines. Only plants that live and are relatively healthy will have inherited and be homozygous for the tolerance level provided by the ML0831266-03093 mutant line.

Example 11: A Co-Dominant Marker Assay to Select and Develop ACCase and HPPD Tolerant Rice Lines A simple co-dominant marker assay is available to select for inheritance to ACCase herbicides derived from line ML0831265-01493. The marker is developed as a single nucleotide polymorphic marker and detects the causal mutation at position RTA1 (blackgrass number) for ACCase tolerance in line ML0831265-01493. All of the surviving plants following the mesotrione bioassay as employed in Example 8 are sampled for tissue collection, the DNA is extracted by known methods and the samples are tested with the SNP assay. A subset of the surviving plants are then also identified as carrying homozygous tolerance to ACCase herbicides through marker assisted selection.

Individuals with tolerance to both mesotrione and ACCase herbicides are selfed to produce F3 families and further selected for other important agronomic characters. The F3 lines are selfed and purified to derive a new line or variety with dual resistance to mesotrione and ACCase herbicides. Such lines are highly valuable as the use of both herbicides provides more complete and broad-spectrum weed control.

In another embodiment the individuals with tolerance to both mesotrione and ACCase are used as trait donors in a backcross (BC) breeding program. After selecting one individual or a few individuals they are used either as the pollinating parent or the female parent. Another more elite and desirable line serves as the recurrent parent to which the traits are transferred.

Following the first cross the F1 plants are crossed again to the recurrent parent. The resulting backcross seed from this cross and ongoing crosses to the recurrent parent are tested with either markers or through herbicide bioassays for inheritance of the herbicide tolerance or a combination of markers and bioassays. In the best situation markers for the functional mutations are used. Alternatively an herbicide bioassay for mesotrione is applied to the BC seed or possibly the BC seed is progeny tested to verify inheritance of the tolerance. Furthermore an herbicide bioassay is used to identify individuals that also inherited tolerance to ACCase herbicides. This process is repeated until the recurrent parent genome is recovered along with the two new traits for tolerance to mesotrione and ACCase herbicides. After the last backcross individuals are selfed to recover the dual herbicide tolerances in a homozygous resistant level in at least one plant.

In yet another embodiment the individuals with resistance to both mesotrione and ACCase herbicides are crossed to a third line and subsequently selfed or even crossed with other lines. The resulting new lines and germplasm is tested and evaluated for other agronomic important traits. Finally new varieties or male and female lines are developed with tolerance to both mesotrione or other HPPD herbicides and ACCase herbicides a combination novel to rice.

Example 12: Mutant Rice ML0831266-03093

The mutant line ML0831266-03093 is demonstrated to carry a high tolerance level to mesotrione herbicide beyond the tolerance found naturally in some rice types including the original mutation treated line P1003. The mutant line is planted in rows or alternatively whole plots are planted and rows of the unmutated line (P1003) and other types of rice or whole plots are planted. Mesotrione is applied pre-emergence or alternatively it is applied post-emergence at the three to four leaf stage of the rice plants. Various rates of mesotrione are applied pre-emergence, pre-emergence followed by post-emergent, or post-emergent with a single or sequential application. Post-emergent applications are applied at the 3-4 leaf stage of the rice.

With low rates (105 gm ai/ha) of mesotrione applied both the mutant line as well as the original unmutated line survive. However, other types of rice, such as the mutant line with ACCase tolerance ML0831265-01493 and the associated unmutated line R0146 are killed at these rates of mesotrione. Applying mesotrione herbicide at higher rates clearly shows new and novel tolerance level as only the mutant line ML0831266-03093 survives while the original unmutated line P1003 and all other tested lines are killed or severally injured. The higher tolerance to mesotrione makes the line ML0831266-03093 of commercial value as both the tolerance can be controlled or bred into new varieties and it is of a high enough level to allow commercial weed control in rice with the application of mesotrione herbicide and possibly other HPPD inhibiting herbicides (initial results, FIG. 12B new results after 1 year, and FIG. 13—trial results on various rice lines).

Example 13: Crosses Between Mutant Lines Resistant to Different Herbicides

The cross between mutant line ML0831266-03093 (ATCC PTA-13620) carrying tolerance to mesotrione and possibly other HPPD inhibiting herbicides with mutant line ML0831265-01493 with (ATCC PTA-12933) tolerance to ACCase herbicides produced F1 seed inheriting both herbicide tolerances. Following selfing of the F1 plants F2, individuals are selected either through herbicide bioassays or alternatively with molecular markers. In the case of ACCase a functional molecular marker is described such that the mutation at position G2096S (based on the black grass numbering system) is selected. Furthermore using either markers linked to the QTLs on chromosome 1 and chromosome 2 or herbicide bioassays recovery of tolerance to mesotrione and ACCase including other HPPD herbicides or other herbicides.

Individuals selected for tolerance to mesotrione including other HPPD herbicides and possibly other herbicides may be used in a backcross conversion program or in breeding to develop new varieties and hybrids with a commercial level of tolerance to mesotrione and other herbicides. Selection with either bioassays or the chromosome 1 and chromosome 2 QTLs leads to the recovery of the inherent tolerance in P1003 along with the mutant tolerance for development of a novel variety or hybrid with herbicide tolerance and representing new weed control options in rice. The tolerance level of the mutant line is superior to other lines and allows for various commercial application methods.

The individual plants with tolerance to both herbicides are used in breeding to develop new varieties and hybrids with tolerance to both ACCase inhibiting herbicides, mesotrione, other HPPD inhibiting herbicides, and other herbicides. The new varieties and hybrids are commercial products. The commercial products are used commercially for rice production. In the production process both ACCase and mesotrione or other herbicides may be applied to the rice crop to control weeds. In one example mesotrione or other herbicides are applied preplant to control germinating weeds and provide residual weed control. Following germination of the rice crop ACCase herbicides are applied for controlling grass weeds. In another example both mesotrione or the equivalent is applied preplant and a second application is made post emergent along with an ACCase herbicide with one or two applications. In another example both mesotrione and an ACCase herbicide or other herbicides including other HPPD herbicides are applied post emergent with one or two applications. In this manner a new and novel strategy is implemented to provide full spectrum weed control in rice. In addition these herbicides have new not previously used in rice modes of action. This strategy therefore has commercial application not only for weed control but as a method to extend the useful life of this strategy and others through the application of multiple modes of action for weed control.

Example 14: Double Mutant Resistant to HPPD and ACCase Herbicides

A simple co-dominant marker assay is available to select for inheritance to ACCase herbicides derived from line ML0831265-01493. The marker is developed as a single nucleotide polymorphic marker and detects the causal mutation at position RTA1 (blackgrass number) for ACCase tolerance in line ML0831265-01493. All of the surviving plants following the mesotrione bioassay as employed in Example 11 are sampled for tissue collection, the DNA is extracted by known methods and the samples are tested with the SNP assay. A subset of the surviving plants are then also identified as carrying homozygous tolerance to ACCase herbicides through marker assisted selection.

In another embodiment the individuals with tolerance to both mesotrione and ACCase are used as trait donors in a backcross breeding program. After selecting one individual or a few individuals they will be used either as the pollinating parent or the female parent. Another more elite and desirable line serves as the recurrent parent to which the traits are transferred. Following the first cross the F1 plants are crossed again to the recurrent parent. The resulting backcross seed from this cross and ongoing crosses to the recurrent parent are tested with either markers or through herbicide bioassays for inheritance of the herbicide tolerance or a combination of markers and bioassays. In the best situation markers for the functional mutations are used. Alternatively an herbicide bioassay for mesotrione is applied to the BC seed or possibly the BC seed is progeny tested to verify inheritance of the tolerance. Furthermore an herbicide bioassay is used to identify individuals that also inherited tolerance to ACCase herbicides. This process is repeated until the recurrent parent genome is recovered along with the two new traits for tolerance to mesotrione and ACCase herbicides. After the last backcross individuals are selfed to recover the dual herbicide tolerances in a homozygous resistant level in at least one plant.

In yet another embodiment the individuals with resistance to both mesotrione and ACCase herbicides are crossed to a third line and subsequently selfed or even crossed with other lines. The resulting new lines and germplasm is tested and evaluated for other agronomic important traits. Finally new varieties or male and female lines are developed with tolerance to both mesotrione or other HPPD herbicides and ACCase herbicides a combination novel to rice.

Example 15: Full Spectrum Weed Control in Rice Based on Dual Resistance to Both ACCase and HPPD Herbicides In the production process both ACCase and mesotrione or other herbicides may be applied to the rice crop to control weeds. In one example mesotrione or other herbicides are applied preplant to control germinating weeds and provide residual weed control. Following germination of the rice crop ACCase herbicides are applied for controlling grass weeds. In another example both mesotrione is applied preplant and a second application is made post emergent along with an ACCase herbicide with one or two applications. In another example both mesotrione and an ACCase herbicide or other herbicides including other HPPD herbicides are applied post emergent with one or two application. In this manner a new and novel strategy is implemented to provide full spectrum weed control in rice. In addition these herbicides have not previously been used in rice modes of action. This strategy therefore has commercial application not only for weed control but as a method to extend the useful life of this strategy and others through the application of multiple modes of action for weed control.

Seed Deposits Under Budapest Treaty (see Tables 5 and 9)

Seed deposits by Ricetec Inc. were made with the American Type Culture Collection (ATCC), 10801 University Boulevard, Manassas, Va 20110, United States of America. The dates of deposit and the ATCC Accession Numbers are: ML0831266-03093 (PTA-13620, Mar. 19, 2013); ML0831265-01493 (PTA-12933, May 31, 2012); ML0831265-02283 (PTA-13619, Mar. 19, 2013); PL1214418M2-80048 (PTA-121362, Jun. 30, 2014), RL-1225468 (PTA-122646, Oct. 30, 2015), PL1214418M2-73009 (PTA-121398, Jul. 18, 2014) and 16USGE40004-34 (PTA-124233, Jun. 7, 2017). All restrictions will be removed upon granting of a patent, and the deposits meet all of the requirements of 37 C.F.R. §§ 1.801-1.809, and satisfy the Budapest Treaty requirements. The deposit will be irrevocably maintained in the depository for a period of thirty years, or five years after the last request, or for the enforceable life of the patent, whichever is longer, and will be replaced as necessary during that period.

DEFINITIONS

In the description and tables which follow, a number of terms are used. In order to provide a clear and consistent understanding of the specification and claims, including the scope to be given such terms, the following definitions are provided:

Acetyl-Coenzyme. A carboxylase (ACCase; EC 6.4.1.2) enzymes synthesize malonyl-CoA as the start of the de novo fatty acid synthesis pathway in plant chloroplasts. ACCase in grass chloroplasts is a multifunctional, nuclear-genome-encoded, very large, single polypeptide, transported into the plastid via an N-terminal transit peptide. The active form in grass chloroplasts is a homodimeric protein.

ACCase enzymes in grasses are inhibited by three classes of herbicidal active ingredients. The two most prevalent classes are aryloxyphenoxypropanoates ("FOPs") and cyclohexanediones ("DIMs"). In addition to these two classes, a third class phenylpyrazolines ("DENs") has been described.

Certain mutations in the carboxyl transferase region of the ACCase enzyme results in grasses becoming resistant to ACCase herbicides. In the weed Black-Grass at least five mutations have been described which provide resistance to FOP or DIM class of ACCase herbicides. Some mutations rendering ACCase enzymes resistant to these herbicides may be associated with decreased fitness.

Allele. Allele is any one of many alternative forms of a gene, all of which generally relate to one trait or characteristic. In a diploid cell or organism, the two alleles of a given gene occupy corresponding loci on a pair of homologous chromosomes.

Backcrossing. Process of crossing a hybrid progeny to one of the parents, for example, a first generation hybrid F1 with one of the parental genotypes of the F1 hybrid.

Blend. Physically mixing rice seeds of a rice hybrid with seeds of one, two, three, four or more of another rice hybrid, rice variety or rice inbred to produce a crop containing the characteristics of all of the rice seeds and plants in this blend.

Cell. Cell as used herein includes a plant cell, whether isolated, in tissue culture or incorporated in a plant or plant part.

Cultivar. Variety or strain persisting under cultivation.

Embryo. The embryo is the small plant contained within a mature seed.

Essentially all the physiological and morphological characteristics. A plant having essentially all the physiological and morphological characteristics of the hybrid or cultivar, except for the characteristics derived from the converted gene.

Grain Yield. Weight of grain harvested from a given area. Grain yield could also be determined indirectly by multiplying the number of panicles per area, by the number of grains per panicle, and by grain weight.

Injury to Plant. Is defined by comparing a test plant to controls and finding the test plant is not same height; an abnormal color, e.g. yellow not green; a usual leaf shape, curled, fewer tillers.

Locus. A locus is a position on a chromosome occupied by a DNA sequence; it confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Induced. As used herein, the term induced means genetic resistance appeared after treatment with mutagen.

Non-induced. As used herein, the term non-induced means genetic resistance not known to be induced; is at different location in the genome, than induced resistance.

Plant. As used herein, the term "plant" includes reference to an immature or mature whole plant, including a plant from which seed or grain or anthers have been removed. Seed or embryo that will produce the plant is also considered to be the plant.

Plant Part. As used herein, the term "plant part" (or a rice plant, or a part thereof) includes protoplasts, leaves, stems, roots, root tips, anthers, seed, grain, embryo, pollen, ovules, cotyledon, hypocotyl, glumes, panicles, flower, shoot, tissue, cells, meristematic cells and the like.

Quantitative Trait Loci (QTL). Genetic loci that controls to some degree numerically measurable traits that are usually continuously distributed. Recombinant/Non-Recombinant. If non-parental combination occur a rice patent is recombinant.

Regeneration. Regeneration refers to the development of a plant from tissue culture.

Resistance/Resistant[1]. The inherited ability of a plant to survive and reproduce following exposure to a dose of herbicide normally lethal to the wild type resistance may be naturally occurring or induced by such techniques as genetic engineering or selection of variants produced by tissue culture or mutagenesis.

[1] Weed Science Society of America, Weed Technology, vol. 12, issue 4 (October-December, 1998, p. 789)

Single Gene Converted (Conversion). Single gene converted (conversion) includes plants developed by a plant breeding technique called backcrossing wherein essentially all of the desired morphological and physiological characteristics of an inbred are recovered, while retaining a single gene transferred into the inbred via crossing and backcrossing. The term can also refer to the introduction of a single gene through genetic engineering techniques known in the art.

Stacking. Adding more than one thing to the same receiving entity. Methods of achieving the "stacked" state include: methods of vector-stack two or more genes in a single vector and do a single transformation to achieve stack; do sequential transformations into same receptor adding traits stepwise; achieve stacked hybrid simply by end crossing parentals carrying different traits; develop lines with multiple traits by sequential mutagenesis or crossing, and fixing the stacked state into one parent; and variants thereof.

Synergism. As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately."

The following equation may be used to calculate the expected resistance/tolerance in rice with combinations of mutations to herbicides, e.g., A and B:

Expected=$A+B-(A \times B/100)$

A=observed efficacy of mutation A at the same concentration of herbicide;

B=observed efficacy of mutation B at the same concentration of herbicide.

Synergistic in the herbicide context can mean that the use of herbicide results in an increased weed control effect compared to the weed control effects of A+B that are possible with the use of each herbicide alone. Or synergistic may be considered as the resistance/tolerance level of the rice, with combined mutations (stacked) compared to effects of a rice with a single mutation.

In some embodiments, the damage or injury to the undesired vegetation caused by the herbicide is evaluated using a scale from 0% to 100%, when compared with the untreated control vegetation, wherein 0% indicates no damage to the undesired vegetation and 100% indicates complete destruction of the undesired vegetation.

Tolerance/Tolerant. The inherent ability of a species to survive and reproduce after herbicide treatment implies that there was no selection or generic manipulation to make the plant tolerant.

Resistance/tolerance are used somewhat interchangeably herein; for a specific rice plant genotype information is provided on the herbicide applied, the strength of the herbicide, and the response of the plant.

This vector of closely linked mutations in combination with RTA1 (G2095) confers synergistic resistance to FOP herbicide.

TABLE 1A

Mutant Nucleotides Associated With ACCase Inhibitor Tolerant Rice RTA2

| Position | WT | MUT | Ind.

TABLE 1A-continued

Mutant Nucleotides Associated With ACCase Inhibitor Tolerant Rice RTA2

| | | | | | | |
|---|---|---|---|---|---|---|
| C1-33760496 | T | C | Y | | none | intergenic-Chr1 |
| C1-34079372 | C | CT | | Y | none | intergenic-Chr1 |
| C1-34374172 | G | A | Y | Y | none | intergenic-Chr1 |
| C1-34440547 | A | G | Y | | LOC_Os01g59560 | protein kinase domain containing protein, expressed |
| C1-34482064 | G | A | Y | Y | LOC_Os01g59620 | histone-lysine N-methyltransferase, H3 lysine-9 specific SUVH1, putative, expressed |
| C1-34680949 | G | A | Y | Y | LOC_Os01g59980 | zinc finger family protein, putative, expressed |
| C1-34801475 | T | C | Y | | LOC_Os01g60170 | DUF567 domain containing protein, putative, expressed |
| C1-34976760 | C | T | | Y | ? | ? |
| C1-35080808 | G | A | Y | | none | intergenic-Chr1 |
| C1-35498447 | G | A | Y | Y | LOC_Os01g61370 | expressed protein |
| C1-35645244 | G | A | Y | | none | intergenic-Chr1 |
| C1-35779866 | G | A | Y | Y | none | intergenic-Chr1 |
| C1-35800575 | G | A | Y | | none | intergenic-Chr1 |
| C1-35866927 | G | A | Y | | LOC_Os01g61950 | expressed protein |
| C1-36096211 | G | A | Y | | LOC_Os01g62370 | ENTH domain containing protein, expressed |
| C1-36160202 | G | A | Y | Y | LOC_Os01g62460 | ZOS1-16-C2H2 zinc finger protein, expressed |
| C1-36386713 | G | A | Y | Y | LOC_Os01g62820 | Transcription initiation factor TFIID subunit A containing protein, expressed |

| Position | Japonica_400 bp sequence (200 upstream, 200 downstream) | SEQ ID NO: |
|---|---|---|
| C1-32083963 | gccggcgcagcgagaagagtgccgaatgttggatggaggacgccgaagcgcgggaaggtcatggtggcggcgttctggctccgtccacgtcggactagcgacgcggtcgacgaccctgtgctgcatcctaccatgccaactttgcgtatccgtcggcgtccatcttcgccaggatgccggggaaggagaagaagaggcggcggcgaggccgaagaggcgaggataggatgaggtggcggaggagggcgtgggagggaggcagcgagctcccgccgccccgtcactcctgccgctctcgtcgcccgccattccgccgagcttccgccgcccgtcgttcccgccgcccgccattccgccactccgccgagctcccgccgcccgcctctcccgc | 38 |
| C1-32165584 | acgcgcgcgcctccattgttctcggatcaacaagctctccaagaacagcagcaaagatgaagccttcgtcttcctccgtcggcgtctgtaccctgctggtggcggtggcctccctgcagctcctcctcgtcgtcgccgtcgccgcctcggcgaagactgcaccggcgatgccagacgaggagttcttgggccgtctctgcgaccagcagcaggggccacgcggcggcggctcccgtggtgccagcagctgcacgcgaggcggcgccacggcggtggcggcggcggcgtcggcgtcggcaagcggcggcgggtgccgatgccgccgcccagccgcgccggcgaggagatcgacgcgcgctacgacgtgtccaagcgggtcgtgccgagcggaccgaacccg | 39 |
| C1-32177487 | ttttggggtcttcccttcttattttccctgagcgtagaaaattctgtggtttccagttttccacggaagtaaattccaattttccaatagatgtacgtcaacccttgcttcctctccagctgcagagttgcaggtttgacgaatgcagcttatctacaaaattcccatcagagggaacacagttacagaagaactaggggaagtacagattgcaaatccataaggatcttcttagaaccgtatacgtaaagggcttcatggattggccactatatatgggtgtcaccctcaatcgtgaatctgcaaggtcagatatcagtatatcaaatgcagattgcctcattgcagattgctgtggattgttcaggttccgggttagcccagtcaccagtcttcact | 40 |

TABLE 1A-continued

Mutant Nucleotides Associated With ACCase Inhibitor
Tolerant Rice RTA2

| C1-32459172 | ccacgcgagcagctggtgtttgctcatggtggcagtggtgcgcgataccagtagcgtgcgc gacgcgtcggggtggtcatcggcgagggcgagcatgtcgtcgtccagtggacgcggactct agggtgatcacgctcggccctgtcacgctcaaaacaatactacggcacatctgattacgtt gacaggatctgagaccacaccagaactatcccattccgatcatgcatgtgaaaaa TABLE 1A-continued Mutant Nucleotides Associated With ACCase Inhibitor
Tolerant Rice RTA2

| C1-34440547 | tagcagcagatgtcatacaaacaggctttcattggaagcaataaaaatagtggacatcca aaagatgtgtggaactatgacttctagatatcacaggcatctagcatcttgattttattcaa gactgcacataacatctttacattctagagggaaatgatccgacttaagtagtttgatagtt cacctcagggaggaagtcctttgatagtgttatagatgtctcccgaagcaccttgactgcca cttcctctccattgtccaatatgccatgataaaccataccaaatcctccttttccaatgatag actggaagttgttagttatagtcttcaactctgtatatgtgaatcttctggtgtcagtatgcag gggagtatcctcttcatacatatcata | 50 |
| --- | --- | --- |
| C1-34482064 | gtttgggcaccgacagctccaacggaacaaagaaacgccctaagacctctaataggaag gctgctactgacaatgagatttccttgatgcctccatccagcgatcccagggaggttgtgga agtgcttctcatgaccttcgaggcactgcggcgtaggcatcttcaattggatgagacacaa gagactagcaaacgtgcagacctgaaggctggtgccatcatgttggccagtaatctgagg gctaacattgggaagaggattggagctgtccctggagttgaagtagggatattttctactt caggatggagctatgcattatcggcttgcatgcacctagcatgggtggaattgattatatga ataagtttggtgatgaggatgactctgtagcaata | 51 |
| C1-34680949 | aatgaggaaaggtgagaatcggtttgttattagtaagaagaaagaccgctcactgacatc gccacagtacaaaaggcgcagtgtgctcgagcatgctgataattccaatttcatcccatttg tcccattccctcctgattacttttgccaagaaaaataagcctgtggagaattcatcagatgca ggaatagtgccagaaggccctccatcagctgaaaaattaccagaaacaaaatattcatct ggaaatctgggaaattttcagaacagctcacaggtgatgggcagtcaggcagcaaacaac atgaacaatgagaacaggaacgaaattatccacatcaaaacttgagtacaagtggttat gggtatggtgaaagcatcacttatcagcatcaaccac | 52 |
| C1-34801475 | tgatttggttgatttgtgggcgcgcgcgcgcatggcgaaggtacatcctaacgtggtgcccg tggcggcggcggcagggccggccggcggcgagcggcggggggaggaggaggaggagg cggcggcgctgacggtgtggcggaagtcgctgctgttcaactgcaaggggttcacggtgtt cgacgccaaggggaacctggcgtaccgcgtcgacagctacgacacggagagcggcgacg aggtcgtcctcatggacgccgccgccgcgccccggccttcaccgtccgcaggaagaggcagc tcagcctgcaggggagcagtggctcgttcgccggcgaggcggacggccggcggccgc ccgtgtacgcggtcaggcggacgggccgcggcggcggcaagt | 53 |
| C1-34976760 | aaaaaatatggtttcaaagttttccaaatcggtaaatctaattggagaggcctctccaatta gtcttaaccagagacacccacgtgctagtacttaggagttttggttgctattaatcgattga gcaagtaggggaaatattcctatcatctatgcttcaaataaagttttctcttaaattactcat ccgatttacaatccgattacaccgttgtgttcgtaataattaaatctttacaacaagatctca catgattatattttgatgaaaaatcacaaattacttttatgatatgtctaaattacttttagat ttcactaagttacttcttagacatataaagtaaattcagtaaagcctaaaagtaattacat atattatagcagtaacttataaca | 54 |
| C1-35080808 | aacgtcgacgagaaccgggctcccaactgacggtcacgcgagagctgcacgaaacgagc ctcgacgacgatcccatccgtccgtccgtcgctgcggctgctgctgctgccgccacaggcgg tcagagcctctggcacgatgccaacacgcgggcacgtggtagggcagcacgggccattca ggtggtgtttggatccagggacttaactttattctctatatttagacactaatttaaaatatta aatatagattacttacaaaactaattacataaatgaaagctaatttgtgtgataactttttta agcttaattaatccataattagagaatgtttaatgtagcatcacataagctaatcatggatt aattaggctcaatagattcgtctcgcgaatt | 55 |
| C1-35498447 | cgtccgccgaagcgcacgaccggcgcggcgtggggagcggcgagtcgagcagctgcggg agcttctcgccgtcggcgccattgcaccgcagcccctccttgtccgcgcctggtgacgatttcc atgggcattgcgccgactgactgtgtcggcagcatgcatcgtctcggcgttcaacgtgtgg aggggacgacgtataagagtacacgcgaagactgtaggtagaggtgcttttcccgcgaaa agtggcagtagcggcggttggacagtaaccttcgtgtatggttgtgtgttcatctcacgtact gttcttttgcctctcgctagctcgttcccgtgatcaaggtgcatgctcgatggccttaatggtg gaggttgccgaaaggtagcagaggaaatca | 56 |
| C1-35645244 | ggatggatagtaaatataatatgaattgatctattggatcagttatatatatatatatatata tatatatatatatatatatatatatatagacacacacacacacaatgaggatggta aattagtgacaatatatgaatgtgttctattgtcaaaacgaaagggatcgatgagttatatc tctaggttaattagtttacaacgaagagttgaagctggaataaacaagtcaaaattatatct gtataacatcatagtaatgccgaccatgtacgcatccacatgccatacagcaacatcaga aacagaatttaattaattatttgactaaacccagaatcatttgctgctgcatcgaatcgttcc tctcgtcatcgccgacgcaaacatgcgc | 57 |
| C1-35779866 | ctatgagttagctagctaacgtgtatgatgtccaatgattaagtgacacttttttctgtctaa tataatcatccatctcatcatatcattagctccttgtgcttgtgcgttcactgttcagagaagc tggttatcctccctgataagaacagccgggaggcagtgtgctatggttttgtttagttctgg aatgatccagtcacccagcacaattgactggctgagtgttgcattaagcaaatctggaccg gatttgagggaattttctcgcgcagtggagatctatgataaatctcgtaccgatccagcata gtgattcgtccgcgggattaatactgtaactaatccatagattagcgccattattgaaacac gctttcttcttattgttgttattat | 58 |

TABLE 1A-continued

Mutant Nucleotides Associated With ACCase Inhibitor Tolerant Rice RTA2

| | | |
|---|---|---|
| C1-35800575 | actctgtagtctgcaaggagcggttggcgagcagtggcgcgcgaagtcgataggggtggcga gcggacggagtggcgacggagagcctgcgggagtcgagatcgtccggggaagcaacgac ggcaacgacggcagccttgtatcccgtcggcgaggtcacgctcggccattgcgcacctctc ccttcgcccatcgccatcgagccccacccacggcgcccggccatcccggcgaggagctc tgtttttggtgggtgtcggcggagttggaacgaaggagggtcgttctcggcatcgatgtcgc catctccgatcctccaccgccaccgccgccctccccccctccattgccgaccccctccccggc gtcgagaaaatcctcgcccgacctcagcaacaagaa | 59 |
| C1-35866927 | tagactgcatcgccacctgccgccgaactgcgccgctgctgccgcccgccggtgccctctcct tcacctcccgctgcatcgccgcctgccgccaagcgcacggcgaagggtaaggagtcgtgg cggcgcgggcgctcatggcggtggaggacctgctggatgttgctgctcctgttctcgccat tgtcggagtcggcgccgccacgccgacggagaatctcaaggaggcgatgagcacgccg aggctcggacccagcttcgtcggtgggacaaagcgggactcgatggagacggtggagctc tcctcctcctcccccaacaccacctcatgtagcttccccctcggcgcgtcagtaggtaggggt atccatcgcttgtgcagctgcaccgagtcctcatc | 60 |
| C1-36096211 | tcctggaggatgagcgtgagcgtgcgcgcaagatagcgcacgagatcaagggattcggca gcttcaacctcagcagcgcgcatgcgtcggggtcggcggcggcagccctccgcgcggggg cgatggagcaccagtgctacggccggacgcaactcgcggtacgagggcaggtggaggagg gaggcctgcgtggacgacggcgacaaggagaacctgctggtggtgtcgatggccgaggc gaaggccgaggcggcggcggaggagccgcaccactaccaccacccgttctacggcttcgg gcagcagcggccggaggcgatgctgctcctgagccagtagtgatcgtttgggtggatggtt cttcgtcgatcgcatcgttcgttggtttgtgatgcgtgagaa | 61 |
| C1-36160202 | agtctgtggccactgatgacaggcgcagtgcaactgagctcctgaagcagatcaggcagc atgctcatgccaatggtgatggtgatcagcgtttggcacactgcttcgccaacggcctcgag gcgaggctggcaggtactggtagtcaaatttacaagaactacacgataactcggcttccat gcactgatgtgctgaaagcgtaccagctttatttggcagcttgcccattttaagaagatctctc attactttgccaatcaaacaattttgaatgctgtggagaaggccaagaaagttcacattgtc gattatggcatatactatggatttcagtggccgtgtcttattcagcggctatctaacaggcct ggaggcccaccaaagcttaggatcactgga | 62 |
| C1-36386713 | gggcattggtgaaggctcagtaaccggaggtcttgtttgatggttggcaactgaattgttaa ttaccaatttatttcctgtgcttctaataccagcagcatcacattctggttgttgagggtccac tgataccttttacctgttgcagttttatttgttttaaataatccaatcaaacttttgtttgagcttatt gctgaatagcacagcagcagtacatgcaatgcaagatgcccagatgatgagaataaagg caatggcaaaaatataagtgctagttctcatttcaaaataacaaacagacaacattgcattc taaactttttataaccaaacaaacaaaggaaacagggaaaattgctgaattaatgttccctt tactaagtaaattctactagaaagcact | 63 |

TABLE 1B

Mutant Nucleotides Associated with ACCase inhibitor Tolerant Rice RTA2[2]

| Position | WT | MUT | Ind. Ref | Ja. Ref | Gene ID | Annotation |
|---|---|---|---|---|---|---|
| C1-27445918 | A | G | | Y | ? | ? |
| C1-27537999 | G | A | | | none | intergenic-Chr1 |
| C1-27744352 | G | A | Y | Y | ? | ? |
| C1-27747559 | AG | A | | Y | ? | ? |
| C1-27747561 | G | A | Y | | LOC__Os01g48420 | peroxiredoxin, putative, expressed |
| C1-27747563 | A | . | | Y | ? | ? |
| C1-27792734 | T | . | | Y | ? | ? |
| C1-28257622 | G | A | Y | Y | ? | ? |
| C1-28651555 | A | G | Y | | LOC__Os01g49880 | expressed protein |
| C1-28651826 | A | G | Y | | LOC__Os01g49880 | expressed protein |
| C1-29226560 | G | A | Y | | LOC__Os01g50880 | hypothetical protein |
| C1-29278751 | G | A | Y | Y | ? | ? |
| C1-29340100 | G | A | Y | | ? | ? |
| C1-29875869 | G | A | Y | | ? | ? |
| C1-30173016 | T | C | | Y | ? | ? |
| C1-30198493 | G | A | Y | Y | ? | ? |
| C1-30224991 | G | A | Y | | none | intergenic-Chr1 |
| C1-30225002 | C | T | Y | | none | intergenic-Chr1 |
| C1-30225285 | T | C | Y | | none | intergenic-Chr1 |
| C1-30429097 | G | A | Y | Y | ? | ? |
| C1-30628125 | G | A | Y | Y | ? | ? |
| C1-30682702 | G | A | Y | | none | intergenic-Chr1 |
| C1-30876818 | G | A | Y | Y | ? | ? |
| C1-30927957 | G | A | Y | | none | intergenic-Chr1 |
| C1-31291611 | G | A | Y | Y | ? | ? |
| C1-31375767 | T | A | | Y | ? | ? |
| C1-31549407 | G | A | Y | Y | ? | ? |

TABLE 1B-continued

Mutant Nucleotides Associated with ACCase inhibitor Tolerant Rice RTA2[2]

| Position | WT | MUT | Ind. Ref | Ja. Ref | Gene ID | Annotation |
|---|---|---|---|---|---|---|
| C1-31671724 | T | C | Y | Y | none | intergenic-Chr1 |
| C1-31671725 | A | G | Y | | none | intergenic-Chr1 |
| C1-32083963 | C | T | Y | | none | intergenic-Chr1 |
| C1-32165584 | G | A | Y | | LOC_Os01g55850 | expressed protein |
| C1-32177487 | G | A | Y | Y | ? | ? |
| C1-32459172 | T | C | Y | | none | intergenic-Chr1 |
| C1-32785958 | A | G | | Y | ? | ? |
| C1-32821747 | T | C | Y | | none | intergenic-Chr1 |
| C1-33147227 | G | A | Y | Y | LOC_Os01g57350 | diacylglycerol kinase, putative, expressed |
| C1-33201871 | C | T | Y | Y | none | intergenic-Chr1 |
| C1-33760443 | T | C | Y | | none | intergenic-Chr1 |
| C1-33760496 | T | C | Y | | none | intergenic-Chr1 |
| C1-34079372 | C | CT | | Y | none | intergenic-Chr1 |
| C1-34374172 | G | A | Y | Y | none | intergenic-Chr1 |
| C1-34440547 | A | G | Y | | LOC_Os01g59560 | protein kinase domain containing protein, expressed |
| C1-34482064 | G | A | Y | Y | LOC_Os01g59620 | histone-lysine N-methyltransferase, H3 lysine-9 specific SUVH1, putative, expressed |
| C1-34680949 | G | A | Y | Y | LOC_Os01g59980 | zinc finger family protein, putative, expressed |
| C1-34801475 | T | C | Y | | LOC_Os01g60170 | DUF567 domain containing protein, putative, expressed |
| C1-34976760 | C | T | | Y | ? | ? |
| C1-35080808 | G | A | Y | | none | intergenic-Chr1 |
| C1-35498447 | G | A | Y | Y | LOC_Os01g61370 | expressed protein |
| C1-35645244 | G | A | Y | | none | intergenic-Chr1 |
| C1-35779866 | G | A | Y | Y | none | intergenic-Chr1 |
| C1-35800575 | G | A | Y | | none | intergenic-Chr1 |
| C1-35866927 | G | A | Y | | LOC_Os01g61950 | expressed protein |
| C1-36096211 | G | A | Y | | LOC_Os01g62370 | ENTH domain containing protein, expressed |
| C1-36160202 | G | A | Y | Y | LOC_Os01g62460 | ZOS1-16 - C2H2 zinc finger protein, expressed |
| C1-36386713 | G | A | Y | Y | LOC_Os01g62820 | Transcription initiation factor TFIID subunit A containing protein, expressed |
| C1-36447011 | G | A | Y | Y | LOC_Os01g62920 | homeodomain protein, putative, expressed |
| C1-36630547 | G | A | Y | | none | intergenic-Chr1 |
| C1-36669757 | A | G | Y | | ? | ? |
| C1-36747244 | G | A | Y | Y | LOC_Os01g63420 | OsFBL4 - F-box domain and LRR containing protein, expressed |
| C1-37318473 | G | A | Y | Y | LOC_Os01g64280 | sorting nexin 1, putative, expressed |
| C1-37381689 | G | A | Y | | ? | ? |
| C1-37756353 | A | G | Y | | ? | ? |
| C1-37770409 | G | A | Y | Y | LOC_Os01g65070 | hydrolase, alpha/beta fold family domain containing protein, expressed |
| C1-37790329 | G | A | | Y | LOC_Os01g65100 | peptide transporter, putative, expressed |
| C1-37896676 | G | A | Y | Y | LOC_Os01g65320 | expressed protein |
| C1-38439735 | A | G | Y | | ? | ? |
| C1-38439976 | A | G | Y | | ? | ? |
| C1-38471485 | G | A | Y | Y | LOC_Os01g66230 | csAtPR5, putative, expressed |
| C1-39383231 | G | A | Y | Y | none | intergenic-Chr1 |
| C1-39481120 | A | G | Y | | ? | ? |
| C1-39495966 | T | C | | Y | LOC_Os01g67970 | ZOS1-20 - C2H2 zinc finger protein, expressed |
| C1-39500910 | G | A | Y | | ? | ? |
| C1-39639526 | G | A | | Y | LOC_Os01g68200 | expressed protein |

[2]Includes the shorter version in Table 1A.

TABLE 2

Phenotypic characteristics of a mutant rice line showing resistance to mesotrione, with comparison to the original unmutated parent line.

| Designation | Days to 50% Heading | Plant Height | Plant Type | Pubesence | Sheath Color | Awns | TKW, g | yield/plant |
|---|---|---|---|---|---|---|---|---|
| Unmutated parent line | 85 | 96.5 | erect | glaborous | purple inside sheath | None | 23.15 | N/A |
| ML0831266-03093F2 | 82 | 94 | erect | glaborous | purple inside sheath | None | 24.55 | 4.5 |

TABLE 3

Numbers of tolerant plants after three different herbicide bioassays applied to an F2 individuals derived from a cross of ML0831266-03093 with tolerance to mesotrione and ML0831265-01493 with tolerance to ACCase inhibiting herbicides.

| Parameters | Single application of mesotrione at 105 gai/ha | | Single application of mesotrione at 420 gai/ha | | One application of mesotrione at 105 gai/ha followed by second application of 630 gai/ha | |
|---|---|---|---|---|---|---|
| | Tolerant | Susceptible | Tolerant | Susceptible | Tolerant | Susceptible |
| Observed (o) | 64 | 23 | 26 | 52 | 28 | 67 |
| Expected (e) | 21.75 | 65.25 | 19.5 | 58.5 | 23.75 | 71.25 |
| Deviation (o-e) | 42.25 | -42.25 | 6.5 | -6.5 | 4.25 | -4.25 |
| Deviation (o-e)$^2$ | 1785.06 | 1785.06 | 42.25 | 42.25 | 18.06 | 18.06 |
| (o-e)$^2$/e | 82 | 27.35 | 2.166 | 0.722 | 0.76 | 0.253 |
| Chi-Square Value | 109.35 | | 2.88 | | 1.013 | |
| Degrees of freedom (df) | 1 | | 1 | | 1 | |
| Probability value | | | 0.08919242 | | 0.31393809 | |
| Critical Chi-Square value at p = 0.05 | 3.84 | | 3.84 | | 3.84 | |

TABLE 4

ACCase mutation RTA2-QTL start and end SNP marker sequences

| ID | Chromo-some | Upstream sequence | Allele | Downstream sequence | SEQ ID NO: |
|---|---|---|---|---|---|
| id1019752 | 1 | ataaagatgaggtgtttgatgaattaaaggccg cagggttgaagaggccatgtagctttacagata tttccagtgaaaatgattgcttcttgaatttga | g/t | acagcaactgatgcagctgagcgaaagcccat attaggcgccagcttcatccagatgtagttcc caggacaagaatacttaggtcatgaacttttg | 64 |
| id1025754 | 1 | tcacatgatctgcaactgtcaacagtcttaccg gaattggattctgaaggtggatactccacctgt ccaccataagtccttatttgtcagaggttacaat | t/c | gcatgatgtgtctatactctatactgcaaagat agaatactacaagttttcttgggcttaaaagaa gaaaaactaggaacagcctcactagtttgctag | 65 |

TABLE 5

Summary of rice lines cited herein (see also Table 9)

| LINE | TRAIT RESISTANCE/ TOLERANCE TO INHIBITORS[3] | ATCC DEPOSIT AND DATE ISSUED |
|---|---|---|
| P1003 | HPPDni | |
| R0146 | NONE | |
| ML0831266-03093 | HPPDi + HPPDni | PTA-13620 Mar. 19, 2013 |
| ML0831265-01493 | RTA1 | PTA-12933 May 31, 2012 |
| ML0831265-02283 | RTA2 | PTA-13619 Mar. 19, 2013 |
| PL1214418M2-73009 | RTA1 + HPPDi + HPPDni | PTA-121398 Jul. 18, 2014 |
| PL1214418M2-80048 | RTA1 + HPPDi + HPPDni | PTA-121362 Jun. 30, 2014 |
| RL1225468 | RTA1 + RTA2 | PTA-122646 Oct. 30, 2015 |
| PL1214418M2-73001 | RTA1 + HPPDi | |
| PL1214418M2-73013 | RTA1 + HPPDni | |

[3]HPPDi = induced HPPD inhibitor tolerance/resistance associated with a change in a genetic region induced chemically.
HPPDni = natural tolerance/resistance to HPPD inhibitors.
RTA1 = substitute G2096S in ACCase enzyme due to mutation, associated with tolerance to ACCase inhibitors.
RTA2 = see Tables 1A and 1B.

TABLE 6

Agronomic characteristics of two lines carrying both HPPD and ACCase resistance/tolerance (RTA1 + HPPDi + HPPDni).

| Designation | Days to 50% Heading | Plant Height | Plant Type | Pubesence | Sheath Color | Awns | yield/plant |
|---|---|---|---|---|---|---|---|
| PL1214418M2-80048 | range 56-94 | range 57-80 cm | erect to intermediate | variation of glaborous and smooth | variation between green and purple | None | 13.39 gm |

TABLE 6-continued

Agronomic characteristics of two lines carrying both HPPD and ACCase resistance/tolerance (RTA1 + HPPDi + HPPDni).

| Designation | Days to 50% Heading | Plant Height | Plant Type | Pubesence | Sheath Color | Awns | yield/plant |
|---|---|---|---|---|---|---|---|
| PL1214418M2-73009 | 85 | range 84-108 cm | erect to intermediate | variation of glaborous and smooth | variation between green and purple | None | NA |

TABLE 7

Herbicide Injury Rating Scale in Rice

| Score | Rating description |
|---|---|
| 0 | no visible injury |
| 1 | injury observed in at least 1 plants but very minimal |
| 5 | minimal injury observed across plot |
| 10 | plants are stunted 10% as compared to control, or plants show herbicide injury on approximatly 10% of leaf area in the plot |
| 15 | plants are stunted 15% as compared to control, or plants show herbicide injury on approximatly 15% of leaf area in the plot |
| 20 | plants are stunted 20% as compared to control, or plants show herbicide injury on approximatly 20% of leaf area in the plot |
| 25 | plants are stunted 25% as compared to control, or plants show herbicide injury onapproximatly 25% of leaf area in the plot |
| 30 | plants are stunted 30% as compared to control, or plants show herbicide injury onapproximatly 30% of leaf area in the plot |
| 35 | plants are stunted 35% as compared to control, or plants show herbicide injury on approximatly 35% of leaf area in the plot |
| 40 | plants are stunted 40% as compared to control, or plants show herbicide injury onapproximatly 40% of leaf area in the plot |
| 45 | plants are stunted 45% as compared to control, or plants show herbicide injury on approximatly 45% of leaf area in the plot |
| 50 | plants are stunted 50% as compared to control, or plants show herbicide injury on approximatly 50% of leaf area in the plot |
| 55 | plants show herbicide injury on approximatly 55% of leaf area in the plot |
| 60 | plants show herbicide injury on approximatly 60% of leaf area in the plot |
| 65 | plants show herbicide injury on approximatly 65% of leaf area in the plot |
| 70 | plants show herbicide injury on approximatly 70% of leaf area in the plot |
| 75 | plants show herbicide injury on approximatly 75% of leaf area in the plot |
| 80 | plants show herbicide injury on approximatly 80% of leaf area in the plot |
| 85 | plants show herbicide injury on approximatly 85% of leaf area in the plot |
| 90 | plants show herbicide injury on approximatly 90% of leaf area in the plot |
| 95 | All plants severly injured, most are dead. Some green tissue spread throughout plot. |
| 99 | nearly all plants are dead, but at least 1 plant has green tissue. |
| 100 | all plants dead and brown. No green tissue in the plot. |

TABLE 8

Reference Herbicide Products used, and Doses

| Product name | Active Ingredient | Active Ingredient Concentration | Prod Conc Unit | Use rate units | 1X | 2X | 4X |
|---|---|---|---|---|---|---|---|
| Assure II | Quizalofop | 10.54 | gm ai/100 ml | g ai/ha | 77 | 154 | 308 |
| Assure II | Quizalofop | 10.54 | gm ai/100 ml | oz/acre | 10 | 20 | 40 |
| Fusilade DX | Fluazifop | 23.96 | gm ai/100 ml | g ai/ha | 210 | 420 | 840 |
| Fusilade DX | Fluazifop | 23.96 | gm ai/100 ml | oz/acre | 12 | 24 | 48 |
| proprietary | Propaquizafop | 10 | gm ai/100 ml | g ai/ha | 100 | 200 | 400 |
| proprietary | Propaquizafop | 10 | gm ai/100 ml | oz/acre | 13.7 | 27.4 | 54.7 |
| Callisto | mesotrione | 47.93 | gm ai/100 ml | g ai/ha | 210 | 420 | 840 |
| Callisto | mesotrione | 47.93 | gm ai/100 ml | oz/acre | 6 | 12 | 24 |
| Command | Clomazone | 35.9 | gm ai/100 ml | g ai/ha | 315 | 630 | |
| Command | Clomazone | 35.9 | gm ai/100 ml | oz/acre | 12 | 24 | |

TABLE 9

Rice Seed Deposits Under the Budapest Treaty (see also Table 5)

| Deposited Lines | PTA No. | Parental Source | Other Data |
|---|---|---|---|
| RL1225468 | PTA-122646 | R0146 stacked mutant donor | RTA1-RTA2 |
| 16USGE40004-34 | PTA-124233 | R0146 Conversion | RTA1-RTA2 |
| ML0831265-01493 | PTA-12933 | R0146 RTA1 mutant donor | RTA1 |
| ML0831265-02283 | PTA-13619 | R0146 RTA2 mutant donor | RTA2 |
| ML0831266-03093 | RTA-13620 | | HPPDi/ni |

PUBLICATIONS

All publications cited in this application are herein incorporated by reference to the extent they relate materials and/or methods related to the invention Agarwal et al., Plant Mol Biol (2007) 65:467-485. *Genome-wide identification of C2H2 zincfinger gene family in rice and their phylogeny and expression analysis*

Akira, Abe et al., *Genome sequencing reveals agronomically important loci in rice using MutMap Nature Biotechnology* 30, 174-178 (2012), Published online 22 Jan. 2012.

Wright, Mark H. et al., *Genome-wide association mapping reveals a rich genetic architecture of complex traits in Oryza sativa. Nat. Comm* 2:467|*DOI*: 10.1038/ncomms1467, *Published Online* 13 *Sep.* 2011. The marker information can be accessed from The Rice Diversity Home Page and downloading the file "44K GWAS Data"

Zhao, Keyan et al. (2011). *Genome-wide association mapping reveals a rich genetic architecture of complex traits in Oryza sativa. Nat Comm* 2:467|DOI: 10.1038/ncomms1467, Published Online 13 Sep. 2011

---

The invention claimed is:

1. A rice plant with a genome associated with tolerance to ACCase inhibitors, at herbicide dosages at a level significantly higher than that tolerated by rice plants without the genome, wherein the genome comprises a combination of a mutation in chromosome 5 and a genetic region in chromosome 1, and wherein the tolerance is synergistic compared to tolerance predicted from the additive response of the mutation in chromosome 5 and the genetic region of chromosome 1 and wherein the genome comprises:
   a) the mutation in chromosome 5 that encodes a G2096S substitution in an amino acid sequence of an ACCase enzyme that comprises SEQ ID NO: 3; and
   b) the following nucleotide sequences in the genetic region of chromosome 1 wherein each sequence has a single mutation:
   SEQ ID NO: 38;
   SEQ ID NO: 39;
   SEQ ID NO: 40;
   SEQ ID NO: 41;
   SEQ ID NO: 42;
   SEQ ID NO: 43;
   SEQ ID NO: 44;
   SEQ ID NO: 45;
   SEQ ID NO: 46;
   SEQ ID NO: 47;
   SEQ ID NO: 48;
   SEQ ID NO: 49;
   SEQ ID NO: 50;
   SEQ ID NO: 51;
   SEQ ID NO: 52;
   SEQ ID NO: 53;
   SEQ ID NO: 54;
   SEQ ID NO: 55;
   SEQ ID NO: 56;
   SEQ ID NO: 57;
   SEQ ID NO: 58;
   SEQ ID NO: 59;
   SEQ ID NO: 60;
   SEQ ID NO: 61;
   SEQ ID NO: 62; and
   SEQ ID NO: 63;
   wherein the sequences include 200 bp upstream and 200 bp downstream of each specific mutation, wherein the single mutation in each sequence is in position 201.

2. A seed from the rice plant of claim 1.

3. The rice plant of claim 1 wherein the mutation in the genetic region of chromosome 1 is A instead of G in SEQ ID NO: 62 at position 201 within the sequence.

4. A rice plant having genetic material encoding the amino acid substitution G2096S in an ACCase enzyme and having a genetic region of chromosome number 1 comprising nucleic acids with SEQ ID Nos.: 38 to 63, derived from rice seeds selected from ATCC deposits with accession number PTA-122646 or 124233.

5. The rice plant of claim 1 with at least one of the nucleotide sequences in the genetic region of chromosome 1.

6. A rice seed selected from a sample of seed deposited under ATCC Accession No. PTA-122646 and 124233.

7. A rice plant, or a part thereof, produced by growing the seed of claim 6.

8. Pollen or an ovule of the plant of claim 7.

9. A tissue culture produced from protoplasts or cells from the rice plant of claim 7 wherein said cells or protoplasts of the tissue culture are produced from a plant part selected from the group consisting of leaves, cotyledon, hypocotyl, meristematic cells, roots, root tips, pistils, flowers, stems, glumes and panicles.

10. A protoplast produced from the plant of claim 7.

11. A method for producing a herbicide tolerant rice seed, wherein the method comprises crossing the plant of claim 7 with a rice plant that lacks the amino acid substitution G2096S in the ACCase enzyme and the genetic region of chromosome number 1 with nucleotide sequences SEQ ID NOS.: 38-63 and selecting a progeny from the cross that exhibits herbicide tolerance.

12. An herbicide resistant rice plant produced from a seed of the progeny produced by the method of claim 11, wherein the rice plant comprises the amino acid substitution G2096S in the ACCase enzyme and the genetic region of chromosome number 1 with nucleotide sequences SEQ ID NOS.: 38-63.

13. The rice plant of claim 12 that is tolerant to ACCase inhibitors, at levels higher than those tolerated by plants without the combined genomes of the rice lines with ATCC deposits with accession number PTA-122646 or 124233 that confer herbicide tolerance.

\* \* \* \* \*

SEQUENCE LISTING

<160> NUMBER OF SEQ ID NOS: 65

<210> SEQ ID NO 1
<211> LENGTH: 2501
<212> TYPE: DNA
<213> ORGANISM: Oryza sativa

<400> SEQUENCE: 1

```
cctgttctgc taggaataat agaactacat actgctatga ttttccactg gtgagttgac    60
tgctccctta tattcaatgc attaccatag caaattcata ttcgttcatg ttgtcaaaat   120
aagccgatga aaattcaaaa ctgtaggcat ttgaaactgc agtgaggaag tcatggtcct   180
ctagtacctc tggtgcttct aaaggtgttg aaaatgccca atgttatgtt aaagctacag   240
agttggtatt tgcggacaaa catgggtcat ggggcactcc tttagttcaa atggaccggc   300
ctgctgggct caatgacatt ggtatggtag cttggacctt gaagatgtcc actcctgaat   360
ttcctagtgg tagggagatt attgttgttg caaatgatat tacgttcaga gctggatcat   420
ttggcccaag ggaagatgca tttttttgaag ctgttaccaa cctagcctgt gagaagaaac   480
ttcctcttat ttatttggca gcaaattctg gtgctcgaat tggcatagca gatgaagtga   540
aatcttgctt ccgtgttggg tggtctgatg atggcagccc tgaacgtggg tttcagtaca   600
tttatctaag cgaagaagac tatgctcgta ttggcacttc tgtcatagca cataagatgc   660
agctagacag tggtgaaatt aggtgggtta ttgattctgt tgtgggcaag gaagatggac   720
ttggtgtgga gaatatacat ggaagtgctg ctattgccag tgcttattct agggcatata   780
aggagacatt tacacttaca tttgtgactg gaagaactgt tggaatagga gcttatcttg   840
ctcgacttgg catccggtgc atacagcgtc ttgaccagcc tattattctt acaggctatt   900
ctgcactgaa caagcttctt gggcgggaag tgtacagctc ccacatgcag ttgggtggtc   960
ccaaaatcat ggcaactaat ggtgttgtcc atcttactgt ttcagatgac cttgaaggcg  1020
tttctaatat attgaggtgg ctcagttatg ttcctgccta cattggtgga ccacttccag  1080
taacaacacc gttggaccca ccggacagac ctgttgcata cattcctgag aactcgtgtg  1140
atcctcgagc ggctatccgt ggtgttgatg acagccaagg gaaatggtta ggtggtatgt  1200
ttgataaaga cagctttgtg gaaacatttg aaggttgggc taagacagtg gttactggca  1260
gagcaaagct tggtggaatt ccagtgggtg tgatagctgt ggagactcag accatgatgc  1320
aaactatccc tgctgaccct ggtcagcttg attcccgtga gcaatctgtt cctcgtgctg  1380
gacaagtgtg gtttccagat tctgcaacca agactgcgca ggcattgctg gacttcaacc  1440
gtgaaggatt acctctgttc atcctcgcta actggagagg cttctctggt ggacaaagag  1500 atcttttttga aggaattctt caggctggct cgactattgt tgagaacctt aggacataca  1560
atcagcctgc ctttgtctac attcccatgg ctgcagagct acgaggaggg gcttgggttg  1620
tggttgatag caagataaac ccagaccgca ttgagtgcta tgctgagagg actgcaaaag  1680
```

```
gcaatgttct ggaaccgcaa gggttaattg agatcaagtt caggtcagag gaactccagg    1740
attgcatgag tcggcttgac ccaacattaa ttgatctgaa agcaaaactc gaagtagcaa    1800
ataaaaatgg aagtgctgac acaaaatcgc ttcaagaaaa tatagaagct cgaacaaaac    1860
agttgatgcc tctatatact cagattgcga tacggtttgc tgaattgcat gatacatccc    1920
tcagaatggc tgcgaaaggt gtgattaaga agttgtggga ctgggaagaa tcacgatctt    1980
tcttctataa gagattacgg aggaggatct ctgaggatgt tcttgcaaaa gaaattagag    2040
ctgtagcagg tgagcagttt tcccaccaac cagcaatcga gctgatcaag aaatggtatt    2100
cagcttcaca tgcagctgaa tgggatgatg acgatgcttt tgttgcttgg atggataacc    2160
ctgaaaacta caaggattat attcaatatc ttaaggctca aagagtatcc caatccctct    2220
caagtctttc agattccagc tcagatttgc aagccctgcc acagggtctt tccatgttac    2280
tagataaggt aattagctta ctgatgctta tataaattct tttcattac atatggctgg     2340 agaactatct aatcaaataa tgattataat tccaatcgtt ctttttatgc cattatgatc    2400
ttctgaaatt tccttctttg gacacttatt cagatggatc cctctagaag agctcaactt    2460
gttgaagaaa tcaggaaggt ccttggttga atcatatgat g                       2501

<210> SEQ ID NO 2
<211> LENGTH: 2501
<212> TYPE: DNA
<213> ORGANISM: Oryza sativa

<400> SEQUENCE: 2
cctgttctgc taggaataat agaactacat actgctatga ttttccactg gtgagttgac     60
tgctccctta tattcaatgc attaccatag caaattcata ttcgttcatg ttgtcaaaat    120
aagccgatga aaattcaaaa ctgtaggcat ttgaaactgc agtgaggaag tcatggtcct    180
ctagtacctc tggtgcttct aaaggtgttg aaaatgccca atgttatgtt aaagctacag    240
agttggtatt tgcggacaaa catgggtcat ggggcactcc tttagttcaa atggaccggc    300
ctgctgggct caatgacatt ggtatggtag cttggacctt gaagatgtcc actcctgaat    360
ttcctagtgg tagggagatt attgttgttg caaatgatat tacgttcaga gctggatcat    420
ttggcccaag ggaagatgca ttttttgaag ctgttaccaa cctagcctgt gagaagaaac    480
ttcctcttat ttatttggca gcaaattctg gtgctcgaat tggcatagca gatgaagtga    540
atcttgcttc cgtgttgggt ggtctgatga tggcagccc tgaacgtggg tttcagtaca    600
tttatctaag cgaagaagac tatgctcgta ttggcacttc tgtcatagca cataagatgc    660
agctagacag tggtgaaatt aggtgggtta ttgattctgt tgtgggcaag gaagatggac    720
ttggtgtgga gaatatacat ggaagtgctg ctattgccag tgcttattct agggcatata    780
aggagacatt tacacttaca tttgtgactg gaagaactgt tggaataggt gcttatcttg    840
ctcgacttgg catccggtgc atacagcgtc ttgaccagcc tattattctt acaggctatt    900
ctgcactgaa caagcttctt gggcgggaag tgtacagctc ccacatgcag ttgggtggtc    960
ccaaaatcat ggcaactaat ggtgttgtcc atcttactgt ttcagatgac cttgaaggcg   1020
tttctaatat attgaggtgg ctcagttatg ttcctgccta cattggtgga ccacttccag   1080
taacaacacc gttggaccca ccggacagac tgttgcata cattcctgag aactcgtgtg   1140
atcctcgagc ggctatccgt ggtgttgatg acagccaagg gaaatggtta ggtggtatgt   1200
ttgataagaa cagctttgtg gaaacatttg aaggttgggc taagacagtg ttactggca    1260 gagcaaagct tggtggaatt ccagtgggtg tgatagctgt ggagactcag accatgatgc   1320
```

```
aaactatccc tgctgacect ggtcagcttg attccegtga gcaatctgtt cctcgtgctg    1380
gacaagtgtg gtttccagat tctgcaacca agactgcgca ggcattgctg gacttcaacc    1440
gtgaaggatt acctctgttc atcctcgcta actggagagg cttctctggt ggacaaagag    1500
atcttttga  aggaattctt caggctggct cgactattgt tgagaacctt aggacataca    1560
atcagcctgc ctttgtctac attcccatgg ctgcagagct acgaggaggg gcttgggttg    1620
tggttgatag caagataaac ccagaccgca ttgagtgcta tgctgagagg actgcaaaag    1680
gcaatgttct ggaaccgcaa gggttaattg agatcaagtt caggtcagag gaactccagg    1740
attgcatgag tcggcttgac ccaacattaa ttgatctgaa agcaaaactc gaagtagcaa    1800
ataaaaatgg aagtgctgac acaaaatcgc ttcaagaaaa tatagaagct cgaacaaaac    1860
agttgatgcc tctatatact cagattgcga tacggtttgc tgaattgcat gatacatccc    1920
tcagaatggc tgcgaaaggt gtgattaaga agttgtggga ctgggaagaa tcacgatctt    1980
tcttctataa gagattacgg aggaggatct ctgaggatgt tcttgcaaaa gaaattagag    2040
ctgtagcagg tgagcagttt tcccaccaac cagcaatcga gctgatcaag aaatggtatt    2100
cagcttcaca tgcagctgaa tgggatgatg acgatgcttt tgttgcttgg atggataacc    2160
ctgaaaacta caaggattat attcaatatc ttaaggctca aagagtatcc caatccctct    2220
caagtctttc agattccagc tcagatttgc aagccctgcc acagggtctt tccatgttac    2280
tagataaggt aattagctta ctgatgctta tataaattct tttcattac  atatggctgg    2340
agaactatct aatcaaataa tgattataat tccaatcgtt cttttatgc  cattatgatc    2400
ttctgaaatt tccttctttg gacacttatt cagatggatc cctctagaag agctcaactt    2460
gttgaagaaa tcaggaaggt ccttggttga atcatatgat g                        2501

<210> SEQ ID NO 3
<211> LENGTH: 2501
<212> TYPE: DNA
<213> ORGANISM: Oryza sativa

<400> SEQUENCE: 3
cctgttctgc taggaataat agaactacat actgctatga ttttccactg gtgagttgac      60
tgctccctta tattcaatgc attaccatag caaattcata ttcgttcatg ttgtcaaaat     120
aagccgatga aaattcaaaa ctgtaggcat ttgaaactgc agtgaggaag tcatggtcct     180
ctagtacctc tggtgcttct aaaggtgttg aaaatgccca atgttatgtt aaagctacag     240
agttggtatt tgcggacaaa catgggtcat ggggcactcc tttagttcaa atggaccggc     300
ctgctgggct caatgacatt ggtatggtag cttggacctt gaagatgtcc actcctgaat     360
ttcctagtgg tagggagatt attgttgttg caaatgatat tacgttcaga gctggatcat     420
ttggcccaag ggaagatgca tttttgaag  ctgttaccaa cctagcctgt gagaagaaac     480
ttcctcttat ttatttggca gcaaattctg tgctcgaat  tggcatagca gatgaagtga     540
aatcttgctt ccgtgttggg tggtctgatg atggcagccc tgaacgtggg tttcagtaca     600
tttatctaag cgaagaagac tatgctcgta ttggcacttc tgtcatagca cataagatgc     660
agctagacag tggtgaaatt aggtgggtta ttgattctgt tgtgggcaag gaagatggac     720
ttggtgtgga gaatatacat ggaagtgctg ctattgccag tgcttattct agggcatata     780
aggagacatt tacacttaca tttgtgactg gaagaactgt tggaatagga gcttatcttg     840
ctcgacttgg catccggtgc atacagcgtc ttgaccagcc tattattctt acaggctatt     900
ctgcactgaa caagcttctt gggcgggaag tgtacagctc ccacatgcag ttgggtggtc     960
```

-continued

| | |
|---|---|
| ccaaaatcat ggcaactaat ggtgttgtcc atcttactgt ttcagatgac cttgaaggcg | 1020 |
| tttctaatat attgaggtgg ctcagttatg ttcctgccta cattggtgga ccacttccag | 1080 |
| taacaacacc gttggaccca ccggacagac ctgttgcata cattcctgag aactcgtgtg | 1140 |
| atcctcgagc ggctatccgt ggtgttgatg acagccaagg gaaatggtta ggtggtatgt | 1200 |
| tgataaaga cagctttgtg gaaacatttg aaggttgggc taagacagtg ttactggca | 1260 |
| gagcaaagct tggtggaatt ccagtgggtg tgatagctgt ggagactcag accatgatgc | 1320 |
| aaactatccc tgctgaccct ggtcagcttg attcccgtga gcaatctgtt cctcgtgctg | 1380 |
| gacaagtgtg gtttccagat tctgcaacca agactgcgca ggcattgctg gacttcaacc | 1440 |
| gtgaaggatt acctctgttc atcctcgcta actggagagg cttctctggt ggacaaagag | 1500 |
| atcttttga aggaattctt caggctggct cgactattgt tgagaaccct aggacataca | 1560 |
| atcagcctgc ctttgtctac attcccatgg ctgcagagct acgaggaggg gcttgggttg | 1620 |
| tggttgatag caagataaac ccagaccgca ttgagtgcta tgctgagagg actgcaaaaa | 1680 |
| gcaatgttct ggaaccgcaa gggttaattg agatcaagtt caggtcagag gaactccagg | 1740 |
| attgcatgag tcggcttgac ccaacattaa ttgatctgaa agcaaaactc gaagtagcaa | 1800 |
| ataaaaatgg aagtgctgac acaaaatcgc ttcaagaaaa tatagaagct cgaacaaaac | 1860 |
| agttgatgcc tctatatact cagattgcga tacggtttgc tgaattgcat gatacatccc | 1920 |
| tcagaatggc tgcgaaaggt gtgattaaga agttgtgga ctgggaagaa tcacgatctt | 1980 |
| tcttctataa agagattacgg aggaggatct ctgaggatgt tcttgcaaaa gaaattagag | 2040 |
| ctgtagcagg tgagcagttt tcccaccaac cagcaatcga gctgatcaag aaatggtatt | 2100 |
| cagcttcaca tgcagctgaa tgggatgatg acgatgcttt tgttgcttgg atggataacc | 2160 |
| ctgaaaacta caaggattat attcaatatc ttaaggctca aagagtatcc caatccctct | 2220 |
| caagtctttc agattccagc tcagatttgc aagccctgcc acagggtctt tccatgttac | 2280 |
| tagataaggt aattagctta ctgatgctta tataaattct tttcattac atatggctgg | 2340 |
| agaactatct aatcaaataa tgattataat tccaatcgtt ctttttatgc cattatgatc | 2400 |
| ttctgaaatt tccttctttg gacacttatt cagatggatc cctctagaag agctcaactt | 2460 |
| gttgaagaaa tcaggaaggt ccttggttga atcatatgat g | 2501 |

<210> SEQ ID NO 4
<211> LENGTH: 674
<212> TYPE: PRT
<213> ORGANISM: Oryza sativa

<400> SEQUENCE: 4

Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
    50                  55                  60

Pro Leu Ile Tyr Leu Ala Ala Asn Ser Gly Ala Arg Ile Gly Ile Ala
65                  70                  75                  80

Asp Glu Val Lys Ser Cys Phe Arg Val Gly Trp Ser Asp Asp Gly Ser
                85                  90                  95

```
Pro Glu Arg Gly Phe Gln Tyr Ile Tyr Leu Ser Glu Glu Asp Tyr Ala
                100                 105                 110

Arg Ile Gly Thr Ser Val Ile Ala His Lys Met Gln Leu Asp Ser Gly
            115                 120                 125

Glu Ile Arg Trp Val Ile Asp Ser Val Val Gly Lys Glu Asp Gly Leu
        130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
            180                 185                 190

Arg Leu Asp Gln Pro Ile Ile Leu Thr Gly Tyr Ser Ala Leu Asn Lys
        195                 200                 205

Leu Leu Gly Arg Glu Val Tyr Ser Ser His Met Gln Leu Gly Gly Pro
210                 215                 220

Lys Ile Met Ala Thr Asn Gly Val Val His Leu Thr Val Ser Asp Asp
225                 230                 235                 240

Leu Glu Gly Val Ser Asn Ile Leu Arg Trp Leu Ser Tyr Val Pro Ala
                245                 250                 255

Tyr Ile Gly Gly Pro Leu Pro Val Thr Thr Pro Leu Asp Pro Pro Asp
            260                 265                 270

Arg Pro Val Ala Tyr Ile Pro Glu Asn Ser Cys Asp Pro Arg Ala Ala
        275                 280                 285

Ile Arg Gly Val Asp Asp Ser Gln Gly Lys Trp Leu Gly Gly Met Phe
290                 295                 300

Asp Lys Asp Ser Phe Val Glu Thr Phe Glu Gly Trp Ala Lys Thr Val
305                 310                 315                 320

Val Thr Gly Arg Ala Lys Leu Gly Gly Ile Pro Val Gly Val Ile Ala
                325                 330                 335

Val Glu Thr Gln Thr Met Met Gln Thr Ile Pro Ala Asp Pro Gly Gln
            340                 345                 350

Leu Asp Ser Arg Glu Gln Ser Val Pro Arg Ala Gly Gln Val Trp Phe
        355                 360                 365

Pro Asp Ser Ala Thr Lys Thr Ala Gln Ala Leu Leu Asp Phe Asn Arg
370                 375                 380

Glu Gly Leu Pro Leu Phe Ile Leu Ala Asn Trp Arg Gly Phe Ser Gly
385                 390                 395                 400

Gly Gln Arg Asp Leu Phe Glu Gly Ile Leu Gln Ala Gly Ser Thr Ile
                405                 410                 415

Val Glu Asn Leu Arg Thr Tyr Asn Gln Pro Ala Phe Val Tyr Ile Pro
            420                 425                 430

Met Ala Ala Glu Leu Arg Gly Gly Ala Trp Val Val Asp Ser Lys
        435                 440                 445

Ile Asn Pro Asp Arg Ile Glu Cys Tyr Ala Glu Arg Thr Ala Lys Gly
450                 455                 460

Asn Val Leu Glu Pro Gln Gly Leu Ile Glu Ile Lys Phe Arg Ser Glu
465                 470                 475                 480

Glu Leu Gln Asp Cys Met Ser Arg Leu Asp Pro Thr Leu Ile Asp Leu
                485                 490                 495

Lys Ala Lys Leu Glu Val Ala Asn Lys Asn Gly Ser Ala Asp Thr Lys
            500                 505                 510
```

```
Ser Leu Gln Glu Asn Ile Glu Ala Arg Thr Lys Gln Leu Met Pro Leu
        515                 520                 525

Tyr Thr Gln Ile Ala Ile Arg Phe Ala Glu Leu His Asp Thr Ser Leu
    530                 535                 540

Arg Met Ala Ala Lys Gly Val Ile Lys Val Val Asp Trp Glu Glu
545                 550                 555                 560

Ser Arg Ser Phe Phe Tyr Lys Arg Leu Arg Arg Ile Ser Glu Asp
                565                 570                 575

Val Leu Ala Lys Glu Ile Arg Ala Val Ala Gly Glu Gln Phe Ser His
            580                 585                 590

Gln Pro Ala Ile Glu Leu Ile Lys Lys Trp Tyr Ser Ala Ser His Ala
        595                 600                 605

Ala Glu Trp Asp Asp Asp Ala Phe Val Ala Trp Met Asp Asn Pro
610                 615                 620

Glu Asn Tyr Lys Asp Tyr Ile Gln Tyr Leu Lys Ala Gln Arg Val Ser
625                 630                 635                 640

Gln Ser Leu Ser Ser Leu Ser Asp Ser Ser Asp Leu Gln Ala Leu
                645                 650                 655

Pro Gln Gly Leu Ser Met Leu Leu Asp Lys Val Ile Ser Leu Leu Met
            660                 665                 670

Leu Ile

<210> SEQ ID NO 5
<211> LENGTH: 674
<212> TYPE: PRT
<213> ORGANISM: Oryza sativa

<400> SEQUENCE: 5

Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
    50                  55                  60

Pro Leu Ile Tyr Leu Ala Ala Asn Ser Gly Ala Arg Ile Gly Ile Ala
65              70                  75                  80

Asp Glu Val Lys Ser Cys Phe Arg Val Gly Trp Ser Asp Asp Gly Ser
                85                  90                  95

Pro Glu Arg Gly Phe Gln Tyr Ile Tyr Leu Ser Glu Glu Asp Tyr Ala
            100                 105                 110

Arg Ile Gly Thr Ser Val Ile Ala His Lys Met Gln Leu Asp Ser Gly
        115                 120                 125

Glu Ile Arg Trp Val Ile Asp Ser Val Val Gly Lys Glu Asp Gly Leu
    130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
            180                 185                 190

Arg Leu Asp Gln Pro Ile Ile Leu Thr Gly Tyr Ser Ala Leu Asn Lys
        195                 200                 205
```

-continued

```
Leu Leu Gly Arg Glu Val Tyr Ser Ser His Met Gln Leu Gly Gly Pro
210                 215                 220
Lys Ile Met Ala Thr Asn Gly Val Val His Leu Thr Val Ser Asp Asp
225                 230                 235                 240
Leu Glu Gly Val Ser Asn Ile Leu Arg Trp Leu Ser Tyr Val Pro Ala
                    245                 250                 255
Tyr Ile Gly Gly Pro Leu Pro Val Thr Thr Pro Leu Asp Pro Pro Asp
                260                 265                 270
Arg Pro Val Ala Tyr Ile Pro Glu Asn Ser Cys Asp Pro Arg Ala Ala
                275                 280                 285
Ile Arg Gly Val Asp Asp Ser Gln Gly Lys Trp Leu Gly Gly Met Phe
290                 295                 300
Asp Lys Asp Ser Phe Val Glu Thr Phe Glu Gly Trp Ala Lys Thr Val
305                 310                 315                 320
Val Thr Gly Arg Ala Lys Leu Gly Gly Ile Pro Val Gly Val Ile Ala
                325                 330                 335
Val Glu Thr Gln Thr Met Met Gln Thr Ile Pro Ala Asp Pro Gly Gln
                340                 345                 350
Leu Asp Ser Arg Glu Gln Ser Val Pro Arg Ala Gly Gln Val Trp Phe
                355                 360                 365
Pro Asp Ser Ala Thr Lys Thr Ala Gln Ala Leu Leu Asp Phe Asn Arg
370                 375                 380
Glu Gly Leu Pro Leu Phe Ile Leu Ala Asn Trp Arg Gly Phe Ser Gly
385                 390                 395                 400
Gly Gln Arg Asp Leu Phe Glu Gly Ile Leu Gln Ala Gly Ser Thr Ile
                405                 410                 415
Val Glu Asn Leu Arg Thr Tyr Asn Gln Pro Ala Phe Val Tyr Ile Pro
                420                 425                 430
Met Ala Ala Glu Leu Arg Gly Gly Ala Trp Val Val Asp Ser Lys
                435                 440                 445
Ile Asn Pro Asp Arg Ile Glu Cys Tyr Ala Glu Arg Thr Ala Lys Gly
450                 455                 460
Asn Val Leu Glu Pro Gln Gly Leu Ile Glu Ile Lys Phe Arg Ser Glu
465                 470                 475                 480
Glu Leu Gln Asp Cys Met Ser Arg Leu Asp Pro Thr Leu Ile Asp Leu
                485                 490                 495
Lys Ala Lys Leu Glu Val Ala Asn Lys Asn Gly Ser Ala Asp Thr Lys
                500                 505                 510
Ser Leu Gln Glu Asn Ile Glu Ala Arg Thr Lys Gln Leu Met Pro Leu
                515                 520                 525
Tyr Thr Gln Ile Ala Ile Arg Phe Ala Glu Leu His Asp Thr Ser Leu
530                 535                 540
Arg Met Ala Ala Lys Gly Val Ile Lys Lys Val Val Asp Trp Glu Glu
545                 550                 555                 560
Ser Arg Ser Phe Phe Tyr Lys Arg Leu Arg Arg Ile Ser Glu Asp
                565                 570                 575
Val Leu Ala Lys Glu Ile Arg Ala Val Ala Gly Glu Gln Phe Ser His
                580                 585                 590
Gln Pro Ala Ile Glu Leu Ile Lys Lys Trp Tyr Ser Ala Ser His Ala
                595                 600                 605
Ala Glu Trp Asp Asp Asp Ala Phe Val Ala Trp Met Asp Asn Pro
610                 615                 620
```

```
Glu Asn Tyr Lys Asp Tyr Ile Gln Tyr Leu Lys Ala Gln Arg Val Ser
625                 630                 635                 640

Gln Ser Leu Ser Ser Leu Ser Asp Ser Ser Asp Leu Gln Ala Leu
        645                 650                 655

Pro Gln Gly Leu Ser Met Leu Leu Asp Lys Val Ile Ser Leu Leu Met
            660                 665                 670

Leu Ile

<210> SEQ ID NO 6
<211> LENGTH: 674
<212> TYPE: PRT
<213> ORGANISM: Oryza sativa

<400> SEQUENCE: 6

Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
                20                  25                  30

Val Ala Asn Asp Ile Thr Phe Arg Ala Gly Ser Phe Gly Pro Arg Glu
            35                  40                  45

Asp Ala Phe Phe Glu Ala Val Thr Asn Leu Ala Cys Glu Lys Lys Leu
        50                  55                  60

Pro Leu Ile Tyr Leu Ala Ala Asn Ser Gly Ala Arg Ile Gly Ile Ala
65                  70                  75                  80

Asp Glu Val Lys Ser Cys Phe Arg Val Gly Trp Ser Asp Asp Gly Ser
                85                  90                  95

Pro Glu Arg Gly Phe Gln Tyr Ile Tyr Leu Ser Glu Glu Asp Tyr Ala
            100                 105                 110

Arg Ile Gly Thr Ser Val Ile Ala His Lys Met Gln Leu Asp Ser Gly
        115                 120                 125

Glu Ile Arg Trp Val Ile Asp Ser Val Val Gly Lys Glu Asp Gly Leu
    130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
            180                 185                 190

Arg Leu Asp Gln Pro Ile Ile Leu Thr Gly Tyr Ser Ala Leu Asn Lys
        195                 200                 205

Leu Leu Gly Arg Glu Val Tyr Ser Ser His Met Gln Leu Gly Gly Pro
    210                 215                 220

Lys Ile Met Ala Thr Asn Gly Val Val His Leu Thr Val Ser Asp Asp
225                 230                 235                 240

Leu Glu Gly Val Ser Asn Ile Leu Arg Trp Leu Ser Tyr Val Pro Ala
                245                 250                 255

Tyr Ile Gly Gly Pro Leu Pro Val Thr Thr Pro Leu Asp Pro Pro Asp
            260                 265                 270

Arg Pro Val Ala Tyr Ile Pro Glu Asn Ser Cys Asp Pro Arg Ala Ala
        275                 280                 285

Ile Arg Gly Val Asp Asp Ser Gln Gly Lys Trp Leu Gly Gly Met Phe
    290                 295                 300

Asp Lys Asp Ser Phe Val Glu Thr Phe Glu Gly Trp Ala Lys Thr Val
305                 310                 315                 320
```

```
Val Thr Gly Arg Ala Lys Leu Gly Gly Ile Pro Val Gly Val Ile Ala
            325                 330                 335

Val Glu Thr Gln Thr Met Met Gln Thr Ile Pro Ala Asp Pro Gly Gln
        340                 345                 350

Leu Asp Ser Arg Glu Gln Ser Val Pro Arg Ala Gly Gln Val Trp Phe
            355                 360                 365

Pro Asp Ser Ala Thr Lys Thr Ala Gln Ala Leu Leu Asp Phe Asn Arg
        370                 375                 380

Glu Gly Leu Pro Leu Phe Ile Leu Ala Asn Trp Arg Gly Phe Ser Gly
385                 390                 395                 400

Gly Gln Arg Asp Leu Phe Glu Gly Ile Leu Gln Ala Gly Ser Thr Ile
            405                 410                 415

Val Glu Asn Leu Arg Thr Tyr Asn Gln Pro Ala Phe Val Tyr Ile Pro
        420                 425                 430

Met Ala Ala Glu Leu Arg Gly Gly Ala Trp Val Val Asp Ser Lys
            435                 440                 445

Ile Asn Pro Asp Arg Ile Glu Cys Tyr Ala Glu Arg Thr Ala Lys Ser
        450                 455                 460

Asn Val Leu Glu Pro Gln Gly Leu Ile Glu Ile Lys Phe Arg Ser Glu
465                 470                 475                 480

Glu Leu Gln Asp Cys Met Ser Arg Leu Asp Pro Thr Leu Ile Asp Leu
            485                 490                 495

Lys Ala Lys Leu Glu Val Ala Asn Lys Asn Gly Ser Ala Asp Thr Lys
        500                 505                 510

Ser Leu Gln Glu Asn Ile Glu Ala Arg Thr Lys Gln Leu Met Pro Leu
            515                 520                 525

Tyr Thr Gln Ile Ala Ile Arg Phe Ala Glu Leu His Asp Thr Ser Leu
        530                 535                 540

Arg Met Ala Ala Lys Gly Val Ile Lys Lys Val Val Asp Trp Glu Glu
545                 550                 555                 560

Ser Arg Ser Phe Phe Tyr Lys Arg Leu Arg Arg Ile Ser Glu Asp
            565                 570                 575

Val Leu Ala Lys Glu Ile Arg Ala Val Ala Gly Glu Gln Phe Ser His
        580                 585                 590

Gln Pro Ala Ile Glu Leu Ile Lys Lys Trp Tyr Ser Ala Ser His Ala
            595                 600                 605

Ala Glu Trp Asp Asp Asp Ala Phe Val Ala Trp Met Asp Asn Pro
        610                 615                 620

Glu Asn Tyr Lys Asp Tyr Ile Gln Tyr Leu Lys Ala Gln Arg Val Ser
625                 630                 635                 640

Gln Ser Leu Ser Ser Leu Ser Asp Ser Ser Asp Leu Gln Ala Leu
            645                 650                 655

Pro Gln Gly Leu Ser Met Leu Leu Asp Lys Val Ile Ser Leu Leu Met
        660                 665                 670

Leu Ile

<210> SEQ ID NO 7
<211> LENGTH: 201
<212> TYPE: DNA
<213> ORGANISM: Oryza sativa

<400> SEQUENCE: 7
ataaagatga ggtgtttgat gaattaaagg ccgcagggtt gaagaggcca tgtagcttta      60
cagatatttc cagtgaaaat gctttgcttc ttgaatttga kacagcaact gatgcagctg     120
```

```
ctgcgaaagc ccatattagg cgccagcttc atccagatgt ctgttcccag acaagaata      180 cttctggtca tgaactttt g                                                 201

<210> SEQ ID NO 8
<211> LENGTH: 201
<212> TYPE: DNA
<213> ORGANISM: Oryza sativa

<400> SEQUENCE: 8
tcacatgatc tgcaactgtc aacagtctta ccggaattgg attctgaagg tggatactcc      60
acctgtccac cataagtcct tatttgtcag aggttacaat ygcatgatgt gtctatactc     120
tatactgcaa agatgaatac taacaagttt ttcttgggct aaaagaaga aaaactagga      180 acagcctcac tagtttgcta g                                                201

<210> SEQ ID NO 9
<211> LENGTH: 201
<212> TYPE: DNA
<213> ORGANISM: Oryza sativa

<400> SEQUENCE: 9
tgtttcaagt ttggttgctg aaaaacgtac ggacaaacca tgaactaact tgctattttg      60
ctccacatgg gtttgtctcg aagcaaccag gaattgatca rcttcggtgg tttgccaaga     120
acatgaaacc tggggataag gattttttc gactttgcta atgctggtcg tctggattag     180
gaacagaaca ggtattgcta c                                                201

<210> SEQ ID NO 10
<211> LENGTH: 201
<212> TYPE: DNA
<213> ORGANISM: Oryza sativa

<400> SEQUENCE: 10
agtctaaatg ggctgcactt tgattgggct gggttcatat gagattaggg gaaaaaacac      60
gaacattcca gtaaatggg gagtgtgaac tgtgaagaag rgggtaaacg gtgtgcggac     120
gtgagacgag aaaagcatga gagaaaacga tctgtgtgca tgcatagggc tggacgaaaa     180
gctcgtgact cgttagctcg c                                                201

<210> SEQ ID NO 11
<211> LENGTH: 201
<212> TYPE: DNA
<213> ORGANISM: Oryza sativa

<400> SEQUENCE: 11
tagggcttct gatagccctc catctgtccg tcctttgccc gtttgcttct tggcctaaac      60
caccgaaaag gtgggtccgt tttgctggac gcctggaata ytcttcaact cgattggaac     120
agcaggctcc gtgtatgtgt aactatggct gtgtttagat ctaaagttta gattcaaagt     180
atagatttaa acttcagtca t                                                201

<210> SEQ ID NO 12
<211> LENGTH: 201
<212> TYPE: DNA
<213> ORGANISM: Oryza sativa

<400> SEQUENCE: 12
tgctgattct caggctgatt ctacttggtt ggtagaaaat ctacttatcc aggaacaagc      60
gtagggtaac ttttcctttt tttctcagct atgtgaaaag rgagaaaact cgctacactt     120
```

```
tataggaaat gaactactct tctaccgacg gatatcctaa aggctatcct ctggtacctc    180
ggccttacgc taactcaaaa c                                              201

<210> SEQ ID NO 13
<211> LENGTH: 201
<212> TYPE: DNA
<213> ORGANISM: Oryza sativa

<400> SEQUENCE: 13
cgatcccagg gaggttgtgg aagtgcttct catgaccttc gaggcactgc ggcgtaggca     60
tcttcaattg gatgagacac aagagactag caaacgtgca racctgaagg ctggtgccat    120
catgttggcc agtaatctga gggctaacat tgggaagagg attggagctg tccctggagt    180
tgaagtaggg gatattttct a                                              201

<210> SEQ ID NO 14
<211> LENGTH: 201
<212> TYPE: DNA
<213> ORGANISM: Oryza sativa

<400> SEQUENCE: 14
aattccaatt tcatcccatt tgtcccattc cctcctgatt actttgccaa gaaaaataag     60
cctgtggaga attcatcaga tgcaggaata gtgccagaag rccctccatc agctgaaaaa    120
ttaccagaaa caaaatattc atctggaaat ctgggaaatt ttcagaacag ctcacaggtg    180
atgggcagtc aggcagcaaa c                                              201

<210> SEQ ID NO 15
<211> LENGTH: 201
<212> TYPE: DNA
<213> ORGANISM: Oryza sativa

<400> SEQUENCE: 15
gttttggttg ctattaatcg attgagcaag taggggaaat attcctatca tctatgcttc     60
aaataaagtt ttctcttaaa ttactcatcc gatttacaat ycgattacac cgttgtgttc    120
gtaataatta aatctttaca acaagatctc acatgattat attttgatga aaaatcacaa    180
attactttta tgatatgtct a                                              201

<210> SEQ ID NO 16
<211> LENGTH: 201
<212> TYPE: DNA
<213> ORGANISM: Oryza sativa

<400> SEQUENCE: 16
gtcccgcctg gtgacgattt ccatgggcat tgcgccgact gactgtgtcg gcagcatgca     60
tcgtctcggg cgttcaacgt gtggagggga cgacgtataa ragtacacgc gaagactgta    120
ggtagaggtg cttttcccgc gaaaagtggc agtagcggcg gttggacagt aaccttcgtg    180
tatggttgtg tgttcatctc a                                              201

<210> SEQ ID NO 17
<211> LENGTH: 201
<212> TYPE: DNA
<213> ORGANISM: Oryza sativa

<400> SEQUENCE: 17
tgcttgtgcg ttcactgttc agagaagctg gttatcctcc ctgataagaa cagccgggag     60
gtcagtgtgc tatggttttg tttagttctg gaatgatcca rtcacccagc acaattgact    120
```

```
ggctgagtgt tgcattaagc aaatctggac cggatttgag ggaatttct cgcgcagtgg    180 agatctatga taaatctcgt a                                             201

<210> SEQ ID NO 18
<211> LENGTH: 201
<212> TYPE: DNA
<213> ORGANISM: Oryza sativa

<400> SEQUENCE: 18
ctgcttcgcc aacggcctcg aggcgaggct ggcaggtact ggtagtcaaa tttacaagaa    60
ctacacgata actcggcttc catgcactga tgtgctgaaa rcgtaccagc tttatttggc   120
agcttgccca tttaagaaga tctctcatta ctttgccaat caaacaattt tgaatgctgt   180
ggagaaggcc aagaaagttc a                                             201

<210> SEQ ID NO 19
<211> LENGTH: 201
<212> TYPE: DNA
<213> ORGANISM: Oryza sativa

<400> SEQUENCE: 19
tcacattctg gttgttgagg gtccactgat accttacct gttgcagttt attgttttaa    60
ataatccaat caaacttttg tttgagctta ttgctgaata rcacagcagc agtacatgca   120
atgcaagatg cccagatgat gagaataaag gcaatggcaa aaatataagt gctagttcta   180
tttcaaaata acaaacagac a                                             201

<210> SEQ ID NO 20
<211> LENGTH: 201
<212> TYPE: DNA
<213> ORGANISM: Oryza sativa

<400> SEQUENCE: 20
tatgatgatg cttattatag cctaaggtat gtacttttaa gatttagttc gaagtaatgc    60
ccatctggca agttaattcc agcattaacg tgttctaaaa rccactctac ttatgagaag   120
ccgggccacc acattcatac attacagcca gaaacaacaa atccaggaag ttaatacgtg   180
attaagaatg catcaaacaa g                                             201

<210> SEQ ID NO 21
<211> LENGTH: 201
<212> TYPE: DNA
<213> ORGANISM: Oryza sativa

<400> SEQUENCE: 21
tcgatatgtt gggttttttc tctttactag tagcatgcca tctagtgtgc atcttacgta    60
gtggaatatt atcgggcacc caatattcgg ctcgcacaaa rctccgagga cgaggaggag   120
gacgactaat ttggcagctc agctcacctg cacggctgca ctgtgctgtg cccggtgggc   180
gaagccattt cacccgcggg c                                             201

<210> SEQ ID NO 22
<211> LENGTH: 201
<212> TYPE: DNA
<213> ORGANISM: Oryza sativa

<400> SEQUENCE: 22
tctgaaaacg catggccgaa ataagatgca agaacacctg caaataatc tcaggatcag    60 tccaggtacg cattctctac tgttatctac tgaaccagag rggaaaaaaa caaaaactag   120
```

```
gatgaatgca gtgtcacttt gctgcttgta attctctgaa tttctgaatg aaagaaaaga      180
aaagaaaaga agcgaaactg g                                                201

<210> SEQ ID NO 23
<211> LENGTH: 201
<212> TYPE: DNA
<213> ORGANISM: Oryza sativa

<400> SEQUENCE: 23
cttaaattct catgttttat tcccgttgca acgaacggtc atttctttta gtgtccataa       60
atagctataa gaggcatcga tcatcgcagc aagccgactg rgtgtggcgc ctacgtgatc      120
gttggtttgt ttcgcttgtt tgggcataca gctatgagaa ctttgttggg ggcccatact      180
acttatcatc atgtgtctaa t                                                201

<210> SEQ ID NO 24
<211> LENGTH: 201
<212> TYPE: DNA
<213> ORGANISM: Oryza sativa

<400> SEQUENCE: 24
gaactaaaca cacccggaat gtgatggatc cgaatctgct gtagttgata ctgtgaatgt       60
aacttgtagg cctcatttga ttttctagaa aaaatggag raaaaacata ggaataagaa      120
tcctatgtga attggtactg ttcatcccctt tgatttgtag gaattgaaca aaggaaaagc     180
atggggaaaa aaatcctatg a                                                201

<210> SEQ ID NO 25
<211> LENGTH: 201
<212> TYPE: DNA
<213> ORGANISM: Oryza sativa

<400> SEQUENCE: 25
agcgccacgc cgcggccagc gccgtggtgt tctccgggtg gcatcgcttg agctacatca       60
ccaccgatgg ccacttaaag tccgttgagc tcgatcgcca ratccggcgg ctccacaggg      120
ccgtcggcaa cgcggtcgtc gacgacaagt acttggtctt cgggaccggc tccacccacc      180
tgatcaacgc gctggtgtac g                                                201

<210> SEQ ID NO 26
<211> LENGTH: 201
<212> TYPE: DNA
<213> ORGANISM: Oryza sativa

<400> SEQUENCE: 26
acgggcggta ccagctacct gtcacagaca tgtgggccca gcttaacgct aacgcgctga       60
tggccccaca tggcagcgac ctgccccctc tgtccctccg ytccacgggc gcaccgagcg      120
tccaccgccc ccgcgatat ccgggggttt aggcgatatt tagccacgag aggggaggg       180 gagagtagga gaccgacgct t                                                201

<210> SEQ ID NO 27
<211> LENGTH: 201
<212> TYPE: DNA
<213> ORGANISM: Oryza sativa

<400> SEQUENCE: 27
agaaagactt gctttagctt tattgtttct tttccatatt ctatattctt gaaaaggact       60
gcaaagctct tctagtatat gcaattagct gctttggaag rcacttcaaa agggatgaag     120
```

```
gaaagaaggc tgtcatatca attactcaat catgaccaga tcatcgatct gatgcagtta    180
aaaatttcat taattttgcc a                                              201
```

<210> SEQ ID NO 28
<211> LENGTH: 401
<212> TYPE: DNA
<213> ORGANISM: Oryza sativa

<400> SEQUENCE: 28

```
atcgatgtaa ttagtgatgt caatcaatgg tccagatggc atttggagtc ttcgagcctt     60
atctttagtg tcacttgcat tttcagttcc aaatgaacat ctggaagaag gcttggatat    120
ctttggaatt tcattgatag gatgaaaatc tcttgccgca tgaagcctga cggagtttcc    180
gttagccaaa gtggcatcag rtacagcata ttccaaggaa tctgtgtgct tcctatcagg    240
ttttgctgga atggaaaatt gtgctggctc agttttgctg ttccccctac ttttcaataa    300
atcaggttca ccttcttttc gcagaccagt tgaattttgt atattctctt tacaagcaga    360
tgctgaagag tggcctaata aattatttgg tgaaacctct a                        401
```

<210> SEQ ID NO 29
<211> LENGTH: 401
<212> TYPE: DNA
<213> ORGANISM: Oryza sativa

<400> SEQUENCE: 29

```
taaccttata gtgggacaag gactgaaaag cagttcctct tgctttaacc cagagagggt     60
caacattttt ctccctgtaa gttccaatgc tccacaatat ttgtatcaag tgttttgagg    120
ttccaggata tgcttcagaa tccattgctc cccatctcaa tagaatgcat aagctgaaaa    180
ggcaagaaaa agtggaataa raaatagatt ttctacaagc acatgatcat tggtgggcac    240
tgcccacaga taaaactagc tagctctcgg cagtcttacc catgggaaac agtaggatct    300
atcgaaaaat caagcagctg ctttgatata actttccagg cagtatagaa atctggcaaa    360
gagattagca gctcacctca gaagtgaaat ttggagggca a                        401
```

<210> SEQ ID NO 30
<211> LENGTH: 398
<212> TYPE: DNA
<213> ORGANISM: Oryza sativa

<400> SEQUENCE: 30

```
ccaagcggag acatcgcttc catgagcaat tcacggtttt tcactagatc tctcacccett    60 tctctgatcc attctggacc agcctctaat gcgtagagcg ccaggcgctg cccgatgatg    120
gaagcacaga taggtatgtt atcttgcact ttgagcagct gtgcatgaag accgtcagct    180
tcgtttgggt gggcaatmtg cagcagtcag ctcatcagtt cttgtaagac tcactgatca    240
acacagattg tgcagccact aagttactta tactgcattg ctatggtgat aatttaaggg    300
aatgccctgg taaagattcc aagtggatgc gggaaattca tgaaactgaa agaactcaat    360
attgactctt acatcagcat tttcaagcct aagcagag                             398
```

<210> SEQ ID NO 31
<211> LENGTH: 401
<212> TYPE: DNA
<213> ORGANISM: Oryza sativa

<400> SEQUENCE: 31

```
tttaaatcaa atcttaaaaa tataaatcat aaataactat caagttgttg agtttaaaaa    60
tataaaaatt atataaatat atttgtcttg aaaaatactt tcataaaagt atacatatat   120
cacttttaa taaatatttt tataaaaaca agaagtcaaa gttatgtttt agagaccgcg    180
tctctgttct aaacgacttc ytttataagt atggagggag tatccatttc acatatactt   240
atggtcttgt ttacatccca acaaatttta gccaaaaaca tcacatcaaa tatttagcca   300
catgtatagg acattaaata taaaaaaaca attacacagt ttgcatgtaa attgcgagac   360
gaatcttttg agcctaatta cgccattatt tgacaatgtg g                      401
```

<210> SEQ ID NO 32
<211> LENGTH: 401
<212> TYPE: DNA
<213> ORGANISM: Oryza sativa

<400> SEQUENCE: 32

```
cggaactatg actaactcct ctccgtaagc ttctttgtaa tatgtattgc tgctgtactt    60
ggtctcatta tctccttaca gatatatata cattttttgc agggtatatc cacttcatct   120
tctccgtgac attgagacta gggtttggct cctggccgtg gagtcagaga gtcagtgtaa   180
agctgacgga gaatatgcac yttccagtgt tactcaaaat ctagctactg gaaacaatac   240
caatattata gaacaaacag ctgatgttat cacaaaaata gacaatagta tgagttcacc   300
acggatgaga ataacagaaa ggaatggtat aagggacaac accaccccat cattccatca   360
acatttgcaa ctctttgagt ctaatggcga aggcgtacat a                      401
```

<210> SEQ ID NO 33
<211> LENGTH: 375
<212> TYPE: DNA
<213> ORGANISM: Oryza sativa

<400> SEQUENCE: 33

```
caactactga caacaagtgc catgtctaaa tttctgaaca tgcacacaac acacaaatga    60
tgaatatggt gaaaccgcaa ttagcattag aaagttttaa ctctagaaat caatttccaa   120
gttgtaatcc ccatactccc aacccagaag ggaaaaaaaa caactccaaa acccycaact   180
tttaaaaatg tgggaacaat caaaccatat gcttgagata tacccacaaa gccatcggcg   240
gccgcttaca gcagagtaca ccctcatctt gcacgcctcc gaagaagcag gagccgtgat   300
caacacgagc atcttgtcct gctccacccc acacagtgac gagtctaggg cacgacgaag   360
gcgcgctcct aaacc                                                   375
```

<210> SEQ ID NO 34
<211> LENGTH: 401
<212> TYPE: DNA
<213> ORGANISM: Oryza sativa

<400> SEQUENCE: 34

```
cttcctgtcg tgagtgactg ggtggtgggc tcaatcggcc tggcccgata cgatgcaagc    60
gcgtggctgg gcaggagatc ggacggtgct gattgttggg gcgacgtggc cgcgtgggcg   120
aatgaatagt gaacagtacc gacgtgaggt ttataggatt ttatatgact aggggtgaac   180
gttggataga agggaatgtg ytagtgctgt tctgaacctc ttgcgcatac attaacatgt   240
tttatctaat ctaataaaca tgattaaatt tagcgtttgc ttttacagta gtagaaatat   300
```
gaaattgaac aatggttagt ctgaggaatc ataagcctat gatctagctg gagtcttctc    360
cggtttaagc taccaattga aacatattaa ttgatgcctg a    401

<210> SEQ ID NO 35
<211> LENGTH: 401
<212> TYPE: DNA
<213> ORGANISM: Oryza sativa

<400> SEQUENCE: 35
aatgtgctca acttcatata tatgtgtgtt gagcacatag ctcatatata agatcaatgg    60
ttagatcaat ggttttttggg ttagatcaat ggttgagcac atagctcata tatatgtgtg   120
ctcaacggct cacacacaac ttcatatata tgtacccaaa aaagcactat tagatcaatg    180
gttataattg tttcaccacg raatattcaa ctttactcaa tgttttgttt aacaagttcc    240
ttttggtcac ttgccaattt ttctagatca tacagtacaa tctattgatc acaattcaca    300
ttgaataact aggtcaagcc attctgtaca tgcccatgca tgaacttact gtactaatat    360
tatcttagat taatttatcc tgaaacttat agtcatatgt g    401

<210> SEQ ID NO 36
<211> LENGTH: 201
<212> TYPE: DNA
<213> ORGANISM: Oryza sativa
<220> FEATURE:
<221> NAME/KEY: misc_feature
<222> LOCATION: (102)..(102)
<223> OTHER INFORMATION: May or may not be present

<400> SEQUENCE: 36
gcatgaaagc tgagaccatc accaggttga tcgttgttgc tgctattata agatgccaaa    60
atcggcaaat cggtcattca ctcaaggatt ggacacaaga caaaaaaaaa gtaacaggta    120
gcagactttc aactaacctg gcatgaaagc ttggattgtc actggtttga ttgttgctgc    180
tgctgttatg aaagctgtat a    201

<210> SEQ ID NO 37
<211> LENGTH: 201
<212> TYPE: DNA
<213> ORGANISM: Oryza sativa

<400> SEQUENCE: 37
acgttgctta ggtagcacct tgatttaatc aaatgctagc tagttgatgc caggtggcac    60
actgcggacg gatttgtttg tcagtttccc tgcattacac wttgtacagg agtgtactac    120
atccacatac aatgaacagt agtagtagca gcagctatat actccagttg cctagtcgta    180
cacaaagtat aattaatcac a    201

<210> SEQ ID NO 38
<211> LENGTH: 401
<212> TYPE: DNA
<213> ORGANISM: Oryza sativa

<400> SEQUENCE: 38
gccggcgcag cgagaagagt gccgaatgtt ggatggagga cgccgaagcg cgggaaggtc    60
atggtggcgg cgttctggct ccgtccacgt cggactagcg acgcgtggtc gacgacccct    120
gtgctgcatc ctaccatgcc aactttgcgt atccgtcggc gtccatcttc gccaggatgc    180
cggggaagga gaagaagagg cggcggcgag gccgaagagg cgaggatagg gatgaggtgg    240
cggaggaggg gcgtgggagg ggaggcagcg agctcccgcc gccccgtcac tcctgccgct    300

```
ctcgtcgccc cgccattccg ccgagcttcc gccgccctgt cgttcccgcc gccccgccat    360
tccgccactc cgccgagctc ccgccgcccc gcctctcccg c                        401
```

<210> SEQ ID NO 39
<211> LENGTH: 401
<212> TYPE: DNA
<213> ORGANISM: Oryza sativa

<400> SEQUENCE: 39

```
acgcgcgcgc ctccattgtt ctcggatcaa caagctctcc aagaacagca gcaaagatga    60
agccttcgtc ttcctccgtc ggcgtctgta ccctgctggt ggcggtggcc tccctgcagc    120
tcctcctcgt cgtcgccgtc gccgcctcgg cgaagactgc accggcgatg ccagacgagg    180
agttcttggg ccgtctctgc gaccagcagc agggggccac gcggcggcgg ctcccgtggt    240
gccagcagct gcacgcgagg cggcgccacg gcggtggcgg cggcggcgtc ggcgtcggca    300
agcggcggcg ggtgccgatg ccgccgccca gccgcgccgg cgaggagatc gacgcgcgct    360
acgacgtgtc caagcgggtc gtgccgagcg gaccgaaccc g                        401
```

<210> SEQ ID NO 40
<211> LENGTH: 401
<212> TYPE: DNA
<213> ORGANISM: Oryza sativa

<400> SEQUENCE: 40

```
ttttggggtc ttcccttctt attttccctg agcgtagaaa attctgtggt ttccagtttt    60
ccacggaagt aaattccaat tttccaatag atgtacgtca acctttgct tcctctccag     120 ctgcagagtt gcaggtttga cgaatgcagc ttatctacaa aattcccatc agagggaaca    180
cagttacaga agaactaggg gaagtacaga ttgcaaatcc ataaggatct tctttagaac    240
cgtatacgta aagggcttca tggattggcc actatatatg ggtgtcaccc tcaatcgtga    300
atctgcaagg tcagatatca gtatatcaaa tgcagattgc ctcattgcag attgctgtgg    360
attgttcagg ttccgggtta gcccagtcac cagtcttcac t                        401
```

<210> SEQ ID NO 41
<211> LENGTH: 401
<212> TYPE: DNA
<213> ORGANISM: Oryza sativa

<400> SEQUENCE: 41

```
ccacgcgagc agctggtgtt tgctcatggt ggcagtggtg cgcgatacca gtagcgtgcg    60
cgacgcgtcg gggtggtcat cggcgagggc gagcatgtcg tcgtccagtg gacgcggact    120
ctagggtgat cacgctcggc cctgtcacgc tcaaaacaat actacggcac atctgattac    180
gttgacagga tctgagacca caccagaact atcccattcc gatcatgcat gtgaaaaaaa    240
aaacaaaggc caactattcc atttagcagt aatcaagatc cgatcttctc ttttcttgtg    300
aaaattcgac atgtttccgg ttaccaaccg aggaacacag attaattact ctagtttttt    360
cgaagagcag aagaggaata ttgattaccc ccacaaaacc c                        401
```

<210> SEQ ID NO 42
<211> LENGTH: 401
<212> TYPE: DNA
<213> ORGANISM: Oryza sativa

<400> SEQUENCE: 42

```
caacactcta aaagtttttt ttttacccgt tcacttgcct tgttagtcta tctgtacttt    60
atgatcataa atagttttat aataaagcat gacggatttt tgtttcaagt ttggttgctg   120
aaaaacgtac ggacaaacca tgaactaact tgctattttg ctccacatgg gtttgtctcg   180
aagcaaccag gaattgatca acttcggtgg tttgccaaga acatgaaacc tggggataag   240
gattttttc gactttgcta atgctggtcg tctggattag gaacagaaca ggtattgcta   300
ctgcttttat tcctaagctt ctaatacttc tgctcatacg gatacggcca tatacataca   360
taggagtaga ttcgatttga cgtctcaagc agtagatgct g                       401
```

<210> SEQ ID NO 43
<211> LENGTH: 401
<212> TYPE: DNA
<213> ORGANISM: Oryza sativa

<400> SEQUENCE: 43

```
ggtaggcacg gcccgacgag gcccatcggg agccgccgcc gcgtgcccac gcctcatata    60
taaaggccac cgcgtcctct cgcctccgcc agtccgcctc cctcacaacc ctaaccctaa   120
ccctagccgc ctccgccgat ccacgcacgc ctccgcctcc gcctccgcct tgaccgctcc   180
gcctccgctt ccgcctccgt cgatccacgc ctccacctcc acgcgaccac gcctccatct   240
ctccatccct ctccgtcgcc gtctctgatg aacgccttgc cggatctacc accgagggtc   300
gctgcctcgc cggatccgtg accttgtctc atctccgcct ctccagtctt tggatcgttg   360
gccgtgctct cgattccctc tttctttttc attttttttg c                      401
```

<210> SEQ ID NO 44
<211> LENGTH: 401
<212> TYPE: DNA
<213> ORGANISM: Oryza sativa

<400> SEQUENCE: 44

```
ttcacggatt gctcctcacg cgcaatggaa tggcagcagc ctcctcggcc gtcgcccacg    60
tgtcacgagt gcgctcaggc agctgggcct tgattccttg agtctaaatg ggctgcactt   120
tgattgggct gggttcatat gagattaggg gaaaaaacac gaacattcca gtaaaatggg   180
gagtgtgaac tgtgaagaag ggggtaaacg tgtgcggac gtgagacgag aaaagcatga   240
gagaaaacga tctgtgtgca tgcatagggc tggacgaaaa gctcgtgact cgttagctcg   300
ctcggttcgt gtctggctcg gctcggctcg gctcggctcg tttggatttg ttaacgagcc   360
gagctaaggt ttcagctcgt tatctataac gagccagctc g                      401
```

<210> SEQ ID NO 45
<211> LENGTH: 401
<212> TYPE: DNA
<213> ORGANISM: Oryza sativa

<400> SEQUENCE: 45

```
gaaccgaatg acttgttgta tacgttgctc ctgcttctct gcctgatccc tctctgatga    60
tggtgtgtgt cccttttgtt tcgcttttct taatcctctc tagggcttct gatagccctc   120
catctgtccg tcctttgccc gtttgcttct tggcctaaac caccgaaaag gtgggtccgt   180
tttgctggac gcctggaata ctcttcaact cgattggaac agcaggctcc gtgtatgtgt   240
aactatggct gtgtttagat ctaaagttta gattcaaagt atagatttaa acttcagtca   300
```

| | |
|---|---|
| tttttcatca catcaacctg tcatatacac acaacttttt agtcacatca tctttaattt | 360 |
| taaccaaaat ataaatttta cgctgaacta aacacagtat a | 401 |

<210> SEQ ID NO 46
<211> LENGTH: 401
<212> TYPE: DNA
<213> ORGANISM: Oryza sativa

<400> SEQUENCE: 46

| | |
|---|---|
| ccctcgacct cgtcggtggg aggaggacga cggcggtggg aagaacctg aggcggcagc | 60 |
| gagagagaca ggcggtgtcg ccggagcagt gaggagggag cggcgtcga gagagagaag | 120 |
| agagaggcga tggcgacgac gaccggatcc gcgacggcga cgacggatcc gcggcgacga | 180 |
| caaccggatc cggtggcctc ctccacctcc gccttggcct cctcgacctc ggccaccgcg | 240 |
| acctcctcca cctccgtctt ggcctcctct gcgtggcggc gagagagagg caagcagcag | 300 |
| cggcgagaga gagagaggag aaagcggcgg cggcggtggc tggggaggtg gcgccggcgc | 360 |
| tcgcgggaga gagagggaga gggagggag acggcgacg g | 401 |

<210> SEQ ID NO 47
<211> LENGTH: 401
<212> TYPE: DNA
<213> ORGANISM: Oryza sativa

<400> SEQUENCE: 47

| | |
|---|---|
| cggcagcgag agagacaggc ggtgtcgccg gagcagtgag gagggaggcg gcgtcgagag | 60 |
| agagaagaga gaggcgatgg cgacgacgac cggatccgcg acggcgacga cggatccgcg | 120 |
| gcgacgacaa ccggatccgg tggcctcctc cacctccgcc ttggcctcct cgacctcggc | 180 |
| caccgcgacc tcctccacct ccgtcttggc ctcctctgcg tggcggcgag agagaggcaa | 240 |
| gcagcagcgg cgagagagag aggagaaa gcggcggcgg cggtggctgg ggaggtggcg | 300 |
| ccggcgctcg cgggagagag agggagaggg aggggaggac ggcgacggca ccgagtggag | 360 |
| ggagtgaggt ggcgtggagc gaagaaaaaa gaagaggagg g | 401 |

<210> SEQ ID NO 48
<211> LENGTH: 401
<212> TYPE: DNA
<213> ORGANISM: Oryza sativa

<400> SEQUENCE: 48

| | |
|---|---|
| aagacccgca gtgcgaggat ttcgaggatc aagctccaga tctcgagcaa ggcaagccac | 60 |
| ctttgaacat cttgagccta tatttgaaat ttaattatgt tgcttgaaaa atattatgca | 120 |
| ttgataggat cgcacttaat ctgtcgtccc gtctgcaagg cagattggcg gacccaccta | 180 |
| atttgttgca ttgatcctcc cttgttaatt gttatatcat gtcccctgt aaccatctag | 240 |
| ttgcgtctcg acattcgcgc accctgtgcg agcatcgacg gacgccttca aacttaaaat | 300 |
| ctgaaaaaca acttgggtaa aacttgggtt tacaaaagac ttggaaaact cgacacctgg | 360 |
| gtcggtgctt gcgaactaaa tggatttttcc aaaaccgcgg a | 401 |

<210> SEQ ID NO 49
<211> LENGTH: 401
<212> TYPE: DNA
<213> ORGANISM: Oryza sativa

<400> SEQUENCE: 49

```
gaacacccac acaatctcga tttgattgag aatctaggag gatactgatt ggcgctcaag      60
aatggcgtag ttaatgttat gatttgccag cattctcagc tgctgattct caggctgatt     120
ctacttggtt ggtagaaaat ctacttatcc aggaacaagc gtagggtaac ttttcctttt     180
tttctcagct atgtgaaaag ggagaaaact cgctacactt tataggaaat gaactactct     240
tctaccgacg gatatcctaa aggctatcct ctggtacctc ggccttacgc taactcaaaa     300
ccaaactaaa atgggttgat cggagctatt ctctagaatt tttgacccaa attgagcgaa     360
ggcggccact tcgcgatatt gtgccaattc cagtgctcga a                         401
```

<210> SEQ ID NO 50
<211> LENGTH: 401
<212> TYPE: DNA
<213> ORGANISM: Oryza sativa

<400> SEQUENCE: 50

```
tagcagcaga tgtcatacaa acaggctttc attggaagca ataaaaatag tggacatcca      60
aaagatgtgt ggaactatga cttctagata tcacaggcat ctagcatctt gattttatt     120
caagactgca cataacatct ttacattcta gagggaaatg atccgactta agtagtttga     180
tagttcacct cagggaggaa gtcctttgat agtgttatag atgtctcccg aagcaccttg     240
actgccactt cctctccatt gtccaatatg ccatgataaa ccataccaaa tcctcctttt     300
ccaatgatag actggaagtt gttagttata gtcttcaact ctgtatatgt gaatcttctg     360
gtgtcagtat gcagggagt atcctcttca tacatatcat a                          401
```

<210> SEQ ID NO 51
<211> LENGTH: 401
<212> TYPE: DNA
<213> ORGANISM: Oryza sativa

<400> SEQUENCE: 51

```
gtttgggcac cgacagctcc aacggaacaa agaaacgccc taagacctct aataggaagg      60
ctgctactga caatgagatt tccttgatgc ctccatccag cgatcccagg gaggttgtgg     120
aagtgcttct catgaccttc gaggcactgc ggcgtaggca tcttcaattg gatgagacac     180
aagagactag caaacgtgca gacctgaagg ctggtgccat catgttggcc agtaatctga     240
gggctaacat tgggaagagg attggagctg tccctggagt tgaagtaggg gatatttct     300
acttcaggat ggagctatgc attatcggct tgcatgcacc tagcatgggt ggaattgatt     360
atatgaataa gtttggtgat gaggatgact ctgtagcaat a                         401
```

<210> SEQ ID NO 52
<211> LENGTH: 401
<212> TYPE: DNA
<213> ORGANISM: Oryza sativa

<400> SEQUENCE: 52

```
aatgaggaaa ggtgagaatc ggtttgttat tagtaagaag aaagaccgct cactgacatc      60
gccacagtac aaaaggcgca gtgtgctcga gcatgctgat aattccaatt tcatcccatt     120
tgtcccattc cctcctgatt actttgccaa gaaaaataag cctgtggaga attcatcaga     180
tgcaggaata gtgccagaag gccctccatc agctgaaaaa ttaccagaaa caaaatattc     240
atctggaaat ctgggaaatt ttcagaacag ctcacaggtg atgggcagtc aggcagcaaa     300
```

```
caacatgaac aatgagaaca ggaacggaaa ttatccacat caaaacttga gtacaagtgg    360
ttatgggtat ggtgaaagca tcacttatca gcatcaacca c                       401
```

<210> SEQ ID NO 53
<211> LENGTH: 401
<212> TYPE: DNA
<213> ORGANISM: Oryza sativa

<400> SEQUENCE: 53

```
tgatttggtt gatttgtggg cgcgcgcgcg catggcgaag gtacatccta acgtggtgcc    60
cgtggcggcg gcggcagggc cggccggcgg cgagcggcgg ggggaggagg aggaggaggc   120
ggcggcgctg acggtgtggc ggaagtcgct gctgttcaac tgcaaggggt tcacggtgtt   180
cgacgccaag gggaacctgg cgtaccgcgt cgacagctac gacacggaga gcggcgacga   240
ggtcgtcctc atggacgccg ccggcgcccc ggccttcacc gtccgcagga agaggcagct   300
cagcctgcag ggggagcagt ggctcgtgtt cgccggcgag gcggacggcc ggcggccgcc   360
cgtgtacgcg gtcaggcgga cgggccgcgg cggcggcaag t                      401
```

<210> SEQ ID NO 54
<211> LENGTH: 401
<212> TYPE: DNA
<213> ORGANISM: Oryza sativa

<400> SEQUENCE: 54

```
aaaaaatatg gtttcaaagt tttccaaatc ggtaaatcta attggagagg cctctccaat    60
tagtcttaac cagagacacc cacgtgctag tactttagga gttttggttg ctattaatcg   120
attgagcaag tagggaaat attcctatca tctatgcttc aaataaagtt ttctcttaaa    180
ttactcatcc gatttacaat ccgattacac cgttgtgttc gtaataatta aatctttaca   240
acaagatctc acatgattat attttgatga aaaatcacaa attacttta tgatatgtct    300 aaattacttt tagatttcac taagttactt cttagacata taaagtaaa ttcagtaaag    360 cctaaaagta attacatata ttatagcagt aacttataac a                      401
```

<210> SEQ ID NO 55
<211> LENGTH: 401
<212> TYPE: DNA
<213> ORGANISM: Oryza sativa

<400> SEQUENCE: 55

```
aacgtcgacg agaaccgggc tcccaactga cggtcacgcg agagctgcac gaaacgagcc    60
tcgacgacga tcccatccgt ccgtccgtcg ctgcggctgc tgctgctgcc gccacaggcg   120
gtcagagcct ctggcacgat gccaacacgc gggcacgtgg tagggcagca cgggccattc   180
aggtggtgtt tggatccagg gacttaactt tattctctat atttagacac taatttaaaa   240
tattaaatat agattactta caaaactaat tacataaatg aaagctaatt tgtgtgataa   300
cttttttaag cttaattaat ccataattag agaatgttta atgtagcatc acataagcta   360
atcatggatt aattaggctc aatagattcg tctcgcgaat t                      401
```

<210> SEQ ID NO 56
<211> LENGTH: 401
<212> TYPE: DNA
<213> ORGANISM: Oryza sativa

<400> SEQUENCE: 56

```
cgtccgccga agcgcacgac cggcgcggcg tggggagcgg cgagtcgagc agctgcggga    60
gcttctcgcc gtcggcgcca ttgcaccgca gcccctcctt gtcccgcctg gtgacgattt   120
ccatgggcat tgcgccgact gactgtgtcg gcagcatgca tcgtctcggg cgttcaacgt   180
gtggaggga cgacgtataa gagtacacgc gaagactgta ggtagaggtg cttttcccgc   240
gaaaagtggc agtagcggcg gttggacagt aaccttcgtg tatggttgtg tgttcatctc   300
acgtactgtt cttttgcctc tcgctagctc gttcccgtga tcaaggtgca tgctcgatgg   360
ccttaatggt ggaggttgcc gaaaggtagc agaggaaatc a                       401
```

<210> SEQ ID NO 57
<211> LENGTH: 401
<212> TYPE: DNA
<213> ORGANISM: Oryza sativa

<400> SEQUENCE: 57

```
ggatggatag taaatataat atgaattgat ctattggatc agttatatat atatatatat    60
atatatatat atatatatat atatatatat atatatagac acacacacac acaatgagga   120
tggtaaatta gtgacaatat atgaatgtgt tctattgtca aaacgaaagg gatcgatgag   180
ttatatctct aggttaatta gtttacaacg aagagttgaa gctggaataa acaagtcaaa   240
attatatctg tataacatca tagtaatgcc gaccatgtac gcatccacat ggccatacag   300
caacatcaga aacagaattt aattaattat ttgactaaac ccagaatcat ttgctgctgc   360
atcgaatcgt tcctctcgtc atcgccgacg caaacatgcg c                       401
```

<210> SEQ ID NO 58
<211> LENGTH: 401
<212> TYPE: DNA
<213> ORGANISM: Oryza sativa

<400> SEQUENCE: 58

```
ctatgagtta gctagctaac gtgtatgatg tccaatgatt aagtgacact tttttctgt    60
ctaatataat catccatctc atcatatcat tagctccttg tgcttgtgcg ttcactgttc   120
agagaagctg gttatcctcc ctgataagaa cagccgggag gtcagtgtgc tatggttttg   180
tttagttctg gaatgatcca gtcacccagc acaattgact ggctgagtgt tgcattaagc   240
aaatctggac cggatttgag ggaattttct cgcgcagtgg agatctatga taaatctcgt   300
accgatccag catagtgatt cgtccgcggg attaatactg taactaatcc atagattagc   360
gccattattg aaacacgctt tcttcttatt gttgttatta t                       401
```

<210> SEQ ID NO 59
<211> LENGTH: 401
<212> TYPE: DNA
<213> ORGANISM: Oryza sativa

<400> SEQUENCE: 59

```
actctgtagt ctgcaaggag cggtggcgag cagtggcgcg cgaagtcgat agggtggcga    60
gcggacggag tggcgacgga gagcctgcgg gagtcgagat cgtccgggga agcaacgacg   120
gcaacgacgg cagccttgta tcccgtcggc gaggtcacgc tcggccattg cgcacctctc   180
ccttcgccca tcgccatcga gcccccaccc acggcgcccg gccatccccg gcgaggagct   240
ctgttttggg tgggtgtcgg cggagttgga acgaaggagg gtcgttctcg gcatcgatgt   300
```

```
cgccatctcc gatcctccac cgccaccgcc gccctccccc cctccattgc cgacccctcc    360
ccggcgtcga gaaaatcctc gcccgacctc agcaacaaga a                        401
```

<210> SEQ ID NO 60
<211> LENGTH: 401
<212> TYPE: DNA
<213> ORGANISM: Oryza sativa

<400> SEQUENCE: 60

```
tagactgcat cgccacctgc cgccgaactg cgccgtgctg ccgcccgccg gtgccctctc     60
cttcacctcc cgctgcatcg ccgcctgccg ccaagcgcac ggcgaagggt aaggagtcgt    120
ggcggcgcgg ggcgctcatg gcggtggagg acctgctgga tgttgctgct cctgttctcg    180
ccattgtcgg agtcggcgcc gcccacgccg acggagaatc tcaaggaggc gatgagcacg    240
ccgaggctcg gacccagctt cgtcggtggg acaaagcggg actcgatgga gacggtggag    300
ctctcctcct cctcccccaa caccacctca tgtagcttcc ccctcggcgc gtcagtaggt    360
aggggtatcc atcgcttgtg cagctgcacc gagtcctcat c                        401
```

<210> SEQ ID NO 61
<211> LENGTH: 401
<212> TYPE: DNA
<213> ORGANISM: Oryza sativa

<400> SEQUENCE: 61

```
tcctggagga tgagcgtgag cgtgcgcgca agatagcgca cgagatcaag ggattcggca     60
gcttcaacct cagcagcgcg catgcgtcgg ggtcggcggc ggcagccctc cgcgcggggg    120
cgatggagca ccagtgctac ggccggagca actcgcggta cgagggcagg tggaggaggg    180
aggcctgcgt ggacgacggc gacaaggaga acctgctggt ggtgtcgatg ccgaggcga     240 aggccgaggc ggcggcggag gagccgcacc actaccacca cccgttctac ggcttcgggc    300
agcagcggcc ggaggcgatg ctgctcctga gccagtagtg atcgtttggg tggatggttc    360
ttcgtcgatc gcatcgttcg ttggtttgtg atgcgtgaga a                        401
```

<210> SEQ ID NO 62
<211> LENGTH: 401
<212> TYPE: DNA
<213> ORGANISM: Oryza sativa

<400> SEQUENCE: 62

```
agtctgtggc cactgatgac aggcgcagtg caactgagct cctgaagcag atcaggcagc     60
atgctcatgc caatggtgat ggtgatcagc gtttggcaca ctgcttcgcc aacggcctcg    120
aggcgaggct ggcaggtact ggtagtcaaa tttacaagaa ctacacgata actcggcttc    180
catgcactga tgtgctgaaa gcgtaccagc tttatttggc agcttgccca tttaagaaga    240
tctctcatta ctttgccaat caaacaattt tgaatgctgt ggagaaggcc aagaaagttc    300
acattgtcga ttatggcata tactatggat ttcagtggcc gtgtcttatt cagcggctat    360
ctaacaggcc tggaggccca ccaaagctta ggatcactgg a                        401
```

<210> SEQ ID NO 63
<211> LENGTH: 401
<212> TYPE: DNA
<213> ORGANISM: Oryza sativa

```
<400> SEQUENCE: 63
gggcattggt gaaggctcag taaccggagg tcttgtttga tggttggcaa ctgaattgtt      60
aattaccaat ttatttcctg tgcttctaat accagcagca tcacattctg gttgttgagg    120
gtccactgat acctttacct gttgcagttt attgttttaa ataatccaat caaactttg     180 tttgagctta ttgctgaata gcacagcagc agtacatgca atgcaagatg cccagatgat    240
gagaataaag gcaatggcaa aaatataagt gctagttcta tttcaaaata acaaacagac    300
aacattgcat tctaaacttt tataaccaaa caaacaaagg aaacagggaa aattgctgaa    360
ttaatgttcc ctttactaag taaattctac tagaaagcac t                         401

<210> SEQ ID NO 64
<211> LENGTH: 201
<212> TYPE: DNA
<213> ORGANISM: Oryza sativa

<400> SEQUENCE: 64
ataaagatga ggtgtttgat gaattaaagg ccgcagggtt gaagaggcca tgtagcttta     60
cagatatttc cagtgaaaat gctttgcttc ttgaatttga kacagcaact gatgcagctg    120
ctgcgaaagc ccatattagg cgccagcttc atccagatgt ctgttcccag gacaagaata    180
cttctggtca tgaactttt g                                                201

<210> SEQ ID NO 65
<211> LENGTH: 201
<212> TYPE: DNA
<213> ORGANISM: Oryza sativa

<400> SEQUENCE: 65
tcacatgatc tgcaactgtc aacagtctta ccggaattgg attctgaagg tggatactcc     60
acctgtccac cataagtcct tatttgtcag aggttacaat ygcatgatgt gtctatactc    120
tatactgcaa agatgaatac taacaagttt ttcttgggct taaaagaaga aaaactagga    180
acagcctcac tagtttgcta g                                               201
```